US009877926B2

(12) United States Patent
Zilberman et al.

(10) Patent No.: US 9,877,926 B2
(45) Date of Patent: Jan. 30, 2018

(54) FORMULATIONS AND KITS FOR FORMING BIOADHESIVE MATRICES

(71) Applicant: Technology Innovation Momentum Fund (Israel) Limited Partnership, Tel-Aviv (IL)

(72) Inventors: Meital Zilberman, Tel-Aviv (IL);
Adaya Shefy-Peleg, Givataim (IL);
Binyamin Cohen, Tiberias (IL);
Maytal Foox, Nes Ziona (IL)

(73) Assignee: Technology Innovation Momentum Fund (Israel) Limited Partnership, Tel-Aviv (IL)

( * ) Notice: Subject to any disclaimer, the term of this patent is extended or adjusted under 35 U.S.C. 154(b) by 0 days.

(21) Appl. No.: 14/379,303

(22) PCT Filed: Feb. 14, 2013

(86) PCT No.: PCT/IL2013/050139
§ 371 (c)(1),
(2) Date: Aug. 18, 2014

(87) PCT Pub. No.: WO2013/121429
PCT Pub. Date: Aug. 22, 2013

(65) Prior Publication Data
US 2015/0038424 A1 Feb. 5, 2015

Related U.S. Application Data

(60) Provisional application No. 61/599,486, filed on Feb. 16, 2012.

(51) Int. Cl.
*A61K 9/70* (2006.01)
*A61K 31/192* (2006.01)
*A61K 31/44* (2006.01)
*A61L 24/08* (2006.01)
*A61L 24/10* (2006.01)
*A61K 47/12* (2006.01)
*A61K 47/36* (2006.01)
*A61K 47/42* (2017.01)
*A61L 24/04* (2006.01)

(52) U.S. Cl.
CPC ............. *A61K 9/70* (2013.01); *A61K 31/192* (2013.01); *A61K 31/44* (2013.01); *A61K 47/12* (2013.01); *A61K 47/36* (2013.01); *A61K 47/42* (2013.01); *A61L 24/043* (2013.01); *A61L 24/08* (2013.01); *A61L 24/104* (2013.01)

(58) Field of Classification Search
CPC ........ A61K 47/12; A61K 47/36; A61K 47/42; A61K 9/70; A61K 31/192; A61K 31/44; A61L 24/043; A61L 24/104; A61L 24/108; C08L 89/06; C08L 5/08
See application file for complete search history.

(56) References Cited

U.S. PATENT DOCUMENTS

| 5,830,932 A | 11/1998 | Kay | |
|---|---|---|---|
| 2005/0079999 A1* | 4/2005 | Wilkie | A61L 24/001 514/21.2 |
| 2006/0068013 A1* | 3/2006 | DiTizio | A61K 9/7007 424/484 |
| 2006/0233850 A1* | 10/2006 | Michal | 424/422 |
| 2011/0066182 A1 | 3/2011 | Falus | |

FOREIGN PATENT DOCUMENTS

| WO | WO 2009153750 A2 * | 12/2009 | ............. A61K 8/042 |
|---|---|---|---|
| WO | WO 2013/121429 | 8/2013 | |

OTHER PUBLICATIONS

Sung et al (1999). "Evaluation of gelatin hydrogel crosslinked with various crosslinking agents as bioadhesives: In vitro study." Bioadhesives, pp. 520-530.*
International Preliminary Report on Patentability dated Aug. 28, 2014 From the International Searching Authority Re. Application No. PCT/IL2013/050139.
International Search Report and the Written Opinion dated May 21, 2013 From the International Searching Authority Re. Application No. PCT/IL2013/050139.
Bae et al. "A Soft-Tissue Gelatin Bioadhesive Reinforced With a Proteinoid", Journal of Adhesion Science and Technology, 16(4): 361-372, 2002.
Choi et al. "Study on Gelatin-Containing Artificial Skin: I. Preparation and Characteristics of Novel Gelatin-Alginate Sponge", Biomaterials, 20: 409-417, 1999.
Ghavamzadeh et al. "Bioadhesion and Biocompatibility Evaluations of Gelatin and Polyacrylic Acid as a Crosslinked Hydrogel In Vitro", Journal of Biomaterials Science-Polymer Edition, 15(8): 1019-1031, 2004. p. 1024, fig.4, p. 1030.
Hsu et al. "The Properties of Gelatin-Poly (Gamma-Glutamic Acid) Hydrogels as Biological Glues", Biorheology, f44: 17-28, 2007.
Liang et al. "Crosslinking Structures of Gelatin Hydrogels Crosslinked with Genipin or a Water-Soluble Carbodiimide", Journal of Applied Polymer Science, 91(6):4017-4026, 2004. p. 4018, Left col.
McDermott et al. "Mechanical Properties of Biomimetic Tissue Adhesive Based on the Microbial Transglutaminase-Catalyzed Crosslinking of Gelatin", Biomacromolecules, 5: 1270-1279, 2004.
Mo et al. "A Tissue Adhesives Evaluated In Vitro and In Vivo Analysis", Journal of Biomedical Materials Research, Part A, 94(1): 326-332, Jul. 2010.

(Continued)

*Primary Examiner* — Anoop K Singh
*Assistant Examiner* — Doan T Phan

(57) ABSTRACT

A bioadhesive formulation, comprising gelatin, alginate and a coupling agent, capable of forming a bioadhesive matrix, which is characterized by rapid curing, optimal viscosity, high bonding strength, flexibility, biocompatibility and biodegradability, is disclosed. Further disclosed is such a bioadhesive formulation which further comprises a bioactive agent, and a drug-eluting bioadhesive matrix formed therefrom, the bioadhesive matrix being capable of delivering the bioactive agent to a bodily site. Methods utilizing the bioadhesive formulations and matrices in various biological and medical procedures are also disclosed.

12 Claims, 23 Drawing Sheets

(56) References Cited

OTHER PUBLICATIONS

Mo et al. "Soft Tissue Adhesive Composed of Modified Gelatin and Polysaccharides", Journal of Biomaterials Science, Polymer Edition, 11(4): 341-351, 2000.
Okino et al. "In Situ Hydrogelalion of Photocurable Gelatin and Drug Release", Journal of Biomedical Materials Research, 59: 233-245, 2002.
Otani et al. "Rapidly Curable Biological Glue Composed of Gelatin and Poly(L-Glutamic Acid)", Biomaterials, 17: 1387-1391, 1996.
Sung et al. "Evaluation of Gelatin Hydrogel Crosslinked with Various Crosslinking Agents as Bioadhesives: In Vitro Study", Journal of Biomedical Materials Research, 46(4): 520-530, Sep. 15, 1999. p. 521, Left col., p. 524, Fig.6, p. 527, Right col.
Sung et al. "Gelatin-Derived Bioadhesives for Closing Skin Wounds: An In Vivo Study", Journal of Biomaterials Science -Polymer Edition, 10(7): 751-771, 1999. p. 768, Fig.9, p. 753, Para 2.1.
Supplementary European Search Report and the European Search Opinion dated Sep. 2, 2015 From the European Patent Office Re. Application No. 13748848.2.
Translation Dated Mar. 8, 2016 of Notification of Office Action dated Jan. 13, 2016 From the State Intellectual Property Office of the People's Republic of China Re. Application No. 201380020118.4.
Notification of Office Action and Search Report dated Jan. 13, 2016 From the State Intellectual Property Office of the People's Republic of China Re. Application No. 201380020118.4.
Notification of Office Action and Search Report dated Oct. 10, 2016 From the State Intellectual Property Office of the People's Republic of China Re. Application No. 201380020118.4 and its Translation of Office Action Into English.
Communication Pursuant to Article 94(3) EPC Dated Mar. 24, 2017 From the European Patent Office Re. Application No. 13748848.2. (6 Pages).
Notification of Office Action dated Apr. 19, 2017 From the State Intellectual Property Office of the People's Republic of China Re. Application No. 201380020118.4. (4 Pages) (with English Translation).
E. Vandor et al., "A critical study on the preparation and application of gelatin-resorcinol tissue adhesive crosslinked by formaldehyde" Z. Exper. Chirurg. 13:41-51(1980).
Cohen et al., "Gelatin—alginate novel tissue adhesives and their formulation—strength effects" Acta Biomaterialia 9 9004-9011 (2013).
Olde Damink et al., "Cross-linking of dermal sheep collagen using a water-soluble carbodiimide" Biomaterials 17:765-773 (1996).
Otani et al., A new biological glue for gelatin and poly (L-glutamic acid), Journal of Biomedical Materials Research, 31:157-166 (1996).

* cited by examiner

FIG. 19A
FIG. 19B
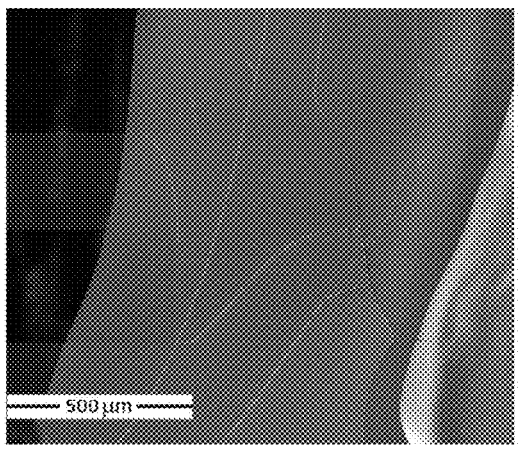
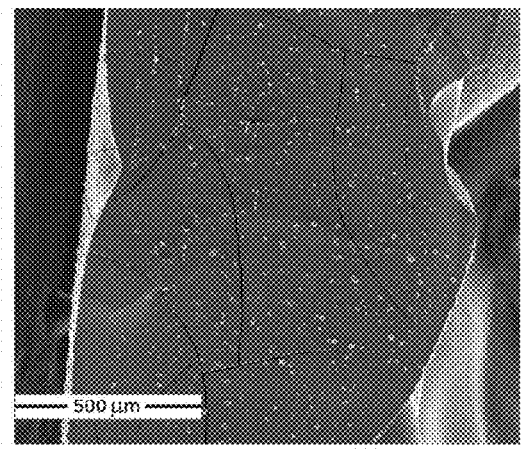
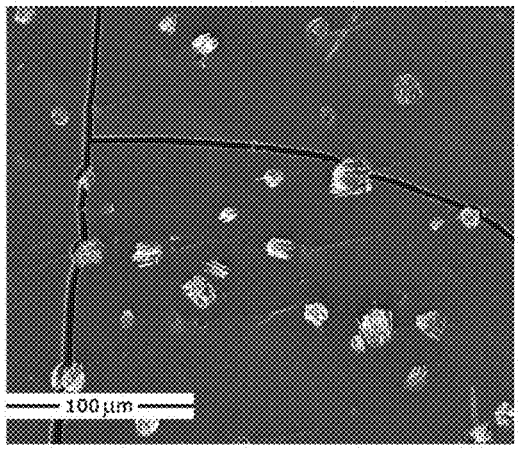
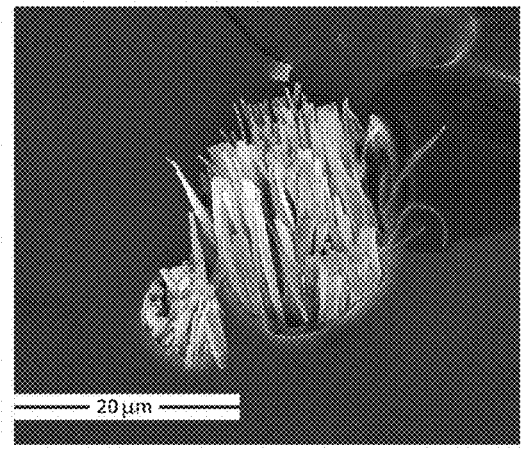
FIG. 19C
FIG. 19D

FIG. 20A
FIG. 20B
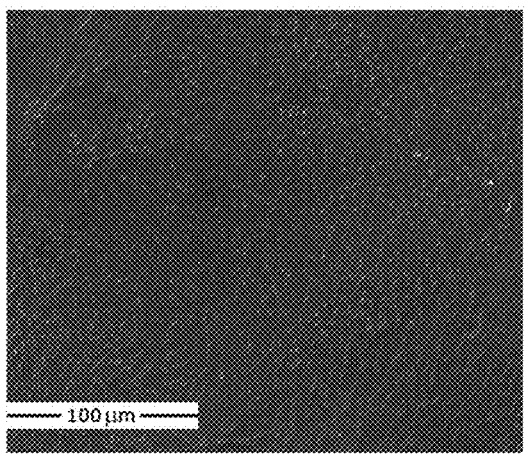
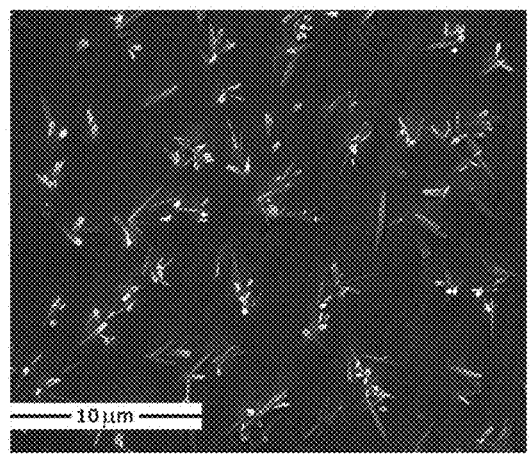

FIG. 24A  FIG. 24D
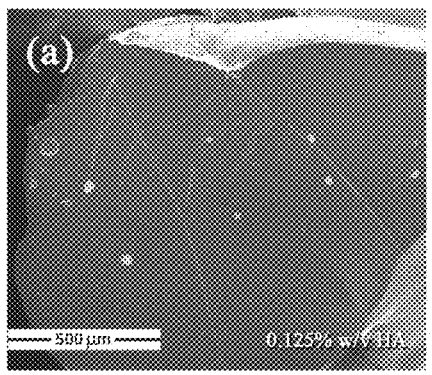
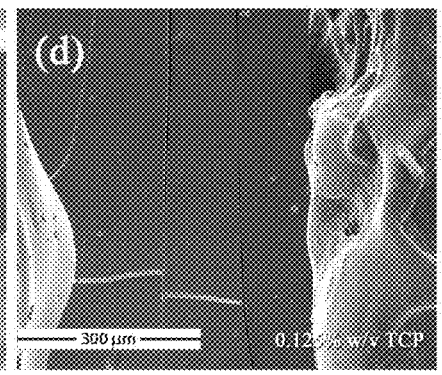
FIG. 24B 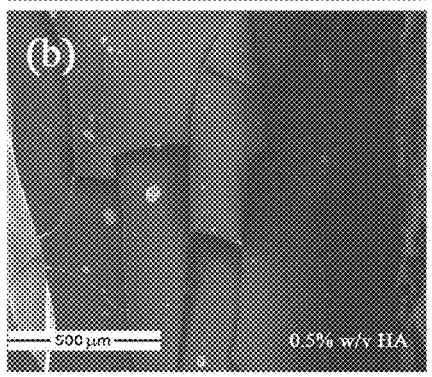 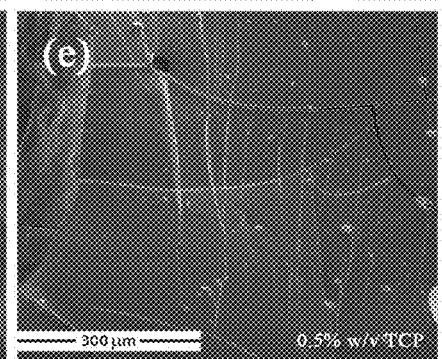 FIG. 24E
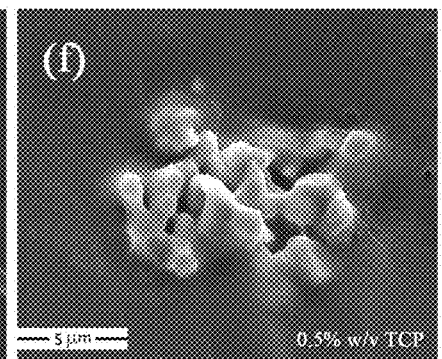
FIG. 24C  FIG. 24F

FORMULATIONS AND KITS FOR FORMING BIOADHESIVE MATRICES

RELATED APPLICATIONS

This application is a National Phase of PCT Patent Application No. PCT/IL2013/050139 having International filing date of Feb. 14, 2013, which claims the benefit of priority under 35 USC § 119(e) of U.S. Provisional Patent Application No. 61/599,486 filed on Feb. 16, 2012. The contents of the above applications are all incorporated by reference as if fully set forth herein in their entirety.

FIELD AND BACKGROUND OF THE INVENTION

The present invention, in some embodiments thereof, relates to bioadhesive matrices, and more particularly, but not exclusively, to bioadhesive matrices, to formulations and kits for forming same and to uses thereof for adhering two or more objects, including biological objects such as viable tissues, organs and the likes.

In recent years there has developed an increased interest in replacing or augmenting sutures and staples with bioadhesive matrices (also referred to in the art as bioadhesive compositions). The reasons for this increased interest include the potential speed with which internal surgical procedures might be accomplished; the ability of a bonding substance to effect complete closure, thus preventing seepage of fluids; the possibility of forming a bond without excessive deformation of the treated tissue; obviate the need for suture removal; cause less pain to the patient; its use requires simpler equipment which presents no risk of injury to the practitioner from sharp instruments; it provides lesser scar; and lowers the probability for infections.

Bioadhesives may also be used for sealing air and body fluid leaks, which may occasionally be resistant to conventional suture or stapling techniques; be used for topical wound closure; repair aortic dissections; and for internal and/or external fixation of certain devices.

Like any adhesive matrix, bioadhesive matrices are formed upon curing a corresponding formulation. Thus, the formulation is applied onto e.g., a biological object, and when subjected to mixing, curing initiators or other curing initiating conditions, cures so as to afford the bioadhesive matrix.

In order for bioadhesive matrices to be acceptable, they must possess a number of properties, such as biocompatibility and biodegradability, and optimal bonding strength and elasticity once cured. Further, the bioadhesive matrices should be designed such that the corresponding formulation exhibits a user-friendly consistency and curing/bonding time. More specifically, bioadhesive formulations should exhibit optimal initial viscosity and tack to allow adequate and easy application; not too fluid so as not to flow away from the wound edges and not too viscous so as to interfere with even and proper application, and at the same time solidify quickly with short curing/gelation time, yet, not too short curing/gelation time, so as to allow smooth application to the desired site. In addition, bioadhesive formulations/matrices should exhibit an ability to bond rapidly to living tissue under wet conditions of bodily fluids; the bioadhesive matrix should form a bridge, typically a permeable flexible bridge; and the bioadhesive formulation, matrix and/or its metabolic (biodegradation) products should not cause local histotoxic or carcinogenic effects, while not interfering with the body's natural healing mechanisms.

Bioadhesives can be used in many surgical procedures including corneal perforations, episiotomy, caesarian cases, cleft lip, skin and bone grafting, tendon repair, hernia, thyroid surgery, periodontal surgery, gingivectomy, dental implants, oral ulcerations, gastric varices wounds of internal organs such as liver and pancreas, attachment and immobilization of external and internal medical devices and more.

Fixing fractured hard tissues using an appropriate bioadhesive material instead of the traditional nailing and plating methods is also considered an attractive technique.

The advantages include providing an optimal load transfer from one fracture side to the other, avoiding stress-shielding phenomena and the ability to repair small or thin bone fragments. Yet, in spite of the clear medical necessity, there is no hard tissue bioadhesive product available for clinical use to date.

Several materials useful as tissue adhesives or tissue sealants are currently available.

One type of adhesive that is currently available is a cyanoacrylate adhesive.

Cyanoacrylates, such as 2-octyl cyanoacrylate, known as Dermabond®, create a strong bond to tissue, enables rapid hemostasis and have the ability to polymerize in contact with fluids that are present at the biological surfaces. However, cyanoacrylate adhesives were found to be cytotoxic, the viscosity of the pre-cured adhesive formulation is too low and the cured cyanoacrylate matrix is stiff and non-biodegradable, interfering with normal wound healing. Hence, non-optimal viscosity, high flexural modulus and reports of cancer in animal experiments limited the use of cyanoacrylates to surface application on oral mucosa and life threatening arteriovenous.

Other known bioadhesive formulations are based on gelatin-resorcinol-formaldehyde, wherein a mixture of gelatin and resorcinol is warmed and crosslinked within tens of seconds by the addition of formaldehyde. The advantage of bioadhesives formed from such formulations is adequate bonding strength; however, cytotoxicity overshadows the advantages.

Another type of a currently available bioadhesive which is used as a tissue sealant utilizes components derived from bovine and/or human sources. For example, fibrin-based adhesive formulations are typically prepared by mixing a solution of fibrinogen and factor XIII with a solution of thrombin and $CaCl_2$. The two solutions are applied by a twin syringe equipped with a mixing nozzle, and the reaction is similar to white fibrin clot in blood clotting. Commercially available examples include Baxter Tisseel® and Ethicon Crosseal™. Advantages of fibrin-based bioadhesive matrices include hemostatic effect, biodegradability, good adherence to connective tissue and promotion of wound healing. Disadvantages include low strength (adhesive and cohesive), low viscosity (hard to apply only to the desired site) and risk of infection as in use of any human-origin product. In the United States fibrin adhesives are prepared from the patient's own blood in order to prevent contamination; however, this process is time consuming and expensive. Other limitations include air leakage in lung surgery that can reoccur a few days after surgery, possibly due to too-rapid absorption of the fibrin adhesive bridge.

Other known bioadhesives are protein-based tissue adhesives which are based on albumin or gelatin. The addition of polyamine, especially poly(lysine) or chitosan, or a polycarboxylate, especially citric acid or poly(acrylic acid), to increase the rate of crosslinking was also described. However, such bioadhesives are typically characterized by insufficient biocompatibility and strength.

Sung et al. [*Journal of Biomedical Materials Research*, Volume 46, Issue 4, pages 520-530, 15 Sep. 1999] report evaluation of various bioadhesive formulations including a formulation based on gelatin, alginate and carbodiimide.

However, the formulations reported by Sung et al., are based on about 600 mg/ml gelatin content or higher, which do not afford a workable bioadhesive formulation.

Additional background art include U.S. Patent Application Publication Nos. 20030083286, 20040156794, 20060013873, 20090098176, US20090099149 and 20110280952, and U.S. Pat. Nos. 5,284,659 and 5,955,502, and Hsu, S. et al., *Biorheology*, 2007. 44(1): p. 17-28; Otani, Y. et al., *Biomaterials*, 1996. 17(14): p. 1387-1391; Bae, S. K. et al., *Journal of Adhesion Science and Technology*, 2002. 16(4): p. 361-372; Mo, X. et al., *Journal of Biomaterials Science, Polymer Edition*, 2000. 11(4): p. 341-351; McDermott, M. K., et al., *Biomacromolecules*, 2004. 5(4): p. 1270; Mo, X. et al., *Journal of Biomedical Materials Research Part A*, 2010. 94(1): p. 326-332; and Okino, H., et al., *Journal of Biomedical Materials Research Part A*, 2002. 59(2): p. 233-245.

SUMMARY OF THE INVENTION

The present inventors have designed and successfully prepared and practiced novel bioadhesive formulations capable of forming bioadhesive matrices which are characterized by rapid curing, optimal viscosity, high bonding strength, flexibility, biocompatibility and biodegradability.

The bioadhesive formulations presented herein comprise gelatin, alginate and a coupling agent, and may further include a bioactive agent, for forming drug-eluting bioadhesive matrices.

The bioadhesive formulations and matrices presented herewith may be beneficially used in various biological and medical procedures.

Hence, according to an aspect of some embodiments of the present invention, there is provided a bioadhesive formulation which comprises gelatin, alginate, a coupling agent, water and at least one bioactive agent; the formulation being characterized by a room temperature viscosity that ranges from 1 Pa-sec to 50 Pa-sec.

In some embodiments, the bioadhesive formulation is intended for forming a drug-eluting bioadhesive matrix upon curing, wherein a curing time for forming the matrix ranges from 5 seconds to 30 minutes.

In some embodiments, the bioadhesive formulation is such that the matrix is characterized by at least one of:

a bonding strength of viable biological objects that ranges from 2,000 pascal to 60,000 pascal;

a flexural strength at physiological conditions that ranges from 0.5 MPa to 200 MPa; and a biodegradability rate that ranges from 7 days to 6 months.

According to another aspect of some embodiments of the present invention, there is provided a bioadhesive formulation which comprises gelatin, alginate, a coupling agent and water; the formulation being characterized by a room temperature viscosity that ranges from 1 Pa-sec to 50 Pa-sec.

In some embodiments, the concentration of gelatin in any of the formulations described herein ranges from 50 mg/ml to 500 mg/ml.

In some embodiments, the concentration of alginate in any of the formulations described herein ranges from 5 mg/ml to 100 mg/ml.

In some embodiments, the concentration of the coupling agent in any of the formulations described herein ranges from 1 mg/ml to 50 mg/ml.

In some embodiments, the concentration of gelatin ranges from 200 mg/ml to 300 mg/ml, the concentration of alginate ranges from 20 mg/ml to 40 mg/ml and the concentration of the coupling agent ranges from 10 mg/ml to 30 mg/ml.

In some embodiments, a bioadhesive formulation as described herein further includes a crosslinking promoting agent selected from the group consisting of an NHS-ester, N-hydroxysuccinimide (NHS), sulfo-NHS, HOBt, HOAt, HBtU, HCtU, HAtU, TBtU, PyBOP, DIC and pentafluorophenol.

In some embodiments, the bioadhesive formulation presented herein further comprises a filler as described herein.

In some embodiments, a bioadhesive formulation as described herein is identified for use in bonding at least two objects to one another, at least one of the objects being a biological object.

In some embodiments, the bioadhesive formulation as described herein is prepared ex vivo, in vitro or in situ.

According to another aspect of some embodiments of the present invention, there is provided a use of a bioadhesive formulation as presented herein in the manufacture of a product for use as a bioadhesive matrix, and, if the formulation comprises a bioactive agent, for use a drug-eluting bioadhesive matrix.

According to another aspect of some embodiments of the present invention, there is provided a use of a formulation as presented herein in the manufacture of a product for bonding at least two objects to one another, at least one of the objects being a biological object.

According to another aspect of some embodiments of the present invention there is provided a bioadhesive matrix, formed by curing the formulation presented herein.

According to another aspect of some embodiments of the present invention there is provided a drug-eluting bioadhesive matrix, formed by preparing the formulation presented herein which includes a bioactive agent, and allowing a curing time to elapse.

According to another aspect of some embodiments of the present invention there is provided a kit which includes the bioadhesive formulation as presented herein.

According to another aspect of some embodiments of the present invention there is provided a method of forming a bioadhesive matrix or a drug-eluting bioadhesive matrix, the method being carried out by preparing the formulation as presented herein and allowing the curing to elapse.

In some embodiments, the method further includes: applying the formulation onto at least one of the objects; and adjoining the objects.

According to another aspect of some embodiments of the present invention there is provided a method of bonding at least two objects to one another, at least one of the objects being a biological object, the method being carried out by: preparing the formulation as presented herein; applying the formulation onto at least one of the objects; adjoining the objects; and allowing a curing time to elapse.

According to another aspect of some embodiments of the present invention there is provided a bioadhesive matrix which includes a gelatin and an alginate covalently coupled to one another.

In some embodiments, the matrix further comprises at least one bioactive agent sequestered therein, thereby forming a drug-eluting bioadhesive matrix.

In some embodiments, any of the bioadhesive matrices described herein is characterized by at least one of:

a bonding strength of viable biological objects that ranges from 2,000 pascal to 60,000 pascal; a flexural strength at physiological conditions that ranges from 0.5 MPa to 200 MPa; and a biodegradability rate that ranges from 7 days to 6 months.

In some embodiments, any of the bioadhesive matrices is formed by preparing the bioadhesive formulation presented herein and allowing a curing time to elapse.

In some embodiments, the preparation of the formulation takes place ex vivo, in vitro or in situ.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 19A-D present ESEM fractographs of bioadhesive matrices, prepared using gelatin (200 mg/ml), alginate (40 mg/ml) and EDC (20 mg/ml) without the addition of a drug (FIG. 19A) and loaded with 1% w/v bupivacaine (FIGS. 19B-D), at different magnification power;

FIGS. 20A-B present ESEM fractographs of bioadhesive matrices, prepared using gelatin (200 mg/ml), alginate (40 mg/ml) and EDC (20 mg/ml) loaded with 1% w/v ibuprofen) at different magnification power;

FIGS. 24A-F present ESEM fractographs of bioadhesive matrices made from bioadhesive formulations, according to embodiments of the present invention, comprising gelatin (200 mg/ml), alginate (40 mg/ml) and EDC (20 mg/ml) as well as 0.125% w/v HA (FIG. 24A), 0.5% w/v HA (FIGS. 24B and 24C at different magnification), 0.125% w/v β-TCP (FIG. 24D) and 0.5% w/v β-TCP (FIGS. 24E and 24F at different magnification);

DESCRIPTION OF SPECIFIC EMBODIMENTS OF THE INVENTION

Figure 1:
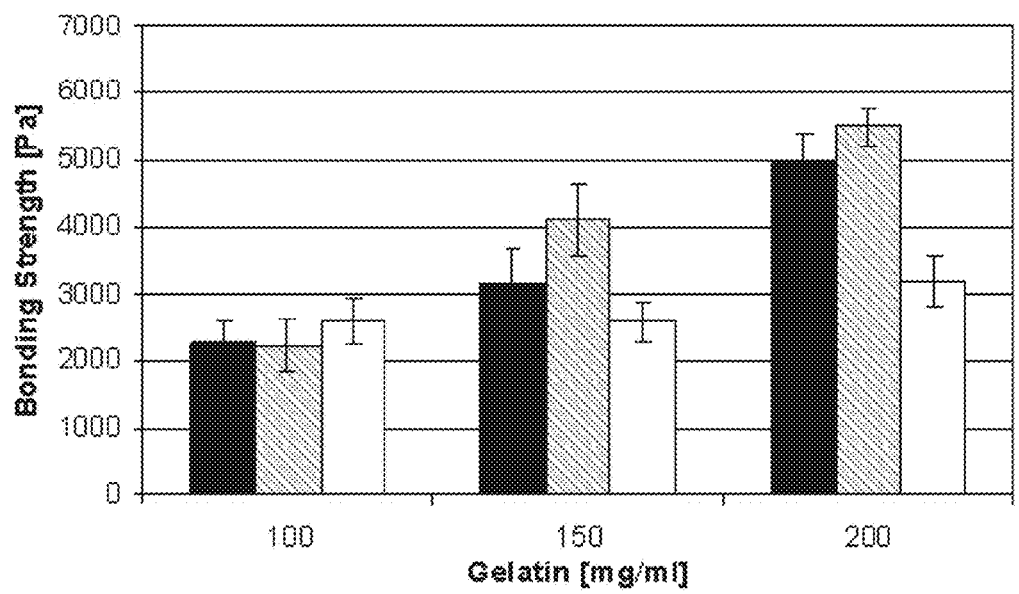
FIG. 1 presents a comparative bar plot showing the effect of gelatin and alginate concentrations in exemplary bioadhesive formulations, according to some embodiments of the present invention, on the bonding strength of the resulting bioadhesive matrix, wherein EDC concentration in the formulation is 4 mg/ml, gelatin concentration varies: 100 mg/ml (left series), 150 mg/ml (middle series) and 200 mg/ml (right series), and alginate concentration varies: 20 mg/ml (black bars), 40 mg/ml (grey bars) and 60 mg/ml (white bars)

The present invention, in some embodiments thereof, relates to bioadhesive matrices, and more particularly, but not exclusively, to bioadhesive matrices, to formulations and kits for forming same and to uses thereof for adhering two or more objects, including biological objects such as viable tissues, organs and the likes.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventors have developed and studied highly effective bioadhesive formulations which are based on gelatin, alginate and a coupling agent such as EDC, and which can be effectively used, inter alia, for adhering soft tissues.

While further developing these bioadhesive formulations, it was shown that these bioadhesive formulations form bioadhesive matrices which can sequester and subsequently elute effectively a bioactive agent, such as various anesthetic and analgesic drugs. The present inventors have practiced this novel concept of drug-eluting bioadhesive matrices using bupivacaine and ibuprofen as exemplary bioactive agents. The effect of the components of the bioadhesive formulation on the bonding strength and on the drug release profile of the resulting bioadhesive matrices was studied, as well as the biocompatibility of these bioadhesive matrices.

While further developing these bioadhesive formulations, it was found that the addition of certain fillers, such as hydroxyapatite (HA) and beta-tricalcium phosphate ($\beta$-TCP), affords a highly effective bioadhesive for hard tissue. While reducing some of the embodiments of the present invention to practice, the potential of these fillers to increase the bonding strength of a bioadhesive matrix to hard tissues has also been demonstrated; HA and $\beta$-TCP were found to improve the bioadhesive matrices, thus affording bioadhesive formulations which can be used for both soft and hard tissue applications.

As used herein, the term "bioadhesive" refers to a feature of a substance (e.g., a formulation or a matrix) according to which when the substance interfaces a living tissue, it enables to adhere to this living tissue an object such as, for example, another living soft and/or hard tissue, the living tissue itself and/or an inanimate object.

As used herein, a bioadhesive formulation thus refers to a formulation which is applied to such a living tissue and/or to the object to be adhered to the living tissue, with the aim of adhering the living tissue and the object; and a bioadhesive matrix refers to the substance that binds together the living tissue and the object adhered thereto.

According to an aspect of some embodiments of the present invention, there is provided a bioadhesive formulation which comprises:
 a) gelatin;
 b) alginate;
 c) a coupling agent; and
 d) water.

It is noted herein and discussed in detailed hereinbelow, that according to some embodiments of the present invention, the formulation is defined as a collection of ingredients, which may be found in the form of one concoction wherein all ingredients are mixed into the same mixture, or in the form of separate quantified ingredients, for example, separate quantified solvents and dry ingredients.

The bioadhesive formulation, as referred to herein, is a precursor of a corresponding bioadhesive matrix.

In some embodiments, the bioadhesive matrix is formed by curing the bioadhesive formulation, such that the bioadhesive formulation can be regarded as a pre-curing formulation.

Basic Ingredients of the Bioadhesive Formulation:

A bioadhesive formulation, as disclosed herein, contains at least two types of polymers (e.g., alginate and gelatin) and a coupling agent.

The bioadhesive formulation is designed to undergo a crosslinking reaction in the presence of the coupling agent.

Without being bound by any particular theory, it is assumed that the crosslinking reaction involves crosslinking of gelatin strands with alginate strands, essentially by coupling primary amines in the gelatin to carboxyl groups in the alginate, and/or with one or more other gelatin molecules. When using a fluid formulation comprising gelatin as a major component and alginate as a minor component relative to gelatin, it is assumed that most of the crosslinks form between gelatin and alginate. This network of crosslinked polymers, being substantially gelatin and alginate, referred to herein as a matrix, is the cured semi-solid, gel product of the fluid bioadhesive formulation. Hence, the matrix is regarded as a coupled gelatin-alginate matrix afforded by coupling gelatin and alginate using a coupling agent.

As used herein, and is known in the art, the term "gelatin" describes a water soluble protein that can form gel under certain conditions. Gelatin is typically obtained by heat dissolution at acidic or alkaline and partially hydrolyzing conditions of collagen.

Type A gelatin is obtained by acidic process and has a high density of amino groups causing a positive charge. Type B gelatin is obtained by alkaline process and has high density of carboxyl groups causing negative charge. There are different sources for collagen such as animal skin and bone, which afford a variety of gelatin forms with a range of physical and chemical properties. Typically, gelatin contains eighteen amino acids that are linked in partially ordered fashion; glycine or alanine is about a third to half of the residues, proline or hydroxyproline are about one fourth and the remaining forth include acidic or basic amino acid residues. Typically, in order to dissolve gelatin in water it is necessary to reach a temperature of at least 35° C. by heating or stirring and adding hot water. Moderate heating enhances solubility and severe heating may cause aggregation or partial hydrolysis of gelatin. The viscosity of gelatin varies with type, concentration, time and temperature. Acid processed gelatin has slightly greater intrinsic viscosity compared to alkali processed gelatin. Gelatin is relatively cheap, it is biocompatible with negligible immunologic problems, and it is biodegradable. "Bloom" is a test to measure the strength of a gel or gelatin. The test determines the weight (in grams) needed by a probe (normally with a diameter of 0.5 inch) to deflect the surface of the gel 4 mm without breaking it. The result is expressed in Bloom grades or Bloom number, and it is typically between 30 and 300 Bloom. To perform the Bloom test on gelatin, a 6.67% gelatin solution is kept for 17-18 hours at 10° C. prior to being tested.

In the context of embodiments of the present invention, alternatives to gelatin may include non-animal gel sources such as agar-agar (a complex carbohydrate harvested from seaweed), carrageenan (a complex carbohydrate harvested from seaweed), pectin (a colloidal carbohydrate that occur in ripe fruit and vegetables), konjaka (a colloidal carbohydrate extracted from plants of the genus *Amorphophallus*), guar gum (guaran, a type of galactomannan extracted from cluster beans of the genus *Cyamopsis tetragonolobus*) and various combinations thereof with or without gelatin.

As used herein, and is known in the art, the term "alginate" describes an anionic polysaccharide. Alginate, which is also referred to herein and in the art as alginic acid, is a block copolymer composed of β-D mannuronic acid monomers (M blocks) and α-L guluronic acid (G blocks), with different forms of alginate having different ratio of M/G. The term "alginate", as used herein, encompasses various M/G ratio. M/G ratio varies according to the species, source and harvest season of the algae/plant.

In some embodiments, the alginate has an M/G ratio that ranges from 0.3 to 4, from 0.7 to 3, or from 1 to 2. In other embodiments, the M/G ratio is 0.7, 0.9, 1, 1.3, 1.5, 1.7, 1.9, 2, 2.3, 2.5, 2.7, 3, 3.5 or 4.

Alginate is known to form a viscous gum by binding water (capable of absorbing 200-300 times its own weight in water).

Alginate undergoes reversible gelation in aqueous solution under mild conditions through interactions with divalent cations that bind between G-blocks of adjacent alginate chains creating ionic inter chain bridges. Since alginate is generally anionic polymer with carboxyl end, it is known and used as a good mucoadhesive agent.

Naturally occurring alginate is typically produced in marine brown algae (e.g., *Macrocystis pyrifera, Ascophyllum nodosum* and *Laminaria*) and soil bacteria (*Pseudomonas* and *Azotobacter*). Synthetically prepared alginates are also contemplated.

Alginate is relatively cheap, it is biocompatible, evokes no immunologic response in mammals, and it is biodegradable.

In the context of some embodiments of the present invention, alginate can be used in a high-viscosity (HV) form, exhibiting more than 2 Pa-sec, or low-viscosity (LV) form, exhibiting 0.1-0.3 Pa-sec. As demonstrated in the Examples section hereinbelow, use of the LV/HV alginate forms adds another parameter to the fine-tuning and optimization of the bioadhesive formulation presented herein.

The term "coupling agent", as used herein, refers to a reagent that can catalyze or form a bond between two or more functional groups intra-molecularly, inter-molecularly or both. Coupling agents are widely used to increase polymeric networks and promote crosslinking between polymeric chains, hence, in the context of some embodiments of the present invention, the coupling agent is such that can promote crosslinking between polymeric chains; or such that can promote crosslinking between amino functional groups and carboxylic functional groups, or between other chemically compatible functional groups of polymeric chains; or is such that can promote crosslinking between gelatin and alginate. In some embodiments of the present invention the term "coupling agent" may be replaced with the term "crosslinking agent". In some embodiments, one of the polymers serves as the coupling agent and acts as a crosslinking polymer.

By "chemically compatible" it is meant that two or more types of functional groups can react with one another so as to form a bond.

Exemplary functional groups which are typically present in gelatins and alginates include, but are not limited to, amines (mostly primary amines —$NH_2$), carboxyls (—$CO_2H$), sulfhydryls and hydroxyls (—SH and —OH respectively), and carbonyls (—COH aldehydes and —CO— ketones).

Primary amines occur at the N-terminus of polypeptide chains (called the alpha-amine), at the side chain of lysine (Lys, K) residues (the epsilon-amine), as found in gelatin, as well as in various naturally occurring polysaccharides and aminoglycosides.

Because of its positive charge at physiologic conditions, primary amines are usually outward-facing (i.e., found on the outer surface) of proteins and other macromolecules; thus, they are usually accessible for conjugation.

Carboxyls occur at the C-terminus of polypeptide chain, at the side chains of aspartic acid (Asp, D) and glutamic acid (Glu, E), as well as in naturally occurring aminoglycosides and polysaccharides such as alginate. Like primary amines, carboxyls are usually on the surface of large polymeric compounds such as proteins and polysaccharides.

Sulfhydryls and hydroxyls occur in the side chain of cysteine (Cys, C) and serine, (Ser, S) respectively. Hydroxyls are abundant in polysaccharides and aminoglycosides.

Carbonyls as ketones or aldehydes can be form in glycoproteins, glycosides and polysaccharides by various oxidizing processes, synthetic and/or natural.

According to some embodiments of the present invention, the coupling agent can be selected according to the type of functional groups and the nature of the crosslinking bond that can be formed therebetween. For example, carboxyl coupling directly to an amine can be afforded using a carbodiimide type coupling agent, such as EDC; amines may be coupled to carboxyls, carbonyls and other reactive functional groups by N-hydroxysuccinimide esters (NHS-esters), imidoester, PFP-ester or hydroxymethyl phosphine; sulfhydryls may be coupled to carboxyls, carbonyls, amines and other reactive functional groups by maleimide, haloacetyl (bromo- or iodo-), pyridyldisulfide and vinyl sulfone; aldehydes as in oxidized carbohydrates, may be coupled to other reactive functional groups with hydrazide; and hydroxyl may be coupled to carboxyls, carbonyls, amines and other reactive functional groups with isocyanate.

Hence, suitable coupling agents that can be used in some embodiments of the present invention include, but are not limited to, carbodiimides, NHS-esters, imidoesters, PFP-esters or hydroxymethyl phosphines.

A carbodiimide is a complete crosslinker that facilitates the direct coupling (conjugation) of carboxyls to primary amines. Thus, unlike other reagents, carbodiimide is a zero-length crosslinker; it does not become part of the final crosslink between the coupled molecules. Because peptides, proteins, polysaccharides and aminoglycosides contain multiple carboxyls and amines, direct carbodiimide-mediated coupling/crosslinking usually causes random polymerization of polypeptides.

EDC, or N-(3-Dimethylaminopropyl)-N'-ethylcarbodiimide hydrochloride, is a widely used carbodiimide-type coupling agent and crosslinker which enables the condensation between carboxyl and amino groups to form amide bonds and the byproduct urea. Once reacted with amine/hydroxyl reactants, EDC is not present in the structure of the coupled product; hence its biocompatibility and biodegradability are not an issue in the context of the present embodiments. As a gelatin molecule exhibits both carboxyl and amino groups, this type of polymer may undergo intermolecular crosslinking by EDC.

It is known that EDC and its urea derivative are cytotoxic and inhibit cell growth. This high reactivity towards amino and carboxyl groups in the living tissues, as well as the release of a urea derivative, are probably the basis for EDC's cytotoxicity.

Alternatives for carbodiimide-type coupling agent, according to some embodiments of the present invention, include without limitation, glyoxal, formaldehyde, glutaraldehyde, polyglutaraldehyde, dextran, citric acid derivatives, microbial transglutaminase and genipin.

In some embodiments, the coupling agent is used up during the coupling reaction, and produces a urea derivative as a byproduct of the coupling reaction between amine and carboxyl groups. The nature of the urea derivative is determined by the nature of the coupling agent used.

According to some embodiments of the present invention, various coupling and crosslinking agents may be combined or used as additives in any given bioadhesive formulation based on gelatin and alginate and a coupling agent, so as to further promote the crosslinking reaction. In a representative example, NHS-esters are added to a carbodiimide-type coupling agent such as EDC.

The addition of NHS to the crosslinking reaction of EDC affords an NHS-activated carboxylic acid group, which is less susceptible to hydrolysis and prevents rearrangements. On the other hand, at high concentration NHS can react with the EDC and compete with the crosslinking reaction, thereby reducing the effective amount of EDC for crosslinking. Hence, reagents such as NHS are referred to herein a crosslinking promoting agents.

By adding various agents that promote the coupling reaction, and, in the context of the present invention, promote the formation of crosslinks in the forming bioadhesive matrix, it is intended to increase the crosslinking efficiency and/or reduce the amount of coupling agent needed to form a matrix the exhibits the desired characteristics, as discussed hereinabove. Hence, such agents are referred to herein as "crosslinking promoting agents". The amount of a crosslinking promoting agent is given as weight/volume per weight/volume percents (w/v/w/v), i.e. relative to the amount of the coupling agent, and according to some embodiments of the present invention, this amount ranges from about 1% to 100%, or from 1% to 200% weight/volume per weight/volume percents.

Representative examples of crosslinking promoting agents include, without limitation, sulfo-NHS, HOBt, HOAt, HBtU, HCtU, HAtU, TBtU, PyBOP, DIC pentafluorophenol and the likes.

As demonstrated in the Examples section that follows, a combination of a crosslinking agent and a crosslinking promoting agent in the bioadhesive formulations presented herein, affords bioadhesive matrices with improved bonding strength.

Furthermore, the combination of a crosslinking agent such as EDC and a crosslinking promoting agent such as N-hydroxysuccinimide (NHS), allowed a significant reduction in the EDC content of the bioadhesive formulation. A reduction of the content of EDC is beneficial due to the medical safety and cytotoxicity implications of using EDC.

In some embodiments, the amount of the crosslinking promoting agent may be 1, 2, 3, 4, 5, 6, 7, 8, 9, 10, 12, 14, 16, 18, 20, 25, 30, 35, 40, 45, 50, 60, 70, 100, 150, 200%, including any value between 1 and 200% relative to the amount of the coupling agent, or can be even higher. In some embodiments of the present invention, the amount of the crosslinking promoting agent is 5, 10, 15, 20, 30 or 40% relative to the amount of the coupling agent, including any value from 5 to 40.

When used in tandem, EDC and NHS afford stronger bonding bioadhesive matrices, even when relatively low concentration of EDC is used. An exemplary formulation comprises an amount of EDC which is 10 mg/ml and an amount of NHS which is 10% relative to the amount of the EDC.

Fillers for Soft and Hard Tissue Bioadhesive Formulations:

In order to provide bioadhesive formulation/matrix exhibiting mechanical and chemical properties suitable for use in the context of, for example, hard tissues, bioactive fillers may be added to the formulation. Such fillers are known to promote bone formation and osseointegration, which are regarded as highly desired for hard tissue bioadhesive formulations/matrices.

The term "filler", as used in the context of some embodiments of the present invention, refers to a substance, typically based on a mineral-rich source, which is biocompatible, non-toxic and able to reinforce the matrix mechanically, and in some embodiments, capable of promoting bone formation and osseointegration. In some embodiments, a "filler" substance is present in the bioadhesive formulation presented herein in the form of a fine powder of an aqueous-insoluble substance, namely having low solubility in aqueous media.

Some fillers, according to some embodiments of the present invention, are also bioresorbable, at least to some significant extent, as can be assessed by their physiologic resorption time. It has been shown that some bioresorbable filler substances act as more than simple space fillers that prevent soft tissue ingrowth. Such filler substances, once undergone physiologic resorption, may leave a consistent latticework of minerals, which were found to be stable in the long term and to act as an osteoconductive trellis for new bone formation. It was also found to promote the formation of blood vessels, which is essential for bone formation.

As used herein, the term "resorbable" refers to a substance which can undergo resorption, as this term is defined hereinbelow. When the resorption process takes place in a biologic system, the substance is referred to as "bioresorbable".

The term "resorption", as used herein, describes a loss of a substance through chemical, biological and/or physiologic processes. Typically, this term is used herein and in the art to describe such a process which involves decomposition of a substance by, e.g., chemical or physical break-down, such as dissolution, hydrolysis and/or phagocytosis, which may be followed by absorption and/or excretion of the breakdown products by the body via, for example, metabolism. The term resorption is therefore often referred to herein and in the art as "bioresorption". Accordingly, the phrase "resorption period", as used herein, refers to the time period of the resorption process.

Non-limiting examples of fillers, according to some embodiments of the present invention, include the following materials listed (some with their approximate physiologic resorption time in parentheses): calcium sulfate of all hydration forms, tricalcium phosphate ($Ca_3(PO_4)_2$) of various crystal form, beta-tricalcium phosphate (β-TCP) (4-12 months), micro-porous hydroxylapatite (HA) particulate (18-36 months), bovine-derived hydroxylapatite with synthetic peptide (18-36 months), calcified algae (6-18 months), synthetic particulate glass ceramic (bioactive glass, 18-24 months), autogenic bone shavings (3-7 months), allogeneic cancellous bone (6-15 months), irradiated cancellous allogeneic bone (4-12 months), inorganic bovine bone (15-30 months), porous anorganic crystal (4-10 months), porous coralline hydroxylapatite (5-7 years) and composite of micro-porous Bioplant HTR polymer coated with calcium hydroxide (10-15 years).

It is noted herein that a filler, according to embodiments of the present invention, may be in a form of a fine or coarse powder, depending on the application and intended use, namely its particles may exhibit an average particle size that ranges from about 1 μm in diameter to about 2 mm. In some embodiments, the average particle size of the filler ranges from 2-30, 5-20, 15-40. 20-50, 50-60 or 50-100 μm in diameter.

As demonstrated in the Examples section that follows, two types of exemplary bioactive ceramic fillers, hydroxyapatite (HA) and beta-tricalcium phosphate (β-TCP), were added to the bioadhesive formulation presented herein in order to afford a bioadhesive formulation/matrix which exhibits improved bonding strength, while using lower amounts of a crosslinking agent (e.g., EDC) relative to corresponding filler-free formulations, and further found to be highly suitable for hard tissue, such as bones. These two exemplary fillers there are characterized by good biocompatibility and lack of toxicity, but and as capable of promoting bone formation and osseointegration.

The effect of adding fillers such as HA and β-TCP into bioadhesive formulation, according to some embodiments of the present invention, has been studied in terms of the microstructure of the resulting bioadhesive matrix and on the resulting bonding strength to both soft and hard tissues ex vivo. It was found that due to their unique interaction with the aqueous media of the formulation and their low solubility therein, the fillers form fibers and aggregates that presumably act as mechanical reinforcement of the matrix.

As demonstrated in the Examples section that follows, fillers such as HA and β-TCP can be used in the bioadhesive formulations presented herein as powders in amounts such as 0.025, 0.05, 0.075, 0.1, 0.125, 0.15, 0.2, 0.225, 0.25, 0.275, 0.3, 0.35, 0.4, 0.45, 0.5, 0.55, 0.6, 1, 1.5, 2, 3 percents weight per volume (% w/v) of the bioadhesive formulation or higher. According to some embodiments, the use of fillers may allow using EDC at low concentrations relative to corresponding filler-free bioadhesive formulations. As can be seen in the experimental results presented hereinbelow, bioadhesive matrices containing concentrations of 0.5% and 0.125% w/v HA or β-TCP respectively according to some exemplary embodiments of the present invention, were found to have bonding strength higher than their filler-free counterparts.

Various additives may be added to the formulation in order to modify its pre-curing characteristics, such as for example, viscosity modifiers for improved application and spread confinement, penetration enhancers, and colorants or fluorescent agents for allowing tracking during application and follow-up; Various additives may be added to the formulation in order to modify its post-curing characteristics, namely additives that affect the characteristics of the resulting matrix, such as for example, additional coupling/crosslinking agents, calcium ions and ions of other earth-metals, which act as gelling agents by virtue of being crosslinkers for various alginate species, plasticizes, hardeners, softeners and other agents for modifying the flexural modulus of the matrix, and additives that affect the release rate, penetration and absorption of the bioactive agent, when present, as discussed in more detail hereinbelow.

It is noted herein that like the filler, some of the additives, as well as some of the bioactive agents described herein, may be added to the formulation in the form of a dry powder. This may be for the sake of simplicity of use, the wish to maintain decrease or augment certain viscosity value of the bioadhesive formulation, or simply because the additive of bioactive agent is not soluble in aqueous media.

Characteristics of the Bioadhesive Formulation:

As discussed hereinabove, a design of an effective bioadhesive formulation should be made while considering several requirements, which include, for example, workability and efficiency, both translated also into safety.

Under the workability and safety considerations, an effective bioadhesive formulation should exhibit a viscosity at room temperature which allows the practitioner to apply and use the formulation under, e.g., clinic conditions. For example, a formulation which is too viscous and thus not spreadable would be difficult to be applied on tissues and a formulation which is not viscous enough and is thus too fluid would be runny and maybe accompanied by undesirable leakage, insufficient adhesion and overall, in enhanced adverse side effects and reduced safety.

Further under the workability and safety consideration, an effective bioadhesive formulation should exhibit a curing time, as defined herein, which allows completing an operation utilizing the formulation in a relatively short time, so as to avoid prolonged operations which may result in enhanced adverse side effects and reduced safety, yet, on the other hand, be sufficiently long to allow accurate positioning and optional re-positioning if required. In some embodiments instantaneous bonding of objects may be undesired, for example in cases where the objects are not easily positioned optimally and a re-positioning step may be required; hence, exceedingly short curing time may be impractical in some embodiments of the present invention. In such cases it is desirable that the bioadhesive formulation allows a period of time for re-positioning (separation and re-adjoining) of the objects to be bonded to one-another. This range of time (window) is referred to as the workable time of the formulation, as discussed further hereinbelow.

It is noted herein that according to some embodiments of the present invention, the formulation can be kept in a number of separated parts, or solutions, at least until all these parts are mixed into a single concoction comprising all ingredients in conjunction or concomitant to its application and use. A detailed discussion regarding multi-part formulations, means of storage, preparation and application of the bioadhesive formulation is presented hereinbelow.

When referring to a viscosity of a multi-part bioadhesive formulation, it pertains essentially to the more viscous part(s) of the formulation, namely the part which contains gelatin, alginate or a mixture of gelatin and alginate with or without a bioactive agent or other additives. This viscous part will essentially maintain similar viscosity as long as the chemical composition thereof is maintained, namely the concentration of the viscosity-conferring polymers (or water content), temperature and molecular structure.

Alternatively, a reference to viscosity pertains to a formulation comprising all ingredients shortly subsequent to their mixing. While the dissolved polymers contribute the most to the high viscosity, the addition of a coupling agent will change the chemical composition of the polymers by effecting crosslinking which irreversibly alters the viscosity essentially regardless of temperature and water content. From practical reasons, when referring herein to viscosity, it is referred to a formulation part containing gelatin and alginate, while the part containing the coupling agent is considered less viscous and minor in volume relative to the viscous part. Measuring the viscosity of the bioadhesive formulation using standard and common practices and equipment may be impractical due to the relatively short curing time. Gelatin and alginate are the predominant contributors to viscosity, while all other constituents and additives are minor viscosity modifiers. The outstanding constituents are the crosslinking agent and the crosslinking promoting agent, which have a direct effect on the viscosity of the formulation, as these agents are responsible for hardening the formulation to a solid bioadhesive matrix. Hence, when measuring the viscosity of the formulation one can measure the viscosity of the formulation prior to the addition of the crosslinking agent and/or the crosslinking promoting agent. It is safely assumed that the viscosity of the formulation lacking the hardening agents is essentially the same as the viscosity of the complete formulation.

As discussed hereinbelow, the bioadhesive formulation is characterized by a "workable time", referring to the time period between the time point where all ingredients are mixed together, to the time point where the formulation is too viscous to work-up. Hence, the reported viscosity of a bioadhesive formulation, according to some embodiments of the present invention, is the effective viscosity during the workable time.

Dynamic viscosity is quantified by various units, depending on the measuring method and other factors. In the context of the present embodiments, dynamic viscosity is referred to in units of Newton second per square meter (N s $m^{-2}$ or Pa-sec), wherein 1 Pa-sec is equivalent to 1 kilogram per meter second (kg $m^{-1}$ $s^{-1}$) and equivalent to 10 poise (P). For example, water at 20° C. are said to have dynamic viscosity of 1 mPa-sec (0.001 Pa-sec), blood at 37° C. is characterized by a viscosity of 3-4 mPa-sec, and honey at 20° C. by 10 Pa-sec.

In the context of the present invention, when referring to the viscosity of the bioadhesive formulation, the actual measured results of the formulation lacking the crosslinking agent and/or the crosslinking promoting agent are taken and regarded as that of the complete bioadhesive formulation.

Thus, according to some embodiments of the present invention, the formulations presented herein are characterized by at least one of:

a room temperature viscosity that ranges from 1 Pa-sec to 50 Pa-sec (referring to either the gelatin-alginate solution, before adding the coupling agent solution, or to the final bioadhesive formulation containing all components just after being mixed together); and a curing time under physiological conditions that ranges from 5 seconds to 30 minutes.

While the criteria for dynamic viscosity is given in Pa-sec units and its values are derived from particular viscosity measurements at a given ambient temperature, it is noted herein that dynamic viscosity can be expressed by other units, and measured by various methods and techniques, all of which can be used to characterize any given bioadhesive formulation or part thereof. For example, while it is simpler to measure dynamic viscosity at room temperature, it may also be useful to report and consider also the dynamic viscosity of bioadhesive formulations at a temperature higher than the working temperature, since it is more efficient and practical to mix and prepare the formulation at higher temperatures, such as 50° C. Alternatively, it may be more informative to report and consider dynamic viscosity at a temperature lower that the standard room temperature since, for example, most operating rooms are kept at a standard temperature lower than room temperature; as well as reporting and considering the viscosity of a bioadhesive formulation at or near body temperature, where the formulations is intended to be applied and used.

Hence, according to some embodiments of the present invention, the dynamic viscosity of the bioadhesive formulation, or the dynamic viscosity of the formulation part containing gelatin and alginate, ranges from 1 Pa-sec to 50 Pa-sec at 20° C., and/or 0.5 Pa-sec to 25 Pa-sec at 37° C.

According to some embodiments of the present invention, the room temperature dynamic viscosity of the bioadhesive formulation, or the dynamic viscosity of the formulation part containing gelatin and alginate, ranges from 1 Pa-sec to 5 Pa-sec, from 5 Pa-sec to 10 Pa-sec, from 10 Pa-sec to 15 Pa-sec, from 15 Pa-sec to 20 Pa-sec, from 20 Pa-sec to 25 Pa-sec, from 25 Pa-sec to 30 Pa-sec, from 30 Pa-sec to 35 Pa-sec, from 35 Pa-sec to 40 Pa-sec, from 40 Pa-sec to 45 Pa-sec, or from 45 Pa-sec to 50 Pa-sec.

As used herein, the phrase "curing time" describes a time period during which the bioadhesive formulation forms a bioadhesive matrix, as described herein.

It is noted herein that while the bioadhesive formulation begins to cure upon contacting the coupling agent with one or both gelatin and/or alginate, this coupling and crosslinking reaction is not instantaneous across the entire bulk of the mass of the formulation. Accordingly, the term "curing time" is defined such that it encompasses the entire process of matrix formation at all its stages, including the "workable time" and the "bonding time". The "workable time" is the time-window between the moment of mixing all the ingredients of the formulation together, to the moment at which the formulation's viscosity is too high, presumably due to its curing process, to allow working with the formulation, namely applying, spreading, positioning and re-positioning, as discussed hereinabove. In the context of the viscosity characteristic of the bioadhesive formulation presented hereinabove, the viscosity is relevant during the workable time, until crosslinking prevails and turns the formulation too viscous. The "bonding time" is defined as the time which elapses from the moment the formulation is applied on the object, to the moment at which the objects which are being bonded one to the other, are considered bonded at sufficient strength, so as to allow, for example, release of any fastening/tightening means (if used) and/or the continuation or completion of the procedure. The workable time and the bonding time may overlap to some extent, may continue one another respectively or may be discontinued, depending on the formulation, mode of its use as a single or multi-part formulation, the conditions of use and the objects' type and the bonding area.

According to some embodiments of the present invention, the workable time of the bioadhesive formulation presented herein, containing all ingredients mixed together, spans from 5 seconds to 30 minutes. Depending on the required and intended use of the formulation, it can be designed to exhibit various workable times which may span at least 30 seconds, at least 60 seconds, at least 120 seconds, at least 300 seconds, at least 600 seconds, at least 900 seconds, or at least 1800 seconds (30 minutes).

According to some embodiments of the present invention, the curing time of the bioadhesive formulation presented herein ranges from 5 seconds to 30 minutes.

Depending on the required and desired performance of the formulation, it can be designed to exhibit various curing times which may range from 5 to 30 seconds, from 5 to 30 seconds, from 5 to 60 seconds, from 5 to 120 seconds, from 10 to 300 seconds, from 30 to 300 seconds, and from 60 to 1800 seconds (30 minutes). Alternatively, in cases where the adhesion process is not restricted in time and other parameters such as strength and flexibility are more consequential, such as for example in topical (external) adhesion of a device to a patient's skin, the curing time may be longer than the aforementioned values, and can range from a few seconds to more than 30 minutes, and be, for example, 40 minutes, 50 minutes, 60 minutes, and even 120 minutes, including any intermediate value from 30 minutes and 120 minutes.

The Resulting Bioadhesive Matrix:

The bioadhesive matrix is a result of the curing process which takes place between some of the ingredients of the bioadhesive formulation, and hence the matrix comprises the gelatin and alginate, coupled to one another, as discussed herein, and optionally other constituents of the formulation which became associated with the matrix (e.g., entrapped therein).

As discussed hereinabove, the bioadhesive formulation as described herein is designed to form a corresponding bioadhesive matrix, and is hence designed such that the bioadhesive matrix exhibits a desired performance. According to some embodiments of the present invention, the bioadhesive formulation as described herein is designed such that upon its curing, it forms a bioadhesive matrix that is characterized by a high bonding strength of viable biological objects as defined herein, an optimal flexural modulus under physiological conditions, and an optimal biodegradability rate.

As used herein, the expression "optimal" relates to the performance of the formulation and/or corresponding matrix at a desired application. It is noted in this regard that different applications may require different parameters for an optimal performance, which may typically depend on the type of objects to be bonded, the dimensions of the objects to be bonded, the bonding area, the conditions the nature of the procedure calling for adhesion and other object- and procedure-dependent parameters.

While bonding strength of various viable tissues and other live or inanimate objects is a highly desired characteristic of a bioadhesive formulation/matrix, it is a non-trivial ability of the bioadhesive formulations presented herein to bond various objects, such as viable and non-viable tissues, bone, skin, metal, plastic and other natural and synthetic polymeric substances, under physiological conditions of mucus/plasma/blood wet environments.

The binding strength can be experimentally determined from the slope of a stress-strain curve created during tensile tests conducted on a sample of bonded objects, and expressed in units of force per unit area (Newton per square meter ($N/m^2$) or dynes per square centimeter), namely Pascals (Pa), megaPascals (MPa) or gigaPascals (GPa).

The phrase "bonding strength" as used herein describes the maximum amount of tensile stress that a pair of bonded objects of given materials can be subjected to before they break apart.

According to some embodiments of the present invention, the bioadhesive matrix afforded from the bioadhesive formulation presented herein is characterized by a maximal bonding strength of viable biological objects that ranges from about 2,000 pascal (2 MPa) to about 60,000 pascal (60 MPa) at peak bonding. According to some embodiments, the maximal bonding strength of viable biological objects, exhibited by the bioadhesive matrix presented herein ranges from 2 MPa to 10 MPa, from 5 MPa to 20 MPa, from 15 MPa to 30 MPa, from 20 MPa to 40 MPa, from 30 MPa to 50 MPa, or from 40 MPa to 60 MPa.

Another desired characteristic of the bioadhesive matrix, according to some embodiments of the present invention, is the extent of its capacity to bend and flex under stress and pressure without breaking or detaching from the objects it bonds, while being under physiological conditions, especially wet and swelled by absorbing water from the environment.

Depending on the intended use and conditions, the bioadhesive matrix is expected to perform (maintain its adhesive role in physiological conditions) over time and under intermittent or continuous motion, stress, deformation, bending, stretching, pressure and tear. According to some embodiments of the present invention, the matrix is characterized by a flexural strength (modulus) under physiological conditions that ranges from 0.5 MPa to 200 MPa. Alternatively, the flexural modulus under physiological conditions, exhibited by the bioadhesive matrix presented herein, ranges from 0.5 MPa to 5 MPa, from 1 MPa to 10 MPa, from 5 MPa to 20 MPa, from 10 MPa to 15 MPa, from 15 MPa to 20 MPa, from 20 MPa to 30 MPa, from 30 MPa to 50 MPa, from 50 MPa to 100 MPa, from 75 MPa to 150 MPa, from 100 MPa to 150 MPa, or from 155 MPa to 200 MPa.

According to some embodiments of the present invention, the bioadhesive matrix presented herein is biodegradable.

In order to be used effectively in various internal or external medical procedures and particularly in internal surgical procedures, the bioadhesive matrix presented herein further exhibits an optimal biodegradation rate, allowing it to bond the objects for a sufficient length of time so as to exhibit its intended use before disintegrating.

The term "biodegradable" and any adjective, conjugation and declination thereof as used herein, refers to a characteristic of a material to undergo chemical and/or physical transformation from a detectable solid, semi-solid, gel, mucus or otherwise a localized form, to a delocalized and/or undetectable form such as any soluble, washable, volatile, absorbable and/or resorbable breakdown products or metabolites thereof. A biodegradable material undergoes such transformation at physiological conditions due to the action of chemical, biological and/or physical factors, such as, for example, innate chemical bond lability, enzymatic breakdown processes, melting, dissolution and any combination thereof.

Depending on the chemical and physical characteristics of the bioadhesive matrix and the location of its application, and the intended use thereof, the process of biodegradation of the matrix can span days to weeks to months. The phrase "biodegradability rate" is defined herein as the period of time between application of a bioadhesive formulation to the time by which the resulting bioadhesive matrix is no longer present as a bioadhesive matrix. By being "no longer present" it is meant that substance(s) that can be attributed to the original matrix can no longer be detected at the site of application of the bioadhesive formulation at a substantial level, or that traces thereof which may still be detected in the original site beyond normal levels can no longer bond tissue or linger at that site.

In general, the bonding strength of the bioadhesive matrix, formed from the bioadhesive formulation presented herein, will start to degrade to some extent under physiological conditions. This degradation in strength is caused by the breakdown of the matrix, which is effected by a combination of factors, including chemical processes (swelling, dissolution and spontaneous chemical degradation), biological processes (enzymatically driven reactions, formation of new un-bonded cells and other tissue components and death of bonded cells and other tissue components), mechanical processes (stress, strain and tear) and the likes. For the sake of simplicity, the collection of factors and processes that degrade the bonding strength of the bioadhesive matrices presented herein are encompassed and unified under the phrase "biodegradability rate".

According to some embodiments of the present invention, the intended use of the bioadhesive formulation is to form a matrix that can hold biological objects attached to one-another for a time period long enough for the object to splice, fuse or heal. The period of time depends on the objects and on the medical procedure being performed.

For example, the formulation may be used to form a matrix that adjoins two edges of an incision strong and long enough to allow the incision to repair itself and heal; the incision may be in an internal site in the body or on the surface (skin and muscle). In another example, one of the objects is a patch of skin and the other object is an inanimate medical device, in which case the bioadhesive matrix is intended to hold the device affixed to the skin until it fulfills its purpose or until the matrix is replaced.

The biodegradability of the bioadhesive matrix can be manipulated by a combination of factors, starting at the composition, namely relative concentration of the polymers and the crosslinking density, additives that can alter the molecular structure of the matrix (more and varied cross-links), biodegradation accelerators/enhancers and biodegradation inhibitors/suppressors. Another factor that can be used to manipulate degradability is the macroscopic shape and structure of the matrix, namely its surface area, accessibility to the surrounding medium, size of the treated area and the likes.

Hence, according to some embodiments of the present invention, the biodegradability rate of the bioadhesive matrix presented herein ranges from about 7 days to about 6 months. In some cases the degradability period can be made shorter and range from 1 week to 1 month, including any time period in between, such as from 10 days to 3 weeks. In other cases, the degradability period can be made longer, e.g. 1-6 months, and range from 1 month to 2 months, from 2 month to 3 months or range from 2 months to 6 months.

Another parameter that can be used to determine the time factor involved in the bonding strength of any given bioadhesive matrix, including the matrix formed from the presently claimed bioadhesive formulation, is the half time of bonding strength retention, namely the period of time by which the maximal bonding strength reaches half its value, $T_{1/2}$.

According to some embodiments of the present invention, $T_{1/2}$ ranges from about 1 day to about 5 months and any value therebetween. For example, for short-adhesion period applications, $T_{1/2}$ ranges from about 1 week to about two weeks, or from about 10 days to about 1 month. For longer adhesion periods, $T_{1/2}$ ranges from about 1 month to about 2 months, or from about 2 months to about 3 months, or from about 3 months to about 4 months, or from about 3 months to about 5 months.

It should be noted herein that while a minimal bonding time and an optimal biodegradability rate are discussed, the bioadhesive matrix presented herein can be removed before it is biodegraded, and its bonding time can be shortened intentionally by mechanical and chemical means.

Concentrations of Basic Ingredients:

The present inventors have uncovered that at least some of the above-described characteristics of the bioadhesive formulation and the matrix formed therefrom can be manipulated by the relative concentrations of each of the ingredients of the bioadhesive formulation should be optimized.

According to some embodiments of the present invention, a bioadhesive formulation as described herein comprises gelatin, alginate and a coupling agent, as described herein, each being at a concentration that would impart the formulation with the herein-described characteristics and/or being at relative content ratio that would impart the formulation with the herein-described characteristics, as presented hereinbelow.

It is noted herein that for the bioadhesive formulation to be useful and effective, the concentration of its polymers is selected to afford a workable consistency (primarily in terms of viscosity). Therefore the high limit of the range of polymer concentration of workable formulations, and particularly that of gelatin, cannot exceed a certain value. Exceeding one or more of these maximal range values may result in an impracticable formulation.

According to some embodiments of the present invention, the concentration of gelatin in the formulation is 500 mg/ml or lower.

According to some embodiments of the present invention, the concentration of gelatin in the formulation ranges from 50 mg/ml to 500 mg/ml. In some embodiments, the gelatin content in the bioadhesive formulation ranges from 100 mg/ml to 500 mg/ml, from 100 mg/ml to 400 mg/ml, from 100 mg/ml to 300 mg/ml, from 100 mg/ml to 200 mg/ml, or from 50 mg/ml to 400 mg/ml, from 50 mg/ml to 300 mg/ml, from 50 mg/ml to 200 mg/ml or from 50 mg/ml to 100 mg/ml, including any value between the above-indicated values.

According to some embodiments of the present invention, the concentration of alginate in the formulation ranges from 5 mg/ml to 100 mg/ml. In some embodiments, the alginate content in the bioadhesive formulation ranges from 10 mg/ml to 100 mg/ml, from 10 mg/ml to 90 mg/ml, from 10 mg/ml to 80 mg/ml, from 10 mg/ml to 70 mg/ml, from 10 mg/ml to 60 mg/ml, from 10 mg/ml to 50 mg/ml, from 10 mg/ml to 40 mg/ml, or from 5 mg/ml to 90 mg/ml, from 5 mg/ml to 80 mg/ml, from 5 mg/ml to 70 mg/ml, from 5 mg/ml to 60 mg/ml, from 5 mg/ml to 50 mg/ml, from 5 mg/ml to 40 mg/ml, from 5 mg/ml to 30 mg/ml, from 5 mg/ml to 20 mg/ml, or from 5 mg/ml to 10 mg/ml, including any value between the above-indicated values.

According to some embodiments of the present invention, the concentration of the coupling agent in the formulation ranges from 1 mg/ml to 50 mg/ml, from 1 mg/ml to 40 mg/ml, from 1 mg/ml to 30 mg/ml, from 1 mg/ml to 20 mg/ml, or from 1 mg/ml to 10 mg/ml, including any value between the above-indicated values.

As discussed hereinabove, since some coupling agents are known as cytotoxic or as generating cytotoxic moieties, it is desired to use relatively low amount of the coupling agent within a bioadhesive formulation. On the other hand, reducing the amount of a coupling agent in the formulation may result in reducing the bonding strength of the bioadhesive matrix formed from the formulation. The present inventors have demonstrated that formulations containing 20-40 mg/ml or even lower amounts of a coupling agent can be used to provide bioadhesive matrices in which the bonding strength is not compromised substantially.

A few exemplary bioadhesive formulations are presented below, each comprising gelatin, alginate and a coupling agent at the indicated concentrations, given as percent by weight per volume of the total volume of the formulation:

Exemplary formulation I: 100 mg/ml gelatin; 20 mg/ml alginate and 4 mg/ml EDC as a carbodiimide-type coupling agent;

Exemplary formulation II: 100 mg/ml gelatin; 40 mg/ml alginate and 4 mg/ml EDC;

Exemplary formulation III: 100 mg/ml gelatin; 60 mg/ml alginate and 4 mg/ml EDC;

Exemplary formulation IV: 100 mg/ml gelatin; 40 mg/ml alginate and 10 mg/ml EDC;

Exemplary formulation V: 150 mg/ml gelatin; 40 mg/ml alginate and 10 mg/ml EDC;

Exemplary formulation VI: 200 mg/ml gelatin; 40 mg/ml alginate and 10 mg/ml EDC;

Exemplary formulation VII: 200 mg/ml gelatin; 40 mg/ml alginate and 5 mg/ml EDC;

Exemplary formulation VIII: 200 mg/ml gelatin; 70 mg/ml alginate and 35 mg/ml EDC;

Exemplary formulation IX: 250 mg/ml gelatin; 40 mg/ml alginate and 25 mg/ml EDC; or Exemplary formulation X: 200 mg/ml gelatin; 40 mg/ml alginate and 20 mg/ml EDC; or Exemplary formulation XI: 500 mg/ml gelatin; 10 mg/ml alginate and 25 mg/ml EDC.

It is noted herein that, in some embodiments of the present invention, the concentration of the coupling agent may be lowered by the presence of an additive, without compromising the formulation's performance.

For example, a bioadhesive formulation comprises gelatin, alginate, a coupling agent and a crosslinking promoting agent in the following amounts, given in weight per volume of the total volume of the formulation:

Exemplary formulation XII: 200 mg/ml gelatin; 40 mg/ml alginate, 10 mg/ml EDC and 2 mg/ml NHS-ester-type coupling agent (20% relative to EDC concentration);

Exemplary formulation XIII: 200 mg/ml gelatin; 40 mg/ml alginate, 10 mg/ml EDC and 4 mg/ml NHS-ester (40% relative to EDC concentration);

Exemplary formulation XIV: 200 mg/ml gelatin; 40 mg/ml alginate, 15 mg/ml EDC and 1.5 mg/ml NHS-ester (10% relative to EDC concentration);

Exemplary formulation XV: 200 mg/ml gelatin; 40 mg/ml alginate, 15 mg/ml EDC and 3 mg/ml NHS-ester (20% relative to EDC concentration);

Exemplary formulation XVI: 250 mg/ml gelatin; 30 mg/ml alginate, 20 mg/ml EDC and 4 mg/ml NHS-ester (20% relative to EDC concentration);

Exemplary formulation XVII: 500 mg/ml gelatin; 10 mg/ml alginate, 20 mg/ml EDC and 4 mg/ml NHS-ester (20% relative to EDC concentration); or Exemplary formulation XVIII: 300 mg/ml gelatin; 30 mg/ml alginate, 10 mg/ml EDC and 1 mg/ml NHS-ester (10% relative to EDC concentration).

It is noted herein that, in some embodiments of the present invention, the formulation may include a filler, without compromising the formulation's performance and even improving it and rendering it more suitable for use in a wider range of applications, such as hard tissue adhesion (bone adhesion etc.).

For example, a bioadhesive formulation comprises gelatin, alginate, a coupling agent, an optional crosslinking promoting agent and a filler in the following amounts:

Exemplary formulation XIX: 200 mg/ml gelatin; 40 mg/ml alginate, 20 mg/ml EDC and 0.25% w/v hydroxylapetite;

Exemplary formulation XX: 200 mg/ml gelatin; 40 mg/ml alginate, 20 mg/ml EDC and 0.5% w/v β-TCP;

Exemplary formulation XXI: 200 mg/ml gelatin; 40 mg/ml alginate, 10 mg/ml EDC and 0.5% w/v hydroxylapetite;

Exemplary formulation XXII: 200 mg/ml gelatin; 40 mg/ml alginate, 10 mg/ml EDC and 0.125% w/v β-TCP;

Exemplary formulation XXIII: 200 mg/ml gelatin; 40 mg/ml alginate, 20 mg/ml EDC, 2 mg/ml NHS-ester (10% relative to EDC concentration) and 0.25% w/v hydroxylapetite;

Exemplary formulation XXIV: 200 mg/ml gelatin; 40 mg/ml alginate, 20 mg/ml EDC, 4 mg/ml NHS-ester (20% relative to EDC concentration) and 0.5% w/v β-TCP;

Exemplary formulation XXV: 300 mg/ml gelatin; 30 mg/ml alginate, 10 mg/ml EDC, 1 mg/ml NHS-ester (10% relative to EDC concentration) and 0.5% w/v hydroxylapetite; or Exemplary formulation XXVI: 300 mg/ml gelatin; 30 mg/ml alginate, 10 mg/ml EDC, 1 mg/ml NHS-ester (10% relative to EDC concentration) and 0.125% w/v β-TCP.

Thus, in some embodiments, a bioadhesive formulation as described herein, comprises alginate, gelatin, water, and a coupling agent, as described herein, and further comprises a cross-linking promoting agent and/or a filler, as described herein, wherein the concentration of the coupling agent is 20 mg/ml or lower (e.g., 15 mg/ml, or 10 mg/ml, or lower).

Any of the aforementioned exemplary formulation may further include one or more bioactive agents as described herein.

It is noted herein that other combinations of component concentrations are contemplated, some of which have been demonstrated in the Examples section that follows.

Drug-Eluting Bioadhesive Formulations:

According to some embodiments of the present invention, a bioadhesive formulation as described herein further comprises one or more bioactive agent(s). In some embodiments, such a formulation is designed to afford a drug-eluting bioadhesive matrix upon curing. In other words, bioadhesive formulations which contain a bioactive agent, cure to form a drug-eluting bioadhesive matrix in which the bioactive agent is incorporated. In some embodiments, such drug-eluting bioadhesive matrices are formed such that the bioactive agent is released from the matrix upon contacting the matrix with a physiological medium. Thus, the bioadhesive formulations, according to some embodiments of the present invention, can be used for various bioadhesion applications, as discussed herein, while at the same time serving as a reservoir and vehicle for delivering a bioactive agent.

It is noted herein that while the incorporation of a bioactive agent in the formulation may affect the characteristics of the formulation and the characteristics of the resulting bioadhesive matrix, the bioadhesive formulation and its corresponding matrix are designed to possess the desired properties presented hereinabove while adding the capacity of eluting bioactive agent(s) as discussed hereinbelow.

It is further noted herein that according to some embodiments of the present invention, the bioadhesive formulation and the corresponding matrix containing no bioactive agent, is meant for use primarily for its bioadhesive properties. In such embodiments, other that the amount and rate of releasing a bioactive agent, all other characteristics and traits of an effective bioadhesive formulation/matrix described herein, as well as the optimal relative contents of the main constituents, apply for a formulation not including a bioactive agent therein.

The term "incorporated", as used in the context of a bioactive agent and the bioadhesive formulation/matrix according to some embodiments of the present invention, is used synonymously with terms such as "sequestered", "loaded", "encapsulated", "associated with", "charged" and any inflection of these terms, all of which are used interchangeably to describe the presence of the bioactive agent, as defined hereinbelow, within the formulation/matrix. A sequestered bioactive agent can elute or be released from the matrix via, for example, diffusion, dissolution, elution, extraction, leaching, as a result of any or combination of wetting, swelling, dissolution, chemical breakdown, degradation, biodegradation, enzymatic decomposition and other processes that affect the matrix. A bioactive agent may also elute from the matrix without any significant change to the matrix' structure, or with partial change.

As used herein, the phrase "bioactive agent" describes a molecule, compound, complex, adduct and/or composite that exerts one or more biological and/or pharmaceutical activities. The bioactive agent can thus be used, for example, to relieve pain, prevent inflammation, prevent and/or reduce and/or eradicate an infection, promote wound healing, promote tissue regeneration, effect tumor/metastasis eradication/suppression, effect local immune-system suppression, and/or to prevent, ameliorate or treat various medical conditions.

"Bioactive agents", "pharmaceutically active agents", "pharmaceutically active materials", "pharmaceuticals", "therapeutic active agents", "biologically active agents", "therapeutic agents", "medicine", "medicament", "drugs" and other related terms may be used herein interchangeably, and all of which are meant to be encompassed by the term "bioactive agent".

The term "bioactive agent" in the context of the present invention also includes diagnostic agents, including, for example, chromogenic, fluorescent, luminescent, phosphorescent agents used for marking, tracing, imaging and identifying various biological elements such as small and macromolecules, cells, tissue and organs; as well as radioactive materials which can serve for both radiotherapy and tracing, for destroying harmful tissues such as tumors/metastases in the local area, or to inhibit growth of healthy tissues, such as in current stent applications; or as biomarkers for use in nuclear medicine and radio-imaging.

Bioactive agents useful in accordance with the present invention may be used singly or in combination, namely more than one type of bioactive agents may be used together in one bioadhesive formulation, and therefore be released simultaneously from the bioadhesive matrix.

In some embodiments, the concentration of a bioactive agent in the formulation ranges from 0.1 percents weight per volume to 10 percents weight per volume of the total volume of said formulation, and even more in some embodiments. Higher and lower values of the content of the bioactive agent ate also contemplated, depending on the nature of the bioactive agent used and the intended use of the bioadhesive formulation/matrix.

When using the term "bioactive agent" in the context of releasing or eluting a bioactive agent, it is meant that the bioactive agent is substantially active upon its release.

As discussed hereinbelow, the bioactive agent may have an influence on the coupled gelatin-alginate matrix chemical and/or mechanical properties by virtue of its own reactivity with one or more of the matrix-forming components and/or the coupling agent, or by virtue of its chemical and/or physical properties per-se. It is therefore noted that in general, the bioactive agent is selected suitable for being incorporated into the bioadhesive formulation which affords the coupled gelatin gelatin-alginate bioadhesive matrix such that it can elute from the bioadhesive matrix in the intended effective amount and release rate, while allowing the pre-curing bioadhesive formulation to exhibit desired properties, as discussed herein, and while allowing the formulation to afford a bioadhesive matrix that exhibits the desired properties, as discussed herein.

As discussed and exemplified in the Examples section that follows, some bioactive agents may exhibit one or more functional groups which may be susceptible to the coupling processes taking place between the polymers and the coupling agent, and may therefore influence the characteristics of the resulting matrix. For example, bioactive agents exhibiting a carboxylic group or a primary amine group may react with a coupling agent which is selected for its reactivity towards such functional groups. In such cases, in order to maintain desirable characteristics of the resulting matrix, some adjustments may be introduced to the bioadhesive formulation in terms of the type of ingredients and their concentrations.

A bioactive agent, according to some embodiments of the present invention, can be, for example, a macro-biomolecule or a small, organic molecule.

According to some embodiments of the present invention, the bioactive agent is a non-proteinous substance, namely a substance possessing no more than four amino acid residues in its structure.

According to some embodiments of the present invention, the bioactive agent is a non-carbohydrate substance, namely a substance possessing no more than four sugar (aminoglycoside inclusive) moieties in its structure.

According to some embodiments of the present invention, the bioactive agent is substantially devoid of one or more of the following functional groups: a carboxyl, a primary amine, a hydroxyl, a sulfhydroxyl and an aldehyde.

The term "macro-biomolecules" as used herein, refers to a polymeric biochemical substance, or biopolymers, that occur naturally in living organisms. Amino acids and nucleic acids are some of the most important building blocks of polymeric macro-biomolecules, therefore macro-biomolecules are typically comprised of one or more chains of polymerized amino acids, polymerized nucleic acids, polymerized saccharides, polymerized lipids and combinations thereof. Macromolecules may comprise a complex of several macromolecular subunits which may be covalently or non-covalently attached to one another. Hence, a ribosome, a cell organelle and even an intact virus can be regarded as a macro-biomolecule.

A macro-biomolecule, as used herein, has a molecular weight higher than 1000 dalton (Da), and can be higher than 3000 Da, higher than 5000 Da, higher than 10 kDa and even higher than 50 KDa.

Representative examples of macro-biomolecules, which can be beneficially incorporated in the bioadhesive drug-eluting matrices described herein include, without limitation, peptides, polypeptides, proteins, enzymes, antibodies, oligonucleotides and labeled oligonucleotides, nucleic acid constructs, DNA, RNA, antisense, polysaccharides, viruses and any combination thereof, as well as cells, including intact cells or other sub-cellular components and cell fragments.

As used herein, the phrase "small organic molecule" or "small organic compound" refers to small compounds which consist primarily of carbon and hydrogen, along with nitrogen, oxygen, phosphorus and sulfur and other elements at a lower rate of occurrence. In the context of the present invention, the term "small" with respect to a compound, agent or molecule, refers to a molecular weight lower than about 1000 grams per mole. Hence, a small organic molecule has a molecular weight lower than 1000 Da, lower than 500 Da, lower than 300 Da, or lower than 100 Da.

Representative examples of small organic molecules, that can be beneficially incorporated in the bioadhesive drug-eluting matrices described herein include, without limitation, angiogenesis-promoters, cytokines, chemokines, chemo-attractants, chemo-repellants, drugs, agonists, amino acids, antagonists, anti histamines, antibiotics, antigens, antidepressants, anti-hypertensive agents, analgesic and anesthetic agents, anti-inflammatory agents, antioxidants, anti-proliferative agents, immunosuppressive agents, clotting factors, osseointegration agents, anti-viral agents, chemotherapeutic agents, co-factors, fatty acids, growth factors, haptens, hormones, inhibitors, ligands, saccharides, radioisotopes, radiopharmaceuticals, steroids, toxins, vitamins, minerals and any combination thereof.

Representative examples of bioactive agents suitable for use in the context of the present embodiments include, without limitation, analgesic, anesthetic agents, antibiotics, antitumor and chemotherapy agents, agonists and antagonists agents, amino acids, angiogenesis-promoters, anorexics, antiallergics, antiarthritics, antiasthmatic agents, antibodies, anticholinergics, anticonvulsants, antidepressants, antidiabetic agents, antidiarrheals, antifungals, antigens, antihistamines, antihypertensive agents, antiinflammatory agents, antimigraine agents, antinauseants, antineoplastics, antioxidants, antiparkinsonism drugs, antiproliferative agents, antiprotozoans, antipruritics, antipsychotics, antipyretics, antisenses nucleic acid constructs, antispasmodics, antiviral agents, bile acids, calcium channel blockers, cardiovascular preparations, cells, central nervous system stimulants, chemo-attractants, chemokines, chemo-repellants, chemotherapeutic agents, cholesterol, co-factors, contraceptives, cytokines, decongestants, diuretics, DNA, Drugs and therapeutic agents, enzyme inhibitors, enzymes, fatty acids, glycolipids, growth factors, growth hormones, haemostatic and antihemorrhagic agents, haptens, hormone inhibitors, hormones, hypnotics, immunoactive agents, immunosuppressive agents, inhibitors and ligands, labeled oligonucleotides, microbicides, muscle relaxants, nucleic acid constructs, oligonucleotides, parasympatholytics, peptides, peripheral and cerebral vasodilators, phospholipids, polysaccharides, proteins, psychostimulants, radioisotopes, radiopharmaceuticals, receptor agonists, RNA, saccharides, saponins, sedatives, small organic molecules, spermicides, steroids, sympathomimetics, toxins, tranquilizers, vaccines, vasodilating agents, viral components, viral vectors, viruses, vitamins, and any combination thereof.

The bioactive agent may be selected to achieve either a local or a systemic response. The bioactive agent may be any prophylactic agent or therapeutic agent suitable for various topical, enteral and parenteral types of administration routes including, but not limited to sub- or trans-cutaneous, intradermal transdermal, transmucosal, intramuscular administration and mucosal administration.

One class of bioactive agents which can be encapsulated in the bioadhesive drug-eluting matrices, according to some embodiments of the present invention, is the class of analgesic agents that alleviate pain e.g. NSAIDs, COX-2 inhibitors, opiates and morphinomimetics.

Another class of bioactive agents which can be incorporated in the bioadhesive drug-eluting matrices, according to some embodiments of the present invention, is the class of anesthetic agents. Another class of bioactive agents which can be incorporated in the bioadhesive drug-eluting matrices, according to some embodiments of the present invention, is the class of therapeutic agents that promote angiogenesis. Non-limiting examples include growth factors, cytokines, chemokines, steroids cell survival and proliferation agents.

Another class of bioactive agents which can be incorporated into the bioadhesive drug-eluting matrices, according to some embodiments of the present invention, especially in certain embodiments wherein tissue regeneration is desirable, and application involving implantable devices and tissue healing, are cytokines, chemokines and related factors.

Non-limiting examples of immunosuppressive drugs or agents, commonly referred to herein as immunosuppressants, include glucocorticoids, cytostatics, antibodies, drugs acting on immunophilins and other immunosuppressants.

Non-limiting examples of haemostatic agents include kaolin, smectite and tranexamic acid.

It is noted herein that kaolin is an exemplary bioactive agent which has a limited solubility in the bioadhesive formulation, and is therefore added in the form of a dry powder, and thus acts, at least to some extent, also as a filler in the bioadhesive formulation. This dual function, bioactive agent and filler, may characterize any additive or bioactive agent which are encompassed by embodiments of the present invention and are contemplated therewith.

Additional bioactive agents which can be beneficially incorporated in the bioadhesive drug-eluting matrices, according to some embodiments of the present invention, include cytotoxic factors or cell cycle inhibitors and other agents useful for interfering with cell proliferation.

Additional bioactive agents which can be beneficially incorporated into the bioadhesive drug-eluting matrices, according to some embodiments of the present invention, include genetic therapeutic agents and proteins, such as ribozymes, anti-sense polynucleotides and polynucleotides coding for a specific product (including recombinant nucleic acids) such as genomic DNA, cDNA, or RNA. The polynucleotide can be provided in "naked" form or in connection with vector systems that enhances uptake and expression of polynucleotides. These can include DNA compacting agents (such as histones), non-infectious vectors (such as plasmids, lipids, liposomes, cationic polymers and cationic lipids) and viral vectors such as viruses and virus-like particles (i.e., synthetic particles made to act like viruses). The vector may further have attached peptide targeting sequences, anti-sense nucleic acids (DNA and RNA), and DNA chimeras which include gene sequences encoding for ferry proteins such as membrane translocating sequences ("MTS"), tRNA or rRNA to replace defective or deficient endogenous molecules and herpes simplex virus-1 ("VP22").

Additional bioactive agents which can be beneficially incorporated in the bioadhesive drug-eluting matrices, according to some embodiments of the present invention, include gene delivery agents, which may be either endogenously or exogenously controlled.

Additional bioactive agents which can be beneficially incorporated into the bioadhesive drug-eluting matrices, according to some embodiments of the present invention, include the family of bone morphogenic proteins ("BMP's") as dimers, homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Additional bioactive agents which can be beneficially incorporated into the bioadhesive drug-eluting matrices, according to some embodiments of the present invention, include chemotherapeutic agents.

Additional bioactive agents which can be beneficially incorporated into the bioadhesive drug-eluting matrices, according to some embodiments of the present invention, include antibiotic agents.

Antiviral agents may include nucleoside phosphonates and other nucleoside analogs, AICAR (5-amino-4-imidazolecarboxamide ribonucleotide) analogs, glycolytic pathway inhibitors, glycerides, anionic polymers, and the like.

Additional bioactive agents which can be beneficially incorporated into the bioadhesive drug-eluting matrices, according to some embodiments of the present invention, include viral and non-viral vectors.

Additional bioactive agents which can be beneficially incorporated into the bioadhesive drug-eluting matrices, according to some embodiments of the present invention, include steroidal anti-inflammatory drugs.

Additional bioactive agents which can be beneficially incorporated into the bioadhesive drug-eluting matrices, according to some embodiments of the present invention, include anti-oxidants.

Additional bioactive agents which can be beneficially incorporated into the bioadhesive drug-eluting matrices, according to some embodiments of the present invention, include vitamins.

Additional bioactive agents which can be beneficially incorporated into the bioadhesive drug-eluting matrices, according to some embodiments of the present invention, include hormones.

Additional bioactive agents which can be beneficially incorporated into the bioadhesive drug-eluting matrices, according to some embodiments of the present invention, include cells of human origin (autologous or allogeneic), including stem cells, or from an animal source (xenogeneic), which can be genetically engineered if desired to deliver proteins of interest.

Drug Release Profile:

The rate of release of the bioactive agent, or the drug release profile from the matrix, serving as its reservoir, can be controlled by various factors, such as the relative concentrations of the constituents in the bioadhesive formulation described herein.

A typical drug delivery mechanism, relevant in the context of the present embodiments, consists of a reservoir containing a predetermined and exhaustible amount of the drug, and an interface between the drug's reservoir and the physiological environment. Typically, the drug release commences at the initial time point when the reservoir is exposed to the physiological environment, and follows typical diffusion-controlled kinetics with additional influences effected by water uptake (swelling), disintegration and biodegradation of the matrix and the likes.

It is noted that contrary to synthetic polymers that are used in the formulation that affords other drug-eluting matrices, such as poly-lactic acid (PLA) and poly-glycolic acid (PGA), the gelatin-alginate coupled matrix is not water degradable, neither the natural polymers, nor the coupling product amide bond. In a live subject body this matrix will pass degradation through enzymatic activity, which would further affect the drug release rate.

A "drug release profile" is a general expression which describes the temporal concentration of a drug (a bioactive agent) as measured in a particular bodily site of interest as a function of time, while the slope of a concentration versus time represents the rate of release at any given time point. A drug release profile may be sectioned into rate dependent periods whereby the rate is rising or declining linearly or exponentially, or staying substantially constant. Some of the typically sought rates include the burst release rate and the sustained release rate.

The phase "burst release", as used herein, is consistent with a rapid release of a drug into the bodily site of interest, and is typically associated with an exponential increase of the drug's concentration, growing from zero to a high level at a relatively short time. Typically, the burst release section of the drug release profile ends briefly and then gradually changes to a plateau, or a sustained release section in the release profile.

The phrase "sustained release", as used herein, refers to the section of the drug release profile which comes after the burst release part, and is typically characterized by constant rate and relative long duration.

The main differences between the burst and the sustain parts of a release profile are therefore the rate (slope characteristics) and duration, being exponential and short for the burst release, and linear and long for the sustained release; and both play a significant role in drug administration regimes. In most cases, the presence of both a burst release section and a sustained release section is unavoidable and stems from chemical and thermodynamic properties of the drug delivery mechanism.

In the context of embodiments of the present invention, the phrase "high burst release" is an attribute of a drug-eluting bioadhesive matrix, as described herein, which refers to the amount of drug that is being released from the matrix during the initial stage of exposure of the matrix to the environment of its action (e.g., physiological environment), wherein the amount is in excess of 20% of the total amount contained in the matrix and the initial stage is regarded as the first six hours from exposure.

In some embodiments of the present invention, "high burst release" describes an attribute of a drug-eluting bioadhesive matrix, as described herein, in which 30%, 40%, 50%, 60% and even higher percentages of the bioactive agent (drug) are released during the first 6 hours of exposing the matrix to a physiological medium. Any value between 20% and 100% of the bioactive agent (drug) are contemplated.

Accordingly, the phrase "low burst release" refers to drug-eluting bioadhesive matrices wherein less than 20% of the contained drug is released within the first six hours of exposure.

In some embodiments of the present invention, "low burst release" describes an attribute of a drug-eluting bioadhesive matrix, as described herein, in which 15%, 10%, 5% and even lower percentages of the bioactive agent (drug) are released during the first 6 hours of exposing the matrix to a physiological medium. Any value between 20% and 1% of the bioactive agent (drug) are contemplated.

In general, and according to some embodiments of the present invention, at least 20 percents of the bioactive agent are released to the surrounding physiological medium within 6 hours of contacting the formulation/matrix with physiological medium.

According to some other embodiments of the present invention, no more than 20 percents of the bioactive agent are released to the surrounding physiological medium within 6 hours of contacting the formulation/matrix with physiological medium.

Preparation of the Bioadhesive Formulation and Matrix Formation:

The bioadhesive formulations presented herein, either containing or not containing a bioactive agent, are prepared by mixing all the ingredients together into a single concoction, at least in the sense of the formulation which is capable of curing.

The single concoction can be formed ex vivo, in vitro or in situ, namely the formulation can be in the form of two or more sub-formulations kept separately, or as a set of dry powders and a pre-measured amount of solvent (water) kept separately, as discussed hereinbelow, which are combined to form the single concoction by one of the following manners.

In vitro means that the formulation as a single concoction is formed by mixing (e.g., in a vial) all the components of the formulation, as these are defined, described and exemplified herein, prior to applying the formulation onto the object(s) to be bonded.

In situ means that the formulation as a single concoction is formed by applying one sub-formulation on one object, and another sub-formulation on another object, and adjoining the objects together to form the single concoction at the site of adhesion; or by applying one sub-formulation on an object and thereafter applying another sub-formulation on the same object.

When applied to animated objects, in vitro corresponds to ex vivo, and in situ corresponds to in vivo.

In any eventuality, the formulation is kept under conditions where it is substantially unable to cure.

According to an aspect of some embodiments of the resent invention, there is provided a method of forming a bioadhesive matrix, which is effected by curing the bioadhesive formulation as described herein.

As used herein, the term "curing" includes an active procedure such as subjecting the formulation to certain conditions (e.g., heating and/or mixing, shear forces, etc.), as well as a passive procedure, which involved allowing the curing time to elapse.

In some embodiments, the method further comprises, prior to the curing, mixing the components of the formulation, namely, mixing the herein-described sub-formulations or mixing the herein-described powder(s) with the appropriate solvent(s).

As discussed hereinabove, the mixing can be effected ex vivo, in vivo, in vitro or in situ.

Use of the Bioadhesive Formulations and Matrices:

As discussed herein, the bioadhesive formulations presented herein, either containing or not containing a bioactive agent, are used to form a bioadhesive matrix, being either a drug-eluting or non-drug-eluting matrix, which is useful in many medical and paramedical applications. As discussed above, the bioadhesive matrices, according to some embodiments of the present invention, are useful, for example, in replacing or reinforcing surgical sutures and staples.

Hence, according to some embodiments, the formulations presented herein, either incorporating a bioactive agent or not, are identified for use in bonding objects to one another, wherein at least one of these objects is a biological object, as these terms are defined and discussed herein.

In general, the bioadhesive formulation presented herein can be used in the manufacturing of a product intended for bonding objects, at least one of which is a biological object.

Thus, the phrase "biological object", as used herein, refers to any viable/live part of an animal or plant, including a single live animal specimen. A live or viable biological object or tissue is defined as any major or minor part of a plant or animal that is still viable or alive and substantially kept in a physiological environment in order to stay viable or alive. Non-limiting examples of biological objects include any plant or animal, viable tissue samples, skin tissue, bone tissue, connective tissue, muscle tissue, nervous tissue and epithelial tissue. Also encompassed are edges of incisions made in an organ, such as skin, muscle, internal organ in any bodily site of an organism.

Inanimate objects are objects which cannot be revived, grafted, proliferate or otherwise show any signs of life as defined medically, and include objects of synthetic and/or biological origins. These include, for example, patches, bone-replacement parts, pace makers, ports and vents and any other medical device that required affixing and immobilization to a viable biological object as defined herein.

According to some embodiments of the present invention, inanimate biological objects can be made partially or entirely from animal or plant materials and products, or partially or entirely from synthetic substances. While the bioadhesive formulation is designed for use in or on viable biological objects, it is noted herein that is can be used effectively to bond biologic or synthetic inanimate objects like any adhesion agent or glue.

It is noted herein that the term "object" is meant to encompass one or more parts or portions of the same object, thus closing an incision by bonding the two sides of the incision in a tissue or an organ, by using the herein-described formulation, can be regarded as either bonding one object (the tissue or organ) or two objects (the two sides of the incision).

According to some embodiments, the drug-eluting matrix, resulting from a bioadhesive formulation which incorporates a bioactive agent, is used solely for its drug-eluting and drug-delivery faculties regardless of its bioadhesive faculty. Such a matrix can serve, for example, as a drug depot, and can be adhered to an organ or tissue where the release of the drug is beneficial (without bonding thereto another object).

Methods of Forming Bioadhesive Matrices and Bonding Objects:

According to an aspect of embodiments of the present invention, there is provided a method of forming the herein-described bioadhesive matrix using the herein-described bioadhesive formulation, the method is effected by curing the formulation.

According to some embodiments of the present invention, the bioadhesive matrix, being formed by curing a bioadhesive formulation, containing a bioactive agent or not, is formed on an object and/or between two or more objects, wherein at least one of the objects is a biological object as described herein.

The formation of the herein-described bioadhesive matrix on an object is effected by applying the herein-described bioadhesive formulation on the object and curing the formulation. The formation of the matrix between two or more objects is effected by applying the formulation on one or more of the objects, for example, on the parts of their surface that is intended for bonding, and thereafter adjoining the objects. By adjoining the objects it is meant that at least parts of the surface of each object are put in contact.

In some embodiments of the invention, adjoining the object is further accompanied by using force and/or other means of fastening the objects and keep the objects adjoined (prevent the bonded surfaces from separating) one to the other at least until the formulation cures to such extent that the object are bonded and can be let go.

Accordingly, there is provided a method of bonding at least two objects to one another, which is effected by:

applying the bioadhesive formulation presented herein onto at least one of the objects; and adjoining the objects (so as to form a contact therebetween), optionally while fastening the object to one another.

It is noted that the action of adjoining is effected so as to form contact between the object, while fastening is used in order to allow the formulation to cure and form the matrix between the objects, thereby bonding the objects to one-another.

According to some embodiments of the present invention, the bioadhesive formulations and matrices presented herein can be used to hold body tissues together after an injury or surgery, as well as in many surgical procedures including, but not limited to incision closure, corneal perforations, episiotomy, caesarian cases, cleft lip, skin and bone grafting, tendon repair, hernia, thyroid surgery, periodontal surgery, gingivectomy, dental implants, oral ulcerations, gastric varices wounds of internal organs such as liver and pancreas, attachment and immobilization of external and internal medical devices and more.

Means for Storing, Preparing and Applying Bioadhesive Formulations:

As presented herein, the bioadhesive formulation according to some embodiments of the present invention consists of two or more major polymeric components and a coupling agent that forms crosslinking bonds between the major polymeric components. Since the coupling/crosslinking reaction occurs upon contacting the polymeric components with the coupling agents, these two groups of components, namely the polymers and the coupling agents, should be kept separated until there is a need to apply the formulation. It is therefore noted that the formulation can be kept in any number of separated parts, at least until it is being mixed into a single concoction comprising all ingredients prior to its application and use.

Hence, according to some embodiments of the present invention, the pre-curing bioadhesive formulation presented herein is formed by contacting a sub-formulation A that contains primarily gelatin, alginate and an optional bioactive agent, with a sub-formulation B contains primarily one or more coupling agents.

Alternatively, the pre-curing bioadhesive formulation can be kept indefinitely as dry mixture of powders of pre-measured amounts of each of its constituents, including the polymers, the coupling agents, various additives and the bioactive agents, permitting each can be reconstituted by dissolution in water. Alternatively only some of the constituents are kept as dry mixture of powers while other constituents are kept as separate solutions or powders. It is noted that any form of long-term storage of the bioadhesive formulation is contemplated as long as the coupling/crosslinking reaction is prevented from commencing uncontrollably.

Alternatively, according to some embodiments of the present invention, sub-formulation A and sub-formulation B are each kept in sealed compartments, each compartment may serve as a storage vessel, or as a reservoir of an integrated applicator (e.g., configured for applying pastes and thick liquids) adapted for applying the bioadhesive formulation presented herein.

Hence, according to another aspect of some embodiments of the present invention, there is provided a kit for storing, preparing and/or applying the pre-curing bioadhesive formulation presented herein, which includes at least two compartments, such as a first compartment and a second compartment, wherein the first compartment contains sub-formulation A, as presented hereinabove, and the second compartment contains sub-formulation B. As long as these two compartments are kept sealed and under acceptable storage conditions, the bioadhesive formulation will not cure or disintegrate.

In some embodiments, the kit includes at least two compartments, each containing the constituents corresponding to the particular sub-formulation, which have been pre-dissolved in a solvent to a specific concentration such that mixing the two sub-formulations results in a bioadhesive formulation as described herein.

Alternatively, the kit includes one or more compartments, each containing a pre-measured amount of a dry powder of one or more constituent of the bioadhesive formulation, and a separate compartment containing a pre-measured amount of the solvent, such that mixing the powder(s) and the solvent results in a bioadhesive formulation as described herein.

The kit may further include mixing and stirring tools, bowls, applicators, freshness indicators, tamper-proof measures and printed matter for instructions for the user.

The kit may include a device, an applicator or a dispenser for expelling measured amounts of each sub-formulation controllably and optionally synchronously, each of which is dispensed from the individual compartment serving as a cartridge of the individual sub-formulation.

Hence, according to another aspect of some embodiments of the present invention, there is provided an integrated dual chamber dispenser for use in applying the bioadhesive formulation presented herein, which includes a dual barrel cartridge assembly with a joint delivery port with a mount therein for coupling with a mixing tube. Integrated applicators suitable for applying the bioadhesive formulation presented herein, may follow the design of any applicator for two-part chemistry adhesives which require efficient dispensing under controlled and safe conditions of two sub-formulations from separate compartments.

Exemplary two-part chemistry adhesive applicators, which can be used to mix, dispense and apply the bioadhesive formulations presented herein are disclosed, for example, in U.S. Patent Application Publication Nos. 2007/0289996 and 2011/0248045, and in U.S. Pat. Nos. 4,979,942, 5,082,147, 6,732,887, 7,530,808, 7,635,343, 7,699,803, 8,074,843, all of which are incorporated herein by reference as if full set forth herein.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the formulation, composition, method, matrix or structure may include additional ingredients, steps and/or parts, but only if the additional ingredients, steps and/or parts do not materially alter the basic and novel characteristics of the claimed formulation, composition, method, matrix or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Materials and Methods

Materials:

An exemplary basic bioadhesive matrix, according to some embodiments of the present invention, was prepared from an exemplary bioadhesive formulation containing the following ingredients:

Gelatin—In the example presented herein gelatin type A from porcine skin (90-100 bloom) was purchased from Sigma-Aldrich. For the adhesive mechanism studies, three types of gelatin "type A" from porcine skin with different Bloom numbers (90-100, 175 and 300) were used.

Alginate—In the example presented herein alginic acid sodium salt (viscosity about 250 cps, 2% (25° C.) was purchased from Sigma-Aldrich. For the adhesive mechanism studies, alginic acid sodium salts with low (LV) and high viscosity (HV) of 100-300 cP (0.1-0.3 Pa-sec) and more than 2,000 cP (2 Pa-sec), 2% (25° C.) respectively were used.

EDC—N-(3-Dimethylaminopropyl)-N'-ethylcarbodiimide hydrochloride was purchased from Sigma-Aldrich.

Bupivacaine hydrochloride was purchased from Sigma-Aldrich. It is a local anesthetic used for peripheral nerve block, infiltration, and sympathetic, caudal or epidural block.

Ibuprofen sodium salt was purchased from Sigma-Aldrich. It—is a commonly used non-steroidal anti-inflammatory drug used in the treatment of pain, fever, dysmenorrhea, osteoarthritis, rheumatoid arthritis, and other rheumatic and nonrheumatic inflammatory disorders, and vascular headaches.

Synthetic hydroxylapatite (also called hydroxyapatite, HA), in the form of a powder) and beta-tricalcium phosphate (β-TCP) in the form of sintered powder, were purchased from Sigma-Aldrich, Rehovot, Israel.

Bioadhesive Preparation:

Drug-eluting bioadhesive preparation is generally based on dissolving various amounts of gelatin, alginate and a bioactive agent as powders or stock solutions in distilled water, under heating condition of up to 60° C. on a hot plate. Due to the high viscosity of the final solution, stirring is effected by an agitator such as Fisher's Vortex Genuine 2™ stirring device.

Briefly, a pre-measured amount of a bioactive agent is dissolved in distilled water. Thereafter a pre-measured amount of alginate is added into the clear and transparent homogenous solution of the bioactive agent. Once a bright yellow homogenous viscous solution is afforded, a pre-measured amount of gelatin i added thereto to afford a gelatin-alginate-active agent mixture, also referred to herein as sub-formulation A. Various pre-measured amounts of the coupling agent EDC are dissolved in a separate distilled water tube to afford sub-formulation B, which is added to sub-formulation A just prior to the time of bioadhesive use.

Pristine bioadhesive matrices not sequestering any bioactive agent are prepared from a bioadhesive formulation without a bioactive agent, similarly to the procedure above with the exception that alginate is first dissolved in pure distilled water.

Viscosity Measurements:

Since the initial viscosity of the bioadhesive formulation is affected mainly by the viscosity of the gelatin-alginate solution, viscosity measurements were conducted prior to the addition of EDC. The viscosity measurements were performed using a controlled stress rheometer (model AR2000, TA Instruments Ltd.), fitted with a cone-and-plate geometry (4° cone angle, 40 mm diameter, 400 μm gap), at a constant temperature of 37° C. and a constant shear rate of 10 Hz in order to investigate the relations between the adhesive's initial viscosity and its bonding strength.

Soft Tissue Bonding Strength Measurements:

In vitro soft tissue bonding strength measurements of various bioadhesive matrices, according to some embodiments of the present invention, were performed in order to examine the effect of the bioactive agent's type and concentration in the bioadhesive formulation on the bonding strength, namely, the ability to bind two soft tissue samples together.

Porcine skin (purchased from Kibbutz Lahav, Israel) was used as soft-tissue model for the bonding test. The porcine skin was cut into 2 cm×2 cm square-shape pieces, using a scalpel, and the pieces were kept in −20° C. until use. At time of use, the porcine skin pieces were thawed in air and their epidermis side was attached firmly with super-glue to 1 cm height brass testing holders with a matching surface area. The testing holders were connected to brass grip tabs of 2 cm×0.4 cm×5 cm.

0.1 ml of sub-formulation A (the gelatin-alginate mixture) was spread uniformly and equally on the dermis side of two porcine skin pieces having their epidermis side attached to the testing holders, as presented hereinabove. Thereafter, 0.04 ml of sub-formulation B (EDC solution) was mixed with sub-formulation A on one of the skin pieces to afford a pre-curing bioadhesive formulation, which turns into a bio-adhesive matrix once cured. Subsequently, the holder attached to the other piece was placed above the first holder, in a way that a firm contact was established between the dermis sides of the both skin pieces. The two holders were then pressed together in a constant force of 1.25 N and were placed in a static incubator (Heraeus, B12) at 37° C. and 100% humidity environment for 30 minutes. Five identical coupled skin samples were prepared using each tested bioadhesive formulation.

After 30 minutes of incubation, the bonding strength of the bioadhesive matrix was measured in tension at room temperature using a 5500 Instron Universal Testing Machine (Instron engineering Corp.) and a 10 N load cell. The two holder adjoined by the coupled skin pieces were strained under constant velocity of 2 mm/min until separation was achieved and the result was recorded in kilo-pascal (KPa). The mechanical testing procedure was inspired by standard test method ASTM F-2258-03. The boning strength was defined as the maximum strength in the stress-strain curve, measured by the Instron Merlin software.

Drug-Eluting Studies:

In vitro release studies were preformed in order to examine the effect of the bioadhesive components on the release kinetics of two types of bioactive agents in the form of the anesthetic drugs bupivacaine and ibuprofen. Five repetitions were carried out for each formulation.

0.1 ml of the tested sub-formulation A (gelatin-alginate mixture) was injected, using a 1 ml syringe without needle, into 6 mm×6 mm×3 mm rectangular silicone molds. Immediately thereafter, 0.04 ml of sub-formulation B (EDC aqueous solution) was mixed with sub-formulation A to form a pre-curing bioadhesive formulation (140 μl) in the mold. The wet bioadhesive matrix samples were pressed out of their silicone molds a few minutes later, after the bioadhesive formulation was fully cured, and air-dried in a chemical hood.

The air-dried bioadhesive matrix's cuboids were put in plastic test tubes, and 1 ml of sterile PBS buffer at pH 7 was add to each test tube and used as a release medium. Sodium azide (0.02% w/v) was added to the medium in order to prevent microbial contamination. After adding the medium, the test tubes (with the bioadhesive samples inside) were seals with plastic caps and were placed in a static incubator (Heraeus, B12) at 37° C. for 14 days.

At specific time points during the experiment, namely 6 hours, 1, 2, 3, 7 and 14 days, the entire medium was removed from the test tubes and replaced with an equal volume of fresh PBS buffer solution and 0.02% w/v sodium azide. The removed medium was transferred into glass HPLC vials and kept at −20° C. until analyzed. For the determination of the drug release kinetics, the concentrations of the drugs in the removed medium at each time point were evaluated using an HPLC system.

The HPLC analyses of the samples containing bupivacaine were performed using a Jasco HPLC system equipped with a UV 2075 plus detector that was set on 210 nm, and a reverse phase column (ACE 5 C18, inner diameter d=4.6 mm, length=250 mm), kept at 40° C. The mobile phase consisted of a mixture of PBS (pH 3.3) and acetonitrile mixture (72:28%, v/v) at a flow rate of 1.5 ml/min with a quaternary gradient pump (PU 2089 plus) without gradient. 1-100 μl samples were injected with an auto sampler (AS 2057 Plus). The area of each eluted peak was integrated using EZstart software version 3.1.7, using a calibration curve.

The HPLC analyses of the samples containing ibuprofen were performed using a Jasco HPLC system equipped with a UV 2075 plus detector that was set on 220 nm, and a reverse phase column (ACE 5 C18, inner diameter d=4.6 mm, length=250 mm), kept at 40° C. The mobile phase consisted of a mixture of PBS (pH 3.3) and acetonitrile mixture (40:60%, v/v) at a flow rate of 2 ml/min with a quaternary gradient pump (PU 2089 plus) without gradient. 1-100 µl samples were injected with an auto sampler (AS 2057 Plus). The area of each eluted peak was integrated using EZstart software version 3.1.7, using a calibration curve.

14 days after the in vitro drug elution process has started, the bioadhesive samples were immersed in "trypsin A" solution at 37° C. for 4 hours, in order to dissolve the samples and to extract the drug that was not released during the first 14 days. The dissolved solutions were filtered using a disposable filer unit (Whatman, 0.2 µm), injected into the HPLC system and analyzed according to the protocols mentioned hereinabove in order to determine the amount of the drug remainders.

Water Uptake:

Two hours after mixing the pre-curing bioadhesive formulation containing primarily gelatin and alginate with EDC, the cured bioadhesive matrix was weighed and a dry weight $W_{dry}$ was recorded. Thereafter five milliliters of PBS buffer solution (pH 7) was added thereto. The plate with the bioadhesive matrix sample was inserted to an incubator (Heraeus, B12) at 37° C. and 100% humidity for 0.5, 1, 2, 5, 24 and 48 hours.

When the allotted time expired the PBS solution was removed from the plate and the swollen bioadhesive matrix sample was weighed and the wet weight $W_{wet}$ was recorded. The water uptake (swelling) ratio was calculated according to the formula $(W_{wet}-W_{dry}) \times 100/W_{dry}$.

The drug release rate can be affected by the swelling of a drug-loaded hydrogels. Air-dried drug free bioadhesive cuboids were placed in plastic test tubes and were soaked in 1 ml drug release medium (PBS pH 7 and 0.02% sodium azide) and placed in a static incubator (Heraeus, B12) at 37° C. for 6 hours. Weight values of the samples the soaked samples ($W_{dry2}$). The water uptake was calculated as $(W_{wet}-W_{dry2}) \times 100/W_{dry1}$.

Cytotoxicity Test:

Fibroblast cells (14$^{th}$ passage) were thawed and cultured in 75 mm$^2$ flasks with culture medium at 37° C., humidified atmosphere and 5% $CO_2$. The cells were cultured with modified Eagle's medium supplemented with 10% fetal bovine serum, 1% L-glutamine and 0.1% penicillin-streptomycin-nystatin. At confluence of 70% (at passages 16-19) the cells were separated using incubation for 3 minutes with 1 ml trypsin A, the free cells were added to the culture medium and seeded in a 6 well plate.

When confluence of 70% was reached the medium was replaced by 2 ml of medium containing 10% v/v Alamar blue for 4 hours of incubation. Thereafter, two 100 µL samples were taken from each well and inserted to a 96 well plate. The plate was inserted for analysis at a spectrophotometer (Spectra max 340 PC384, Molecular Devices) at 570 and 600 nm.

Two experiments were carried out, at first each component of the bioadhesive were inserted separately to a test tube containing 4 ml medium and incubated for 24 hours and then that medium was added to the cells instead of the medium containing Alamar Blue. In the second experiment, the medium with Alamar Blue was replaced with 4 ml of fresh medium and 0.1 ml of bioadhesive was added to the medium and incubated for 24 hours followed by another reading using Alamar Blue.

The reduction of Alamar Blue is an indication of changes in cell proliferation; hence the results were compared to the initial reading without the tissue adhesive. The reduction of Alamar Blue's absorption was calculated using the manufacturer's protocol, namely Alamar Blue reduction= $(\epsilon_{600}A^t_{570}-\epsilon_{570}A^t_{600})/(\epsilon_{570}A^c_{600}-\epsilon_{600}A^c_{570})$, wherein $\epsilon_{570}$ and $\epsilon_{600}$ are the molar extinction coefficients of oxidized Alamar Blue at 570 nm and 600 nm respectively, $A^t$ and $A^c$ are the absorbance of test and control respectively at 570 nm and 600 nm respectively, whereas the control is taken as the medium with Alamar blue but without any cells.

Microstructure Characterization:

The microstructure of drug-loaded bioadhesive matrices, according to some embodiments of the present invention, was investigated in order to characterize the dispersion of different drugs in the bioadhesive matrix, and to examine the effect of the microstructure on the drug release profiles and bonding strength. For this purpose, air-dried drug-loaded bioadhesive cuboids of about 24×24×3 mm, prepared from 420 µl of a bioadhesive formulation according to embodiments of the present invention, were freeze fractured and their cross section was observed using an environmental scanning electron microscope (Quanta 200 FEG ESEM) in a high vacuum mode, with an accelerating voltage of 10 kV. The mean diameter of the drug crystals and aggregates was analyzed using the Sigma Scan Pro software.

Hard Tissue Bonding Strength Measurements:

Cortical portions of bovine femurs (purchased at a local abattoir) were used as a hard tissue model in order to evaluate the effect of the addition of fillers to the bioadhesive formulation on the bonding strength of the resulting bioadhesive matrix.

Femur bone samples were sawed into 2×2×0.2 cm cuboid specimens using a "FMB-minor" portable band saw. The specimens were attached firmly to metal testing holders with a matching surface area.

The bonding strength measuring system was based on the system used for soft tissue adhesion as presented herein, and had similar dimensions.

140 µl of the bioadhesive formulation containing various concentrations of the tested fillers, were spread uniformly on the exposed side of two femur specimens. The specimens were then immediately attached to each other by applying a load of 7.5 N and placed in a 37° C. and 100% humidity environment. After 30 minutes, the bonding strength was measured in tension mode at room temperature using a 5500 Instron universal testing machine (Instron Engineering Corp.) and a 2 kN load cell.

The two parts of the femur joint were strained at a constant velocity of 2 mm per minute until separation was achieved.

The mechanical testing procedure was inspired by the standard test method ASTM F-2258-03. The bonding strength was defined as the maximum strength in the stress-strain curve, measured by the Instron Merlin software.

Example 2

Background Art

Formulations based on the teaching of Sung et al. [*J. Biomed. Materials Res.*, 46(4), p. 520-530, 1999], were prepared for comparison with the bioadhesive formulations and matrices according to some embodiments of the present invention.

Briefly, stock solution were prepared by pre-weighed amount of alginate was dissolved in distilled water at 50° C. and once the solution cleared pre-weighed amount of gelatin was added thereto and stirred until the solution became clear. The resulting mixture contained 600 mg/ml gelatin and 30 mg/ml alginate. The coupling agent EDC was dissolved in distilled water to afford a 10 mg/ml solution and a 20 mg/ml solution.

Testing of the resulting formulation was performed as follows. Shortly prior to use, 0.1 ml gelatin-alginate stock solution was mixed with 0.035 ml EDC stock solution to afford a final concentration of 445 mg/ml gelatin, 22 mg/ml alginate and 2.6 mg/ml EDC. This mixture was prepared on a piece of pig skin and thereafter a second piece of skin was laid over the formulation and the coupled skin pieces were put under pressure of 0.129 kg for 30 minutes in a moist incubator (100% humidity, 37° C.). The coupled skin pieces were subjected to mechanical testing protocol as presented hereinabove, and exhibited a result of 4436±1361 Pa. It is noted that the resulting formulation was difficult to apply on the skin piece due to too rapid gelation at room temperature.

In another attempt to reproduce the formulation reported by Sung et al. a formulation having a final concentration of 600 mg/ml gelatin, 30 mg/ml alginate and 20 mg/ml EDC, prepared from a stock solution of 840 ml/ml gelatin and 42 mg/ml alginate in water. This formulation was impossible to apply regardless of the coupling agent concentration.

Example 3

Bonding Strength

Several series of measurements were performed in order to elucidate the effect of each component of the bioadhesive formulation on the resulting bioadhesive matrix' bonding strength, expressed in kilo-pascal (KPa). The effects of the gelatin, alginate and coupling agent EDC concentrations are presented in Table 1, FIG. 1 and FIG. 2.

Table 1 presents the results of the bonding strength tests as conducted on four series of samples divided by varying parameter, wherein alginate varies in Series 1, 2 and 3 while gelatin varies across Series 1-3, and EDC varies in Series 4 while gelatin and alginate are constant.

TABLE 1

| Formulation | Gelatin concentration (mg/ml) | Alginate concentration (mg/ml) | EDC concentration (mg/ml) | Bonding strength (KPa) |
|---|---|---|---|---|
| Series 1 | 100 | 20 | 4 | 2.29 ± 0.29 |
|  | 100 | 40 | 4 | 2.22 ± 0.38 |
|  | 100 | 60 | 4 | 2.57 ± 0.34 |
| Series 2 | 150 | 20 | 4 | 3.17 ± 0.48 |
|  | 150 | 40 | 4 | 4.12 ± 0.55 |
|  | 150 | 60 | 4 | 2.58 ± 0.3 |
| Series 3 | 200 | 20 | 4 | 4.99 ± 0.43 |
|  | 200 | 40 | 4 | 5.5 ± 0.29 |
|  | 200 | 60 | 4 | 3.2 ± 0.36 |
| Series 4 | 200 | 40 | 0 | 2.79 ± 0.44 |
|  | 200 | 40 | 4 | 2.81 ± 0.45 |
|  | 200 | 40 | 10 | 5.02 ± 0.57 |
|  | 200 | 40 | 15 | 5.52 ± 0.91 |
|  | 200 | 40 | 20 | 9.84 ± 0.85 |

Figure 2:
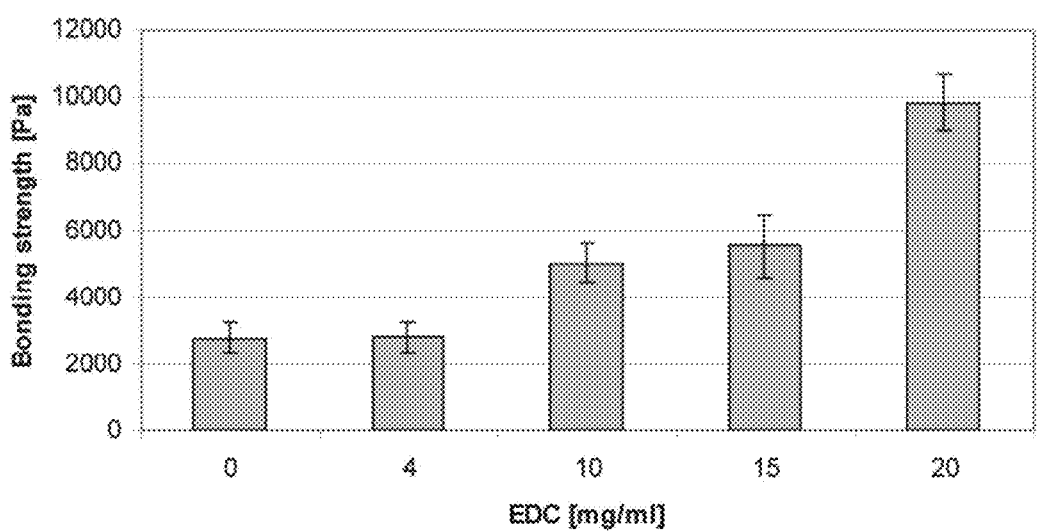
FIG. 2 presents a bar plot showing the effect of coupling agent (EDC) concentration in exemplary bioadhesive formulations, according to some embodiments of the present invention, on the bonding strength of the resulting bioadhesive matrix, varying 0, 4, 10, 15 and 20 mg/ml EDC in the formulation, wherein gelatin is at a concentration of 200 mg/ml and alginate is at a concentration of 40 mg/ml in the formulation.

As can be seen in Table 1, FIG. 1 and FIG. 2, the bonding strength is increased with the increase in gelatin concentration, and the highest bonding strength was observed for alginate concentration is about 40 mg/ml. An increase in the EDC concentration resulted in an increase in the bonding strength.

A bioadhesive formulation, comprising gelatin at a concentration of 200 mg/ml, alginate at a concentration of 40 mg/ml and EDC at a concentration of 20 mg/ml, was selected to represent an exemplary bioadhesive formulation for the studies presented hereinbelow. This bioadhesive formulation resulted in a bioadhesive matrix exhibiting bonding strength of approximately 10 KPa, which is four-times stronger than that of Evicel™ (a fibrin sealant produced by Johnson and Johnson with a bonding strength of approximately 2.5 KPa as measured using the system and protocol presented hereinabove).

Figure 3:
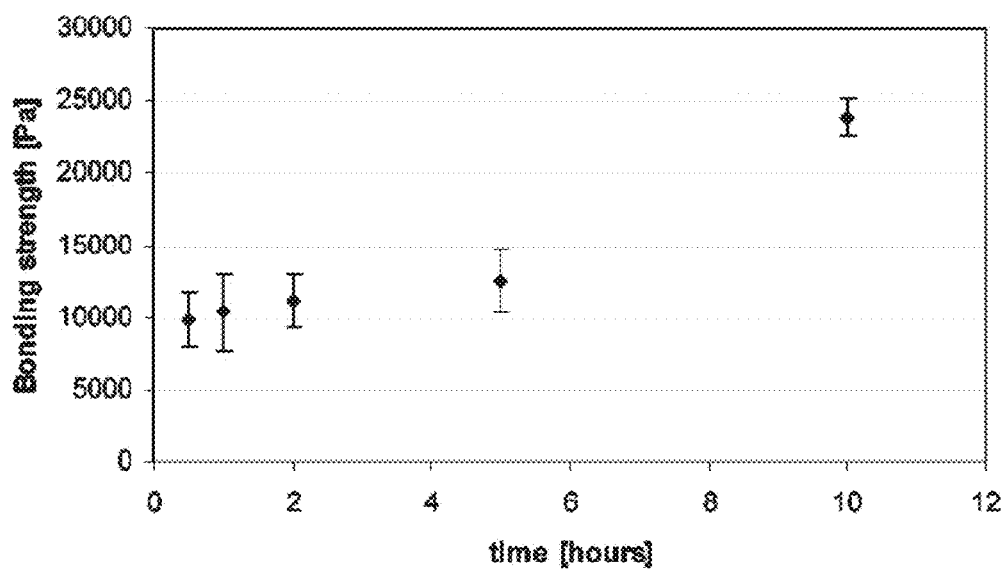
FIG. 3 presents a scatter plot showing the bonding strength of an exemplary bioadhesive matrix according to some embodiments of the present invention, which was afforded from an exemplary bioadhesive formulation comprising 200 mg/ml gelatin, 40 mg/ml alginate, and 20 mg/ml EDC, as a function of time after forming the pre-curing bioadhesive formulation by mixing the gelatin-alginate mixture with the coupling agent EDC.

The effect of time on the bonding strength of the selected bioadhesive formulation is presented in FIG. 3.

As can be seen in FIG. 3, the bonding strength only slightly changes during the first 5 hours, but after 10 hours there is a significant increase in the bonding strength and it reaches approximately 24 KPa. The later may explained by some dehydration of the skin. The results show that this exemplary bioadhesive matrix maintains sufficient strength for at least 10 hours.

Figure 4:
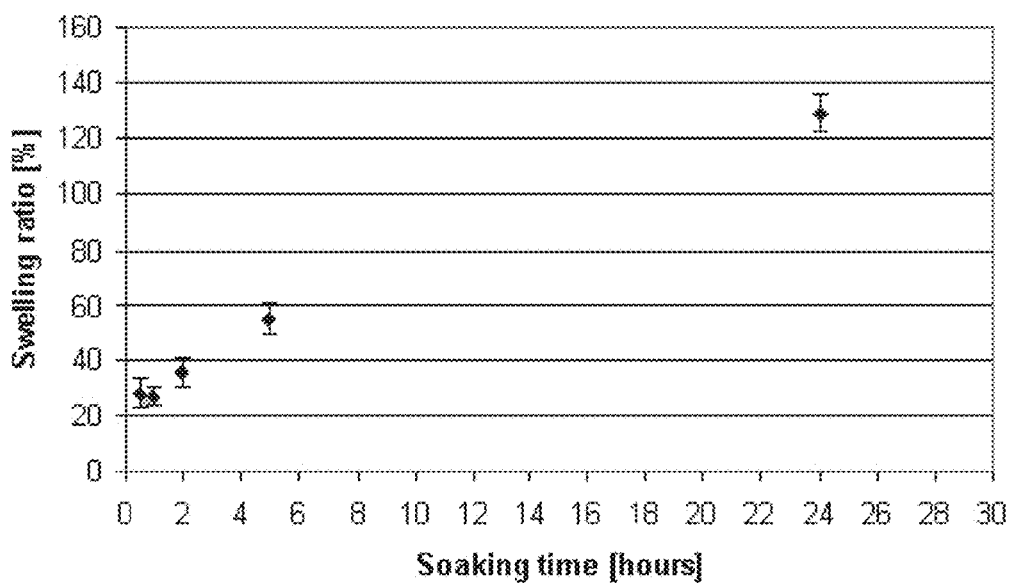
FIG. 4 presents a scatter plot showing the water uptake (swelling ratio) as a function of immersion time of exemplary bioadhesive matrices, as measured for an exemplary bioadhesive matrix according to some embodiments of the present invention, afforded from an exemplary bioadhesive formulation comprising 200 mg/ml gelatin, 40 mg/ml alginate, and 20 mg/ml EDC.

Two hours after mixing the components of the bioadhesive formulation, a sample of the resulting bioadhesive matrix was immersed in an aqueous medium for 24 hours so as to evaluate its water uptake kinetics to gives an indication for swelling and the results are presented in FIG. 4.

As can be seen in FIG. 4, the water uptake increases with immersion time linearly, while it is relatively low during the first 5 hours. This result is desirable for tissue bioadhesive applications.

Example 4

Elution of Bioactives

Analyzing the influence of the components of the bioadhesive formulations, according to some embodiments of the present invention, on various drug release profiles from the corresponding bioadhesive matrix, allows not only designing a controlled release product that fits the specific therapeutic demands of the bioadhesive, but also provides insights on the principles of drug release kinetics from a bioadhesive matrix.

Effect on Bonding Strength:

Two types of drug-eluting samples of bioadhesive matrices were examined: bupivacaine-loaded bioadhesive matrices and ibuprofen-loaded bioadhesive matrices.

A formulation containing gelatin (200 mg/ml), alginate (40 mg/ml) and EDC (20 mg/ml) was chosen an exemplary bioadhesive formulation. The bonding strength in tension was measured for matrices containing three different drug concentrations (loads), 1% w/v, 2% w/v and 3%, and the results are presented in FIG. 5 and FIG. 6, and in Table 2 hereinbelow.

TABLE 2

|  | Gelatin content [mg/ml] | Alginate content [mg/ml] | EDC content [mg/ml] | Drug content [% w/v] | Bonding strength [kPa] |
|---|---|---|---|---|---|
| Drug-free bioadhesive | 200 | 40 | 20 | 0 | 9.84 ± 1.91 |
| Bupivacaine loaded bioadhesives | 200 | 40 | 20 | 1 | 10.10 ± 1.73 |
|  |  |  |  | 2 | 13.71 ± 2.21 |
|  |  |  |  | 3 | 15.01 ± 1.92 |
| Ibuprofen loaded bioadhesives | 200 | 40 | 20 | 1 | 6.10 ± 1.12 |
|  |  |  |  | 2 | 4.37 ± 1.13 |
|  |  |  |  | 3 | 4.47 ± 0.78 |

Figure 5:
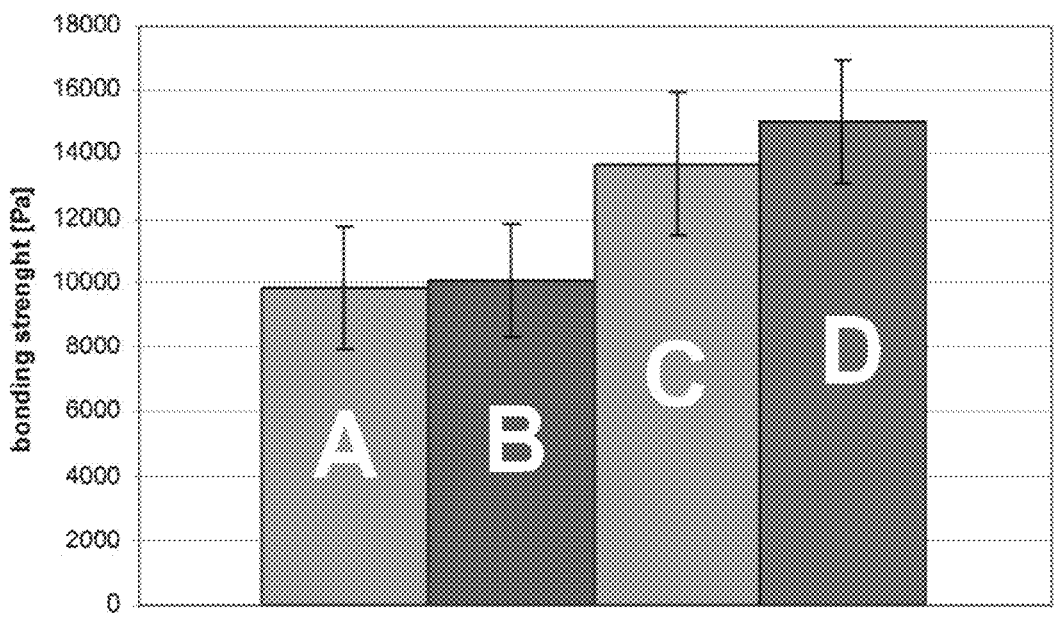
FIG. 5 presents a bar plot showing the effect of bupivacaine content on the bonding strength of exemplary bioadhesive matrices, according to some embodiments of the present invention, afforded from an exemplary bioadhesive formulation comprising 200 mg/ml gelatin, 40 mg/ml alginate, and 20 mg/ml EDC, wherein "A" represents drug-free samples, "B" represents samples loaded with 1% w/v bupivacaine, "C" represents 2% w/v bupivacaine and "D" represents samples loaded with 3% w/v bupivacaine.
Figure 6:
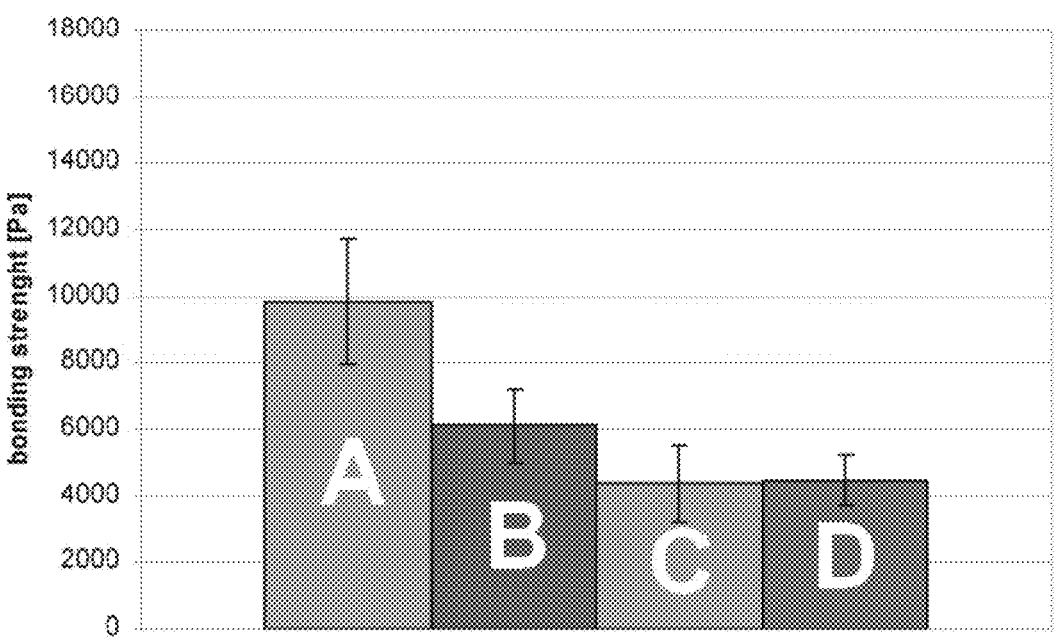
FIG. 6 presents a bar plot showing the effect of ibuprofen content on the bonding of exemplary bioadhesive matrices, according to some embodiments of the present invention, afforded from an exemplary bioadhesive formulation comprising 200 mg/ml gelatin, 40 mg/ml alginate, and 20 mg/ml EDC, wherein "A" represents drug-free samples, "B" represents samples loaded with 1% w/v ibuprofen, "C" represents 2% w/v ibuprofen and "D" represents samples loaded with 3% w/v ibuprofen.

As can be seen in Table 2, FIG. 5 and FIG. 6, bioadhesive matrices incorporating bupivacaine and ibuprofen showed an opposite effect on their bonding strengths. While bupivacaine has a positive effect of increasing the bonding strength of the bioadhesive, ibuprofen decreased the bonding strength.

Drug Release Profile:

The effects of the components of the bioadhesive formulations and drug content on the drug release profiles were examined in two types of drug-eluting bioadhesive matrices as presented hereinabove.

A reference bioadhesive formulation of 200 mg/ml gelatin, 40 mg/ml alginate and 20 mg/ml EDC containing 3% w/v bioactive agent, bupivacaine or ibuprofen, was chosen. The effect of each component of the bioadhesive formulation on the release profile from the corresponding bioadhesive matrix was examined through changing its concentration in the formulation while keeping the concentrations of the other components unchanged.

The concentration range for testing was determined according to the actual ability to apply the formulations, from both types of aspects, viscosity and toxicity (especially the toxic coupling agent).

(a) Bupivacaine Release:

In order to examine the gelatin effect on the release profile of bupivacaine, release profiles of bioadhesive matrices made from bioadhesive formulations with two gelatin concentrations, 100 mg/ml and 200 mg/ml, were measured. The obtained data is presented in FIG. 7.

Figure 7:
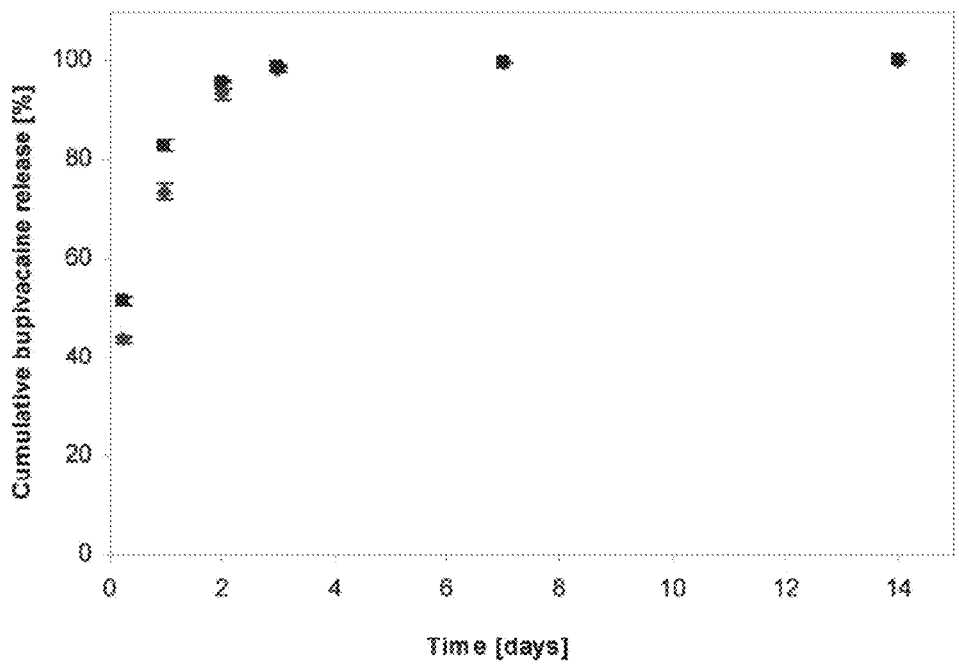
FIG. 7 presents a comparative scatter plot, showing the effect of gelatin concentration on the release profile of bupivacaine from exemplary bioadhesive drug-eluting matrices according to some embodiments of the present invention (afforded from exemplary bioadhesive formulations comprising 40 mg/ml alginate, 20 mg/ml EDC, 3% w/v bupivacaine and two gelatin concentrations), wherein the results obtained for the formulation having 100 mg/ml gelatin are marked by rhombs, and the results of the formulation having 200 mg/ml gelatin are marked by rectangles.

As can be seen in FIG. 7, the effect of gelatin concentration in the pre-curing bioadhesive formulation on the release rate of bupivacaine is subtle; a decrease in the gelatin concentration reduces the burst effect of the drug from the corresponding bioadhesive matrix.

In order to examine the alginate effect on the release profile of bupivacaine, release profiles from bioadhesive formulations of three different alginate concentrations, 20 mg/ml, 40 mg/ml and 60 mg/ml, were compared. The obtained data is presented in FIG. 8.

Figure 8:
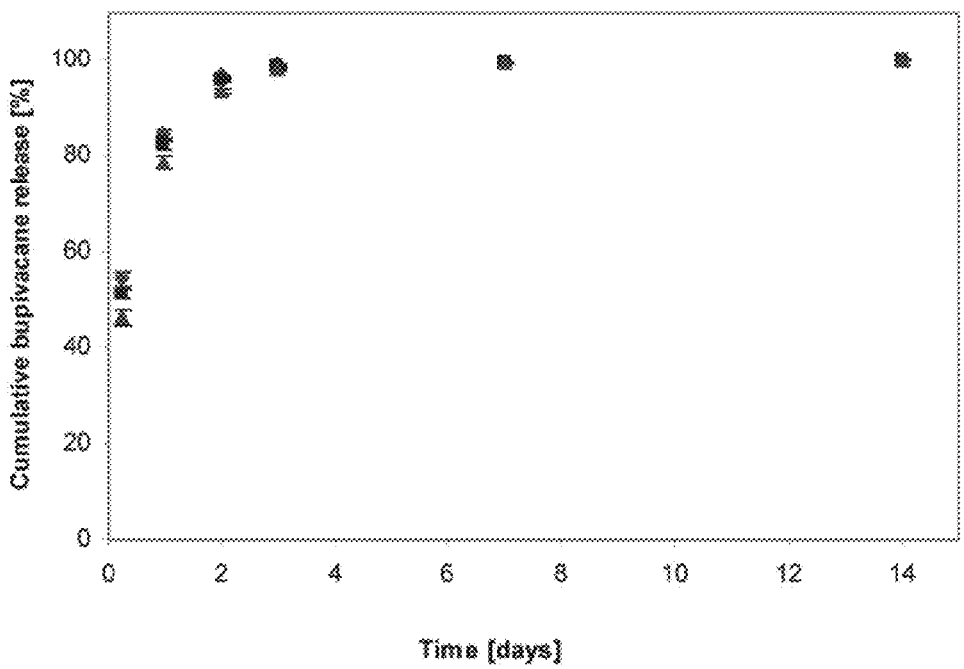
FIG. 8 presents a comparative scatter plot, showing the effect of alginate concentration on the release profile of bupivacaine from exemplary bioadhesive drug-eluting matrices according to some embodiments of the present invention (afforded from exemplary bioadhesive formulations comprising 200 mg/ml gelatin, 20 mg/ml EDC, 3% w/v bupivacaine and three alginate concentrations), wherein the results obtained for the formulation having 20 mg/ml alginate are marked by rhombs, the results of the formulation having 40 mg/ml alginate are marked by rectangles, and the results of the formulation having 60 mg/ml alginate are marked by triangles.

As can be seen in FIG. 8, a decrease in the alginate concentration in the pre-curing bioadhesive formulation increases the burst effect of the drug from the corresponding bioadhesive matrix.

In order to examine the EDC effect on the release profile of bupivacaine, release profiles from bioadhesive matrices prepared from pre-curing bioadhesive formulations containing five different EDC concentrations, 0 mg/ml, 4 mg/ml, 10 mg/ml, 15 mg/ml and 20 mg/ml, were compared. The obtained data is presented in FIG. 9.

Figure 9:
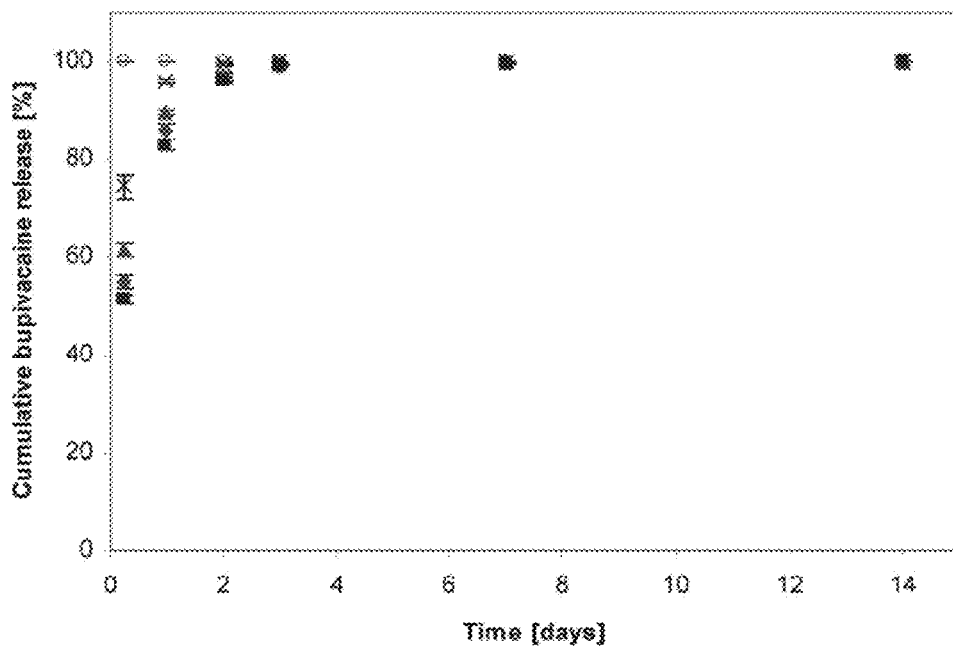
FIG. 9 presents a comparative scatter plot, showing the effect of EDC concentration on the release profile of bupivacaine from exemplary bioadhesive matrices according to some embodiments of the present invention (afforded from exemplary bioadhesive formulations comprising 200 mg/ml gelatin, 40 mg/ml alginate, 3% w/v bupivacaine and five EDC concentrations), wherein the results obtained for the formulation having no EDC are marked by circles, the results of the formulation having 4 mg/ml EDC are marked by X, the results of the formulation having 10 mg/ml EDC are marked by triangles, the results of the formulation having 15 mg/ml EDC are marked by rhombs, and the results obtained for the formulation having 20 mg/ml EDC are marked by rectangles.

As can be seen in FIG. 9, an increase in the EDC concentration decreases the burst effect of bupivacaine.

In order to examine the effect of drug content in a pre-curing bioadhesive formulation on its release profile from the corresponding bioadhesive matrix, release profiles of bupivacaine from matrices afforded from bioadhesive formulations containing three bupivacaine concentrations, 1% w/v, 2% w/v and 3% w/v, were compared. The obtained data is presented in FIG. 10.

Figure 10:
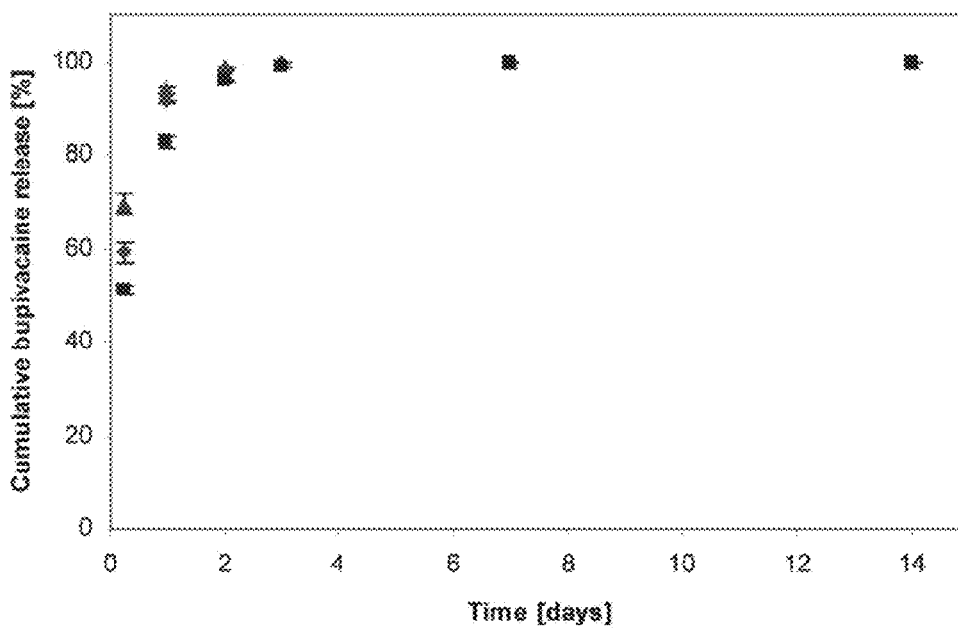
FIG. 10 presents a comparative scatter plot, showing the effect of bupivacaine concentration on the release profile of bupivacaine from exemplary bioadhesive drug-eluting matrices according to some embodiments of the present invention (afforded from exemplary bioadhesive formulations comprising 200 mg/ml gelatin, 40 mg/ml alginate, 20 mg/m EDC and three bupivacaine concentrations), wherein the results obtained for the formulation having 1% w/v bupivacaine are marked by triangles, the results of the formulation having 2% w/v bupivacaine are marked by rhombs, and the results of the formulation having 3% w/v bupivacaine are marked by rectangles.

As can be seen in FIG. 10, increasing the bupivacaine concentration decreases the burst effect of the drug.

It should be noted that in all matrices prepared from the exemplary tested bioadhesive formulations, approximately 99% of the encapsulated bupivacaine was released during the first 3 days of the experiment. Also, 100% of the drug was considered the total amount of bioactive agent that was released until the end of the experiment after 2 weeks, since the drug amount that remained in the matrix after the 2 weeks release was found to be negligible, which is reasonable considering the fact that bupivacaine is a hydrophilic drug which is released from the hydrophilic coupled gelatin-alginate matrix. The burst release values from all studied samples are presented in Table 3.

TABLE 3

| Gelatin content [mg/ml] | Alginate content [mg/ml] | EDC content [mg/ml] | Bupivacaine content [% w/v] | Burst effect (six hours) [%] |
|---|---|---|---|---|
| 100 | 40 | 20 | 3 | 43.68 ± 0.72 |
| 200 | | | | 51.28 ± 0.90 |
| 200 | 20 | 20 | 3 | 54.33 ± 1.74 |
| | 40 | | | 51.28 ± 0.90 |
| | 60 | | | 46.53 ± 1.60 |
| 200 | 40 | 0 | 3 | 100.00 ± 0.00 |
| | | 4 | | 74.36 ± 2.60 |
| | | 10 | | 61.24 ± 1.36 |
| | | 15 | | 55.09 ± 1.37 |
| | | 20 | | 51.28 ± 0.90 |
| 200 | 40 | 20 | 1 | 69.67 ± 2.35 |
| | | | 2 | 59.17 ± 2.21 |
| | | | 3 | 51.28 ± 0.90 |

The examination of the influence of EDC on bupivacaine release demonstrates the role of swelling and water penetration in the drug release mechanism. It was noticed that increasing the EDC concentration decreases the burst effect of bupivacaine.

In general, in a glassy state of the hydrogel, the diffusion ability of the drug is negligible, and when the hydrogel is hydrated sufficiently, it becomes rubbery and the drug can diffuse out.

Support for this result can be found in the water uptake tests which showed that the EDC concentration has a significant influence on the water uptake of the resulting bioadhesive matrix in the first hours of the release (see, FIG. 15 and Table 5 hereinbelow). Increasing the EDC concentration decreases the water uptake of the resulting bioadhesive matrix from the aforementioned reasons.

It can be seen from the release curves that bioadhesive matrices with no EDC had a 100% burst effect release because gelatin and alginate were not chemically cross-linked to any significant extent and therefore the formulation dissolved completely.

The drug concentration influence on its release rate experiment, demonstrates the diffusion-controlled character of the release. As can be seen from the release curves, although bioadhesive matrices made from formulations having a higher concentration of drug actually release a greater mass of drug in the burst release time-range, the burst effect is still smaller relative to the total amount of loaded drug.

The water uptake results (see, Example 5 below) showed that both gelatin and alginate have a similar effect on the swelling of the bioadhesive matrices in the first hours. Decreasing the concentration of both gelatin and alginate decrease also the water uptake of the corresponding bioadhesive matrix for two possible reasons.

It is noted that the isoelectric points (pKa) of bupivacaine and alginate are 8.1-8.4 and 3.4-4.4, respectively. This means that in the release conditions of pH 7, the bupivacaine molecules are positively charged and the alginate molecules are negatively charged. Thus, an electrostatic attraction occurs between bupivacaine and alginate. Therefore it is reasonable to assume that the delay in bupivacaine release when increasing the alginate concentration is as a result of electrostatic attraction.

The isoelectric point of gelatin type A, which has both amine and carboxylic groups in its side chains, is 7.0-9.0, which means that if not neutral, gelatin is positively charged in pH 7. Therefore, an electrostatic repulsion between the gelatin chains and the also positively charged bupivacaine molecules is expected, and it can be assumed that this repulsion is increased when the gelatin concentration in increased. This contributes also to a greater burst effect of bupivacaine besides water swelling.

The overall examination of the effects of all three components of the bioadhesive formulation (gelatin, alginate and EDC) on the release profile of a given concentration of bupivacaine in the bioadhesive matrix shows that the EDC has a more noticeable effect on the drug-release profile compared to that of gelatin and alginate.

(b) Ibuprofen Release:

The effect of EDC and drug content in the bioadhesive formulation on the release kinetics of ibuprofen was tested for bioadhesive matrices, according to some embodiments of the present invention.

Only a fraction of the encapsulated ibuprofen was released in the time period of the experiment. The appearance of two unidentified peaks (one singlet peak and one doublet peak) in the HPLC chromatogram, indicated that a portion of the ibuprofen molecules react with certain components in the pre-curing bioadhesive formulation to afford ibuprofen derivatives. As a result, creating ibuprofen release curves required defining a calculated theoretical amount of the loaded drug, based on the weight of the air-dried bioadhesive matrix samples, as the 100% amount of drugs in the samples.

In order to examine the EDC effect on the release profile of ibuprofen, release profiles from three matrices made from bioadhesive formulations having three different EDC concentrations were compared, 10 mg/ml, 15 mg/ml and 20 mg/ml EDC. The obtained data is presented in FIG. 11.

Figure 11:
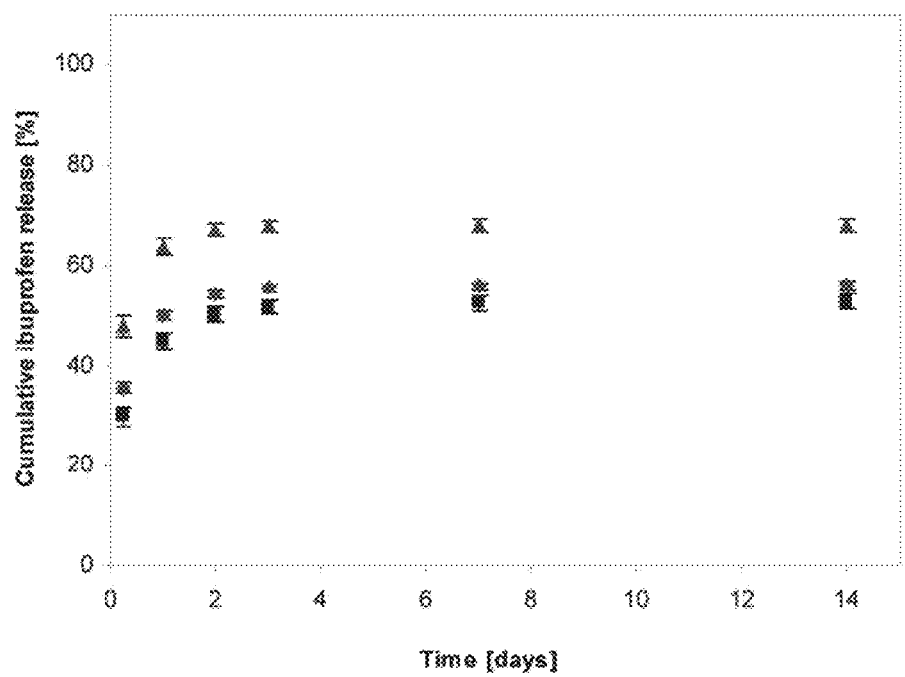
FIG. 11 presents a comparative scatter plot, showing the effect of EDC concentration on the release profile of ibuprofen from exemplary bioadhesive drug-eluting matrices according to some embodiments of the present invention (afforded from exemplary bioadhesive formulations comprising 200 mg/ml gelatin, 40 mg/ml alginate, 3% w/v ibuprofen and three EDC concentrations), wherein the results obtained for the formulation having 10 mg/ml EDC are marked by triangles, the results of the formulation having 15 mg/ml EDC are marked by rhombs, and the results of the formulation having 20 mg/ml EDC are marked by rectangles.

As can be seen in FIG. 11, increasing the EDC concentration in the bioadhesive formulation decreases the burst effect of ibuprofen from the corresponding matrix and the total efficiency of released ibuprofen.

In order to examine the ibuprofen effect on its release profile, three different ibuprofen concentrations were used in preparing bioadhesive formulations, 1% w/v, 2% w/v and 3% w/v ibuprofen. The obtained data is presented in FIG. 12.

Figure 12:
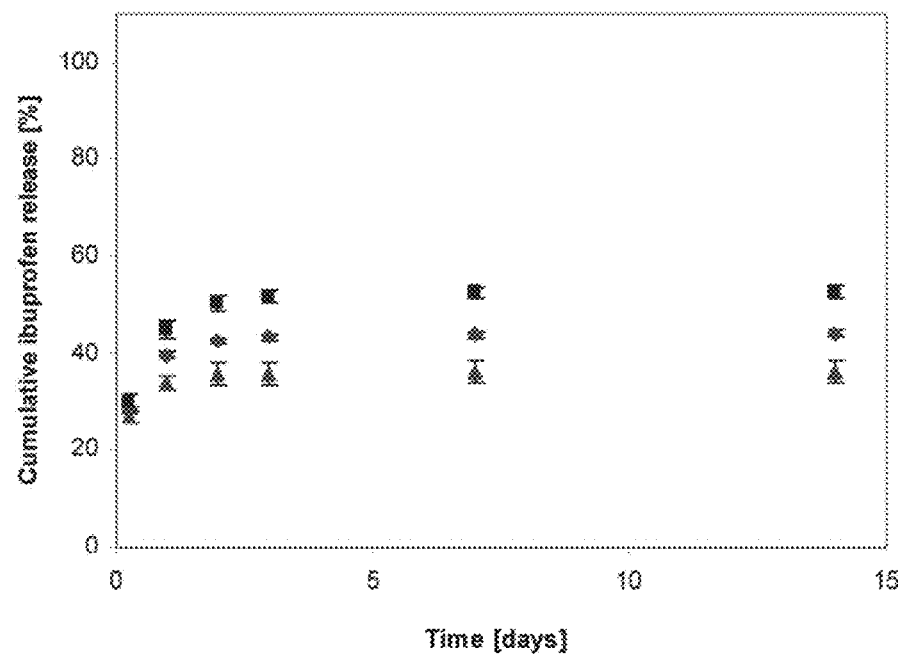
FIG. 12 presents a comparative scatter plot, showing the effect of ibuprofen concentration on the release profile of ibuprofen from exemplary bioadhesive drug-eluting matrices according to some embodiments of the present invention (afforded from exemplary bioadhesive formulations comprising 200 mg/ml gelatin, 40 mg/ml alginate, 20 mg/m EDC and three ibuprofen concentrations), wherein the results obtained for the formulation having 1% w/v ibuprofen are marked by triangles, the results of the formulation having 2% w/v ibuprofen are marked by rhombs, and the results of the formulation having 3% w/v ibuprofen are marked by rectangles.

As can be seen in FIG. 12, increasing the ibuprofen content in the bioadhesive formulation increases the efficiency of the total pristine ibuprofen that is released from the corresponding matrix, while the burst effect is affected marginally by the ibuprofen concentration.

The burst effect (first six hours) and total pure ibuprofen released from all studied samples are presented in Table 4.

As mentioned above, in view of the results it has been assumed that the ibuprofen molecule reacts with certain components in the bioadhesive formulation to afford ibuprofen derivatives. The reason for the ibuprofen's reactivity in the bioadhesive formulation is attributed to its carboxylic group.

The observed results of the release curves of ibuprofen support the assumed reaction between ibuprofen and EDC. Increasing the EDC concentration in the bioadhesive formulation decreased the burst effect of ibuprofen from the corresponding matrix, as expected, but also the efficiency of pristine ibuprofen release. As the EDC concentration in the formulation is increased under a constant concentration of the drug, the relative fraction of ibuprofen that reacts with the EDC grows as well. Similarly, increasing the ibuprofen concentration in the bioadhesive formulation increases its release efficiency, since at a constant concentration of EDC the relative fraction of ibuprofen that reacts with the EDC decreases.

Example 5

Initial Water Uptake

The effects of the concentration of various components in the bioadhesive formulations, according to some embodiments of the present invention, on the initial water uptake of the resulting matrices during the first six hours from preparation were examined. As a reference formulation a bioadhesive formulation containing 200 mg/ml gelatin, 40 mg/ml alginate and 20 mg/ml EDC was chosen.

Similarly to the drug release tests, the concentration range for the initial water uptake testing was determined according to the actual ability to apply the formulations in terms of viscosity in the case of gelatin and alginate, or toxicity in the case of EDC.

Figure 13:
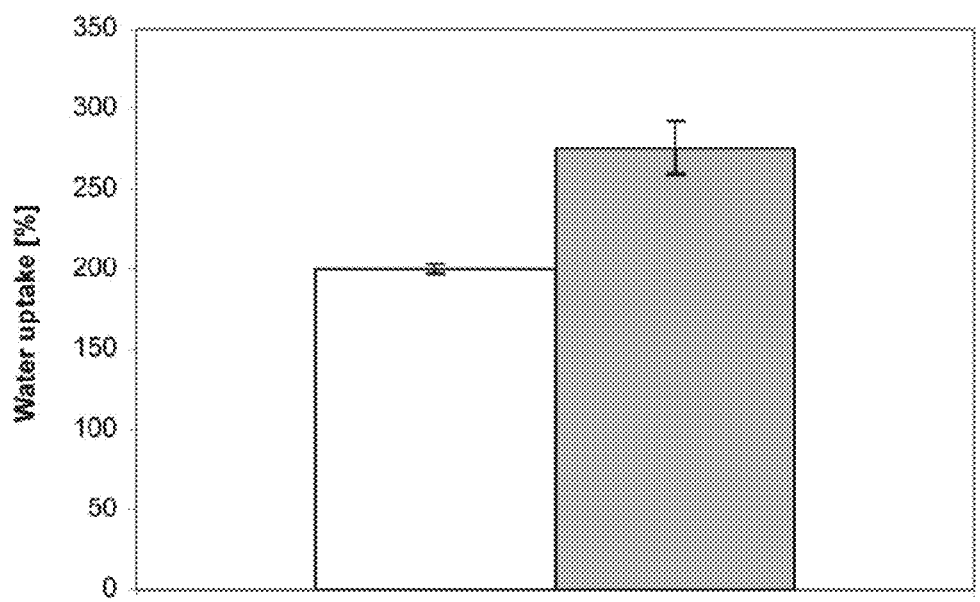
FIG. 13 presents a comparative bar plot, showing the effect of gelatin concentration on the water uptake of exemplary bioadhesive matrices afforded from exemplary bioadhesive formulations comprising 40 mg/ml alginate and 20 mg/ml EDC, wherein the white bar represents the result obtained for the bioadhesive formulation containing 100 mg/ml gelatin and the grey bar represents the result obtained for the bioadhesive formulation containing 200 mg/ml gelatin.
Figure 14:
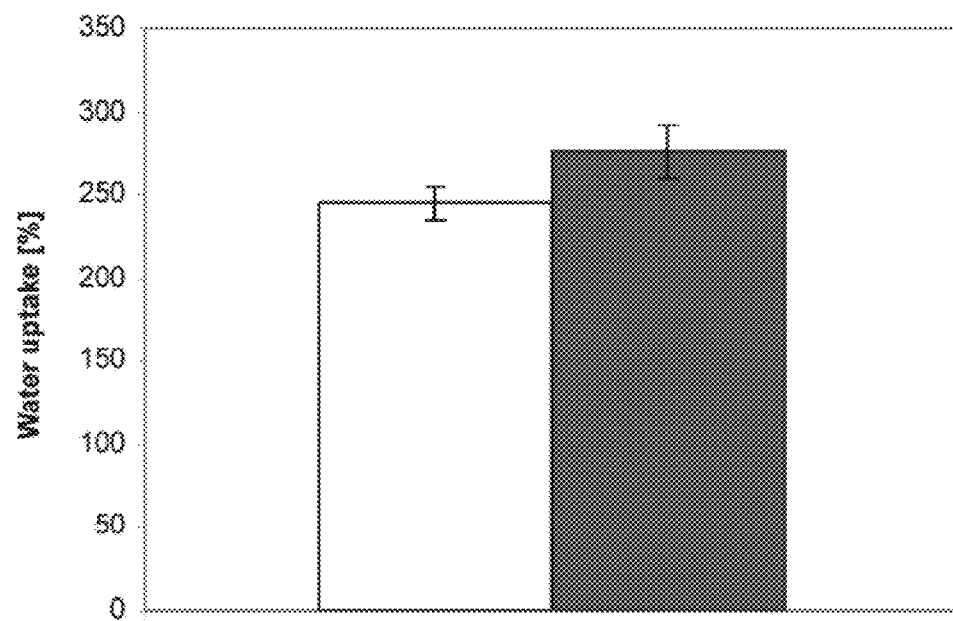
FIG. 14 presents a comparative bar plot, showing the effect of alginate concentration on the water uptake of exemplary bioadhesive matrices afforded from exemplary bioadhesive formulations comprising 200 mg/ml gelatin and 20 mg/ml EDC, wherein the white bar represents the result obtained for the bioadhesive formulation containing 20 mg/ml alginate and the grey bar represents the result obtained for the bioadhesive formulation containing 40 mg/ml alginate.
Figure 15:
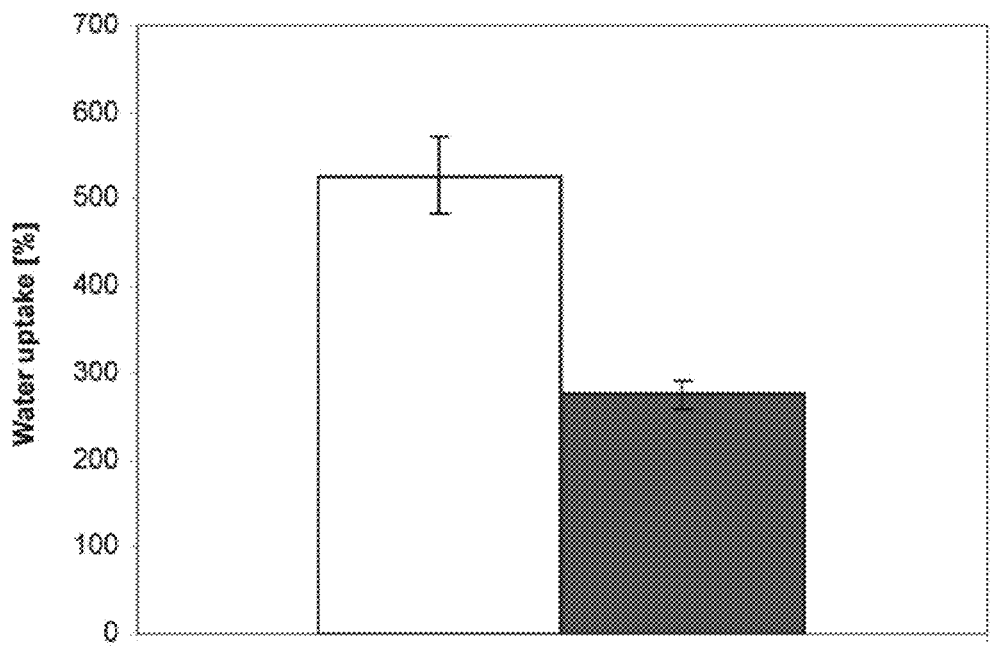
FIG. 15 presents a comparative bar plot, showing the effect of EDC concentration on the water uptake of exemplary bioadhesive matrices afforded from exemplary bioadhesive formulations comprising 200 mg/ml gelatin and 40 mg/ml alginate, wherein the white bar represents the result obtained for the bioadhesive formulation containing 10 mg/ml EDC and the grey bar represents the result obtained for the bioadhesive formulation containing 20 mg/ml EDC.

According to these criteria, the effect of gelatin concentration was examined on formulations containing 100 mg/ml and 200 mg/ml gelatin, the effect of alginate concentration was examined on formulations containing 20 mg/ml and 40 mg/ml alginate and the effect of EDC concentrations was examined on formulations containing 10 mg/ml and 20 mg/ml EDC, and the results are presented in FIG. 13, FIG. 14 and FIG. 15, respectively.

As can be seen in FIG. 13, FIG. 14 and FIG. 15, decrease in the EDC concentration increased the water uptake by the bioadhesive matrices, while decrease in the gelatin or alginate concentrations in the formulations decreased the water uptake by the corresponding bioadhesive matrix.

Table 5 summarizes the initial water uptake measured for exemplary bioadhesive matrices during the first six hours.

TABLE 4

| Gelatin content [mg/ml] | Alginate content [mg/ml] | EDC content [mg/ml] | Ibuprofen content [% w/v] | Burst effect (six hours) [%] | Cumulative ibuprofen released [%] |
|---|---|---|---|---|---|
| 200 | 40 | 10 | 3 | 47.85 ± 2.23 | 68.09 ± 1.19 |
|  |  | 15 |  | 35.59 ± 1.13 | 56.10 ± 0.75 |
|  |  | 20 |  | 29.85 ± 1.95 | 52.84 ± 1.33 |
| 200 | 40 | 20 | 1 | 26.93 ± 1.12 | 36.30 ± 2.23 |
|  |  |  | 2 | 28.26 ± 0.77 | 44.18 ± 0.67 |
|  |  |  | 3 | 29.89 ± 2.73 | 52.04 ± 2.13 |

TABLE 5

| Gelatin content [mg/ml] | Alginate content [mg/ml] | EDC content [mg/ml] | Initial water uptake (six hours) [%] |
|---|---|---|---|
| 100 | 40 | 20 | 200.14 ± 2.72 |
| 200 |  |  | 275.58 ± 16.69 |
| 200 | 20 | 20 | 244.94 ± 10.44 |
|  | 40 |  | 275.58 ± 16.69 |
| 200 | 40 | 10 | 528.10 ± 44.60 |
|  |  | 20 | 275.58 ± 16.69 |

Example 6

Cytotoxicity

In one experiment the effect of each component of the bioadhesive formulation, according to some embodiments of the present invention, on cytotoxicity was tested.

Figure 16:
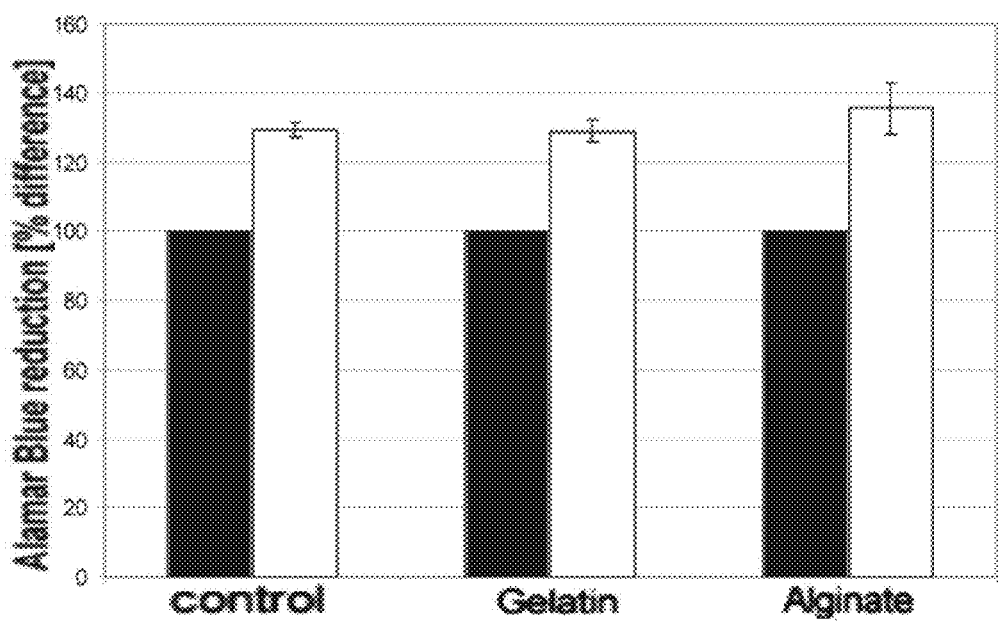
FIG. 16 presents a comparative bar plot showing the changes in cell viability of fibroblasts in the presence of medium that was previously incubated for 24 hours with the components of exemplary bioadhesive formulations, according to some embodiments of the present invention, namely gelatin or alginate, while cells kept in the presence of regular medium served as control, wherein white bars represent results obtained at time point 0 and the black bars represent the results obtained after 24 hours.

The obtained data is presented in FIG. 16.

As can be seen in FIG. 16, the results after 24 hours, compared to the control, show that the alginate or gelatin are biocompatible and do not induce any cytotoxic effects.

Figure 17A:
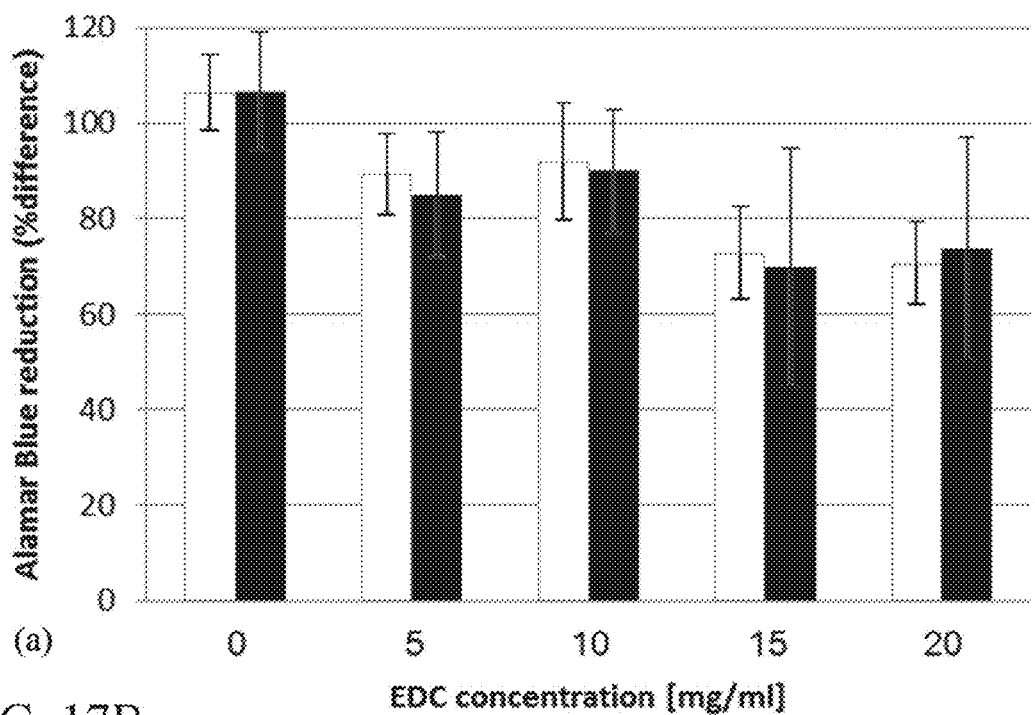
FIGS. 17A-B present comparative bar plots showing the changes in viability of fibroblasts in the presence of exemplary bioadhesive matrices, according to some embodiments of the present invention, afforded from exemplary bioadhesive formulations comprising 200 mg/ml gelatin and 40 mg/ml alginate (FIG. 17A), or 300 mg/ml gelatin and 30 mg/ml alginate (FIG. 17B) and different concentrations of EDC (0, 5, 10, 15 and 20 mg/ml), wherein white bars represent results obtained after 24 hours and the black bars represent the results obtained after 48 hours.
Figure 17B:
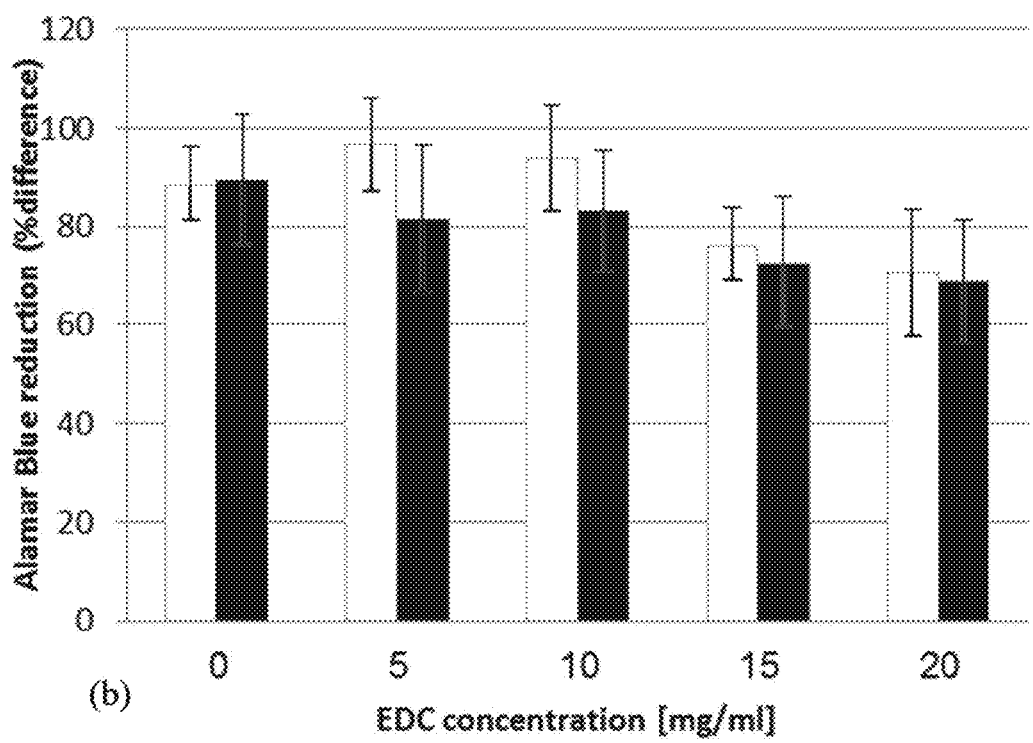

In another experiment, the effect of exemplary bioadhesive formulation/matrix on cells' viability was demonstrated by exposing cells to formulations based on 200 or 300 mg/ml gelatin and 40 or 30 mg/ml alginate and varying EDC concentrations (0, 5, 10, 15 and 20 mg/ml), and the results are presented in FIGS. 17A-B.

As can be seen in FIGS. 17A-B, as the concentration of EDC increases, the cell viability decreases. When cells were exposed to bioadhesive matrices based on 200 mg/ml gelatin and 40 mg/ml alginate and low concentrations of EDC (0, 5 and 10 mg/ml), the cells exhibit relatively high viability (89-100%), while at higher EDC concentrations (15 and 20 mg/ml), the cell viability decreases to 73% and 71%, respectively. This tendency was observed also after 48 hours of incubation with the medium that contains the bioadhesive matrices. When cells were exposed to bioadhesive formulations based on 300 mg/ml gelatin and 30 mg/ml alginate, low concentrations of the EDC (0, 5 and 10 mg/ml) results in relatively high cell viability (88-96%) while at higher EDC concentration (15 and 20 mg/ml) the cell viability decreases to 76% and 71%, respectively. In general, it can be concluded that relatively high viability is maintained even at relatively high EDC concentrations.

Therefore it can be concluded that the bioadhesive matrices afforded from bioadhesive formulations according to some embodiments of the present invention, are biocompatible and can safely be used.

Fibroblast viability was also examined after exposure to aqueous solutions of 1, 2 and 3% w/v bupivacaine and ibuprofen for 24 hours, by measuring their Alamar Blue reduction relative to the Alamar Blue reduction of control cells. The obtained data is presented in FIGS. 18A-B.

Figure 18A:
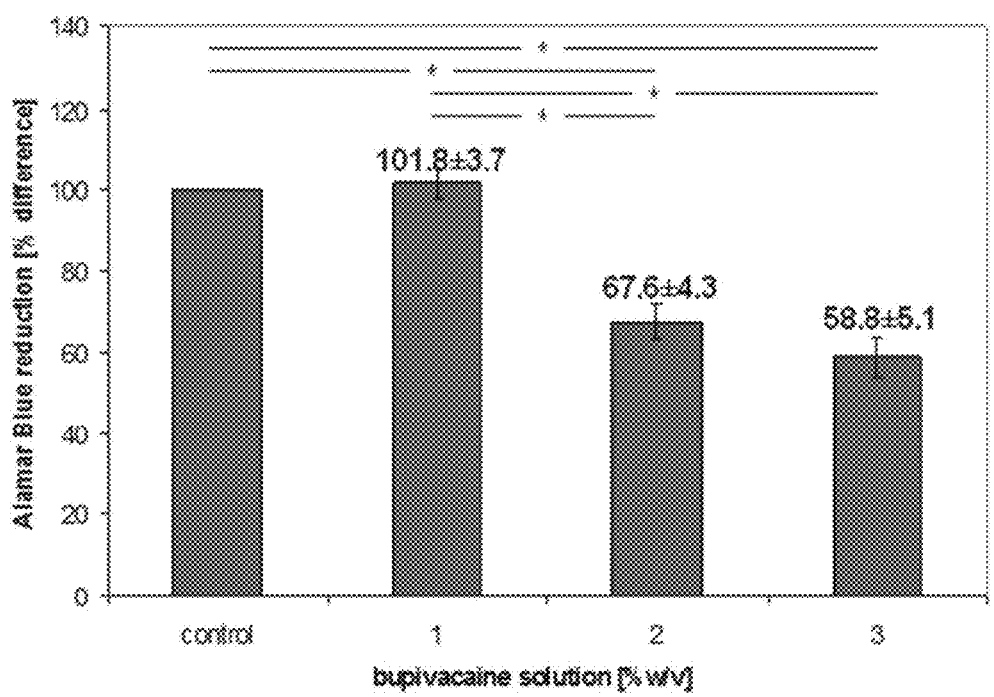
FIGS. 18A-B present comparative bar-plots, showing the cytotoxic effect of bupivacaine (FIG. 18A) and ibuprofen (FIG. 18B) concentrations in solutions on fibroblast cells based on Alamar-Blue reduction tests whereas significant differences are marked with "-*-"
Figure 18B:
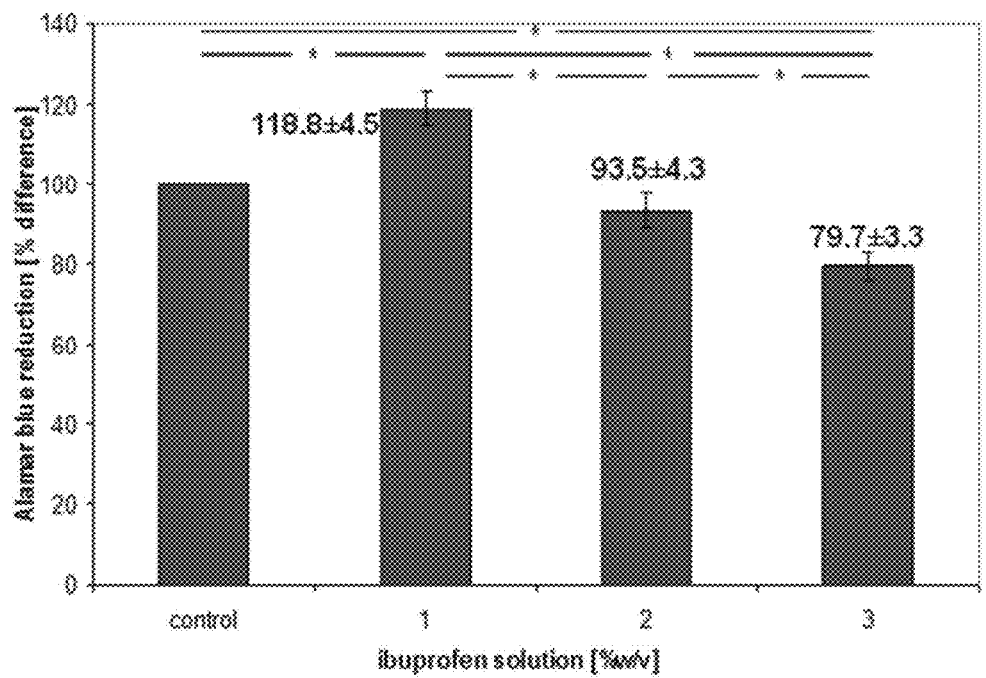

As can be seen in FIGS. 18A-B, some cytotoxic effects were obtained for both bupivacaine and ibuprofen when testing concentrations higher than 1% w/v. The cell viability values in the presence of bupivacaine (67.6% and 58.8% for 2% w/v and 3% w/v drug, respectively) were lower than those obtained in the presence of ibuprofen (93.5% and 79.7% for 2% w/v and 3% w/v drug, respectively). It is noted herein that at least 50% cell viability was achieved in all cases, compared to the control. It is also noted herein that this test is characterized by a tendency to afford low cell viability results compared to the experiments using drug-loaded bioadhesive matrices since the drugs are released gradually from bioadhesive matrix over 3 days, which is different from the conditions in this experiment.

Example 7

Microstructure Characterization

The bulk cross-sections of air-dried bioadhesive matrix specimens, according to some embodiments of the present invention, prepared with concentrations of gelatin (200 mg/ml), alginate (40 mg/ml) and EDC (20 mg/ml) and pre-loaded with 1% w/v bupivacaine or ibuprofen, were observed using environmental scanning electron microscope (ESEM). The obtained data is presented in FIG. 19.

As can be seen in FIGS. 19A-D, the drug-free reference sample did not demonstrate any phase separation, and exhibited some cracking which probably resulted from the fracturing process, while the fractographs of bupivacaine-loaded bioadhesive matrices provide a clear perspective of the dispersion and crystallization of the drug within the bioadhesive matrix. As can be seen in FIGS. 19B-D, bupivacaine is uniformly dispersed within the matrix and crystallizes into two levels of structure: a primary structure of needles that form fiber-shaped secondary structures. This type of crystallization apparently turns the bupivacaine-loaded bioadhesive matrix into a kind of fiber-reinforced composite material.

Evaluation of the fibers' diameter was performed by measuring the diameters of 50 fibers from the same area for 3 different specimens (total of 150 fibers). Evaluation of the needles' diameter was performed by measuring the diameters of 40 needles per fiber, for 3 different fibers (total of 120 needles). The bupivacaine-loaded bioadhesive matrix exhibited mean fiber and needle diameters of 11.69±2.49 and 0.49±0.09 µm, respectively. Regardless of the size of the bupivacaine crystals, their homogenous dispersion in the matrix indicates that the bupivacaine-loaded bioadhesive matrix is actually a type of monolithic system, exhibiting release profiles which are typical for monolithic devices.

The structure of the ibuprofen-loaded bioadhesive matrix samples has also been characterized. The presence of ibuprofen in the bioadhesive matrix samples could be detected in certain domains. An example for such a domain is shown in FIGS. 20A-B.

As can be seen in FIGS. 20A-B, the ibuprofen crystals were randomly distributed in the bioadhesive matrix in needle-shaped structures without any secondary structure.

Without being bound to any particular theory, it is assumed that ibuprofen, similarly to bupivacaine, is also uniformly dispersed in the matrix since it was mixed with the bioadhesive formulation components in the same way, and because its release profiles exhibited the same behavior of a decrease with time which is typical for monolithic systems.

Example 8

Bioadhesive Formulation Containing Fillers

The preparation of bioadhesive formulations containing the exemplary fillers, hydroxyapatite (HA) and beta-tricalcium phosphate (β-TCP), is based on the procedure for preparing bioadhesive formulation without a filler, and is carried out by dissolving various amounts of gelatin, alginate and filler powders in distilled water while heating to 60° C. Various amounts of a crosslinking agent (EDC) are added immediately prior to the bioadhesive's use. All studied formulations containing fillers are presented in Tables 6 and Table 7 below.

Table 6 presents the studied bioadhesive formulation containing HA and β-TCP for soft tissue adhesion.

TABLE 6

| Filler | Gelatin concentration (mg/ml) | Alginate concentration (mg/ml) | EDC concentration (mg/ml) | Filler concentration (% w/v) |
|---|---|---|---|---|
| Filler-free | 200 | 40 | 20 | 0 |
| HA | 200 | 40 | 20 | 0.125 |
|  |  |  |  | 0.25 |
|  |  |  |  | 0.5 |
|  |  |  | 10 | 0.125 |
|  |  |  |  | 0.25 |
|  |  |  |  | 0.5 |
| β-TCP | 200 | 40 | 20 | 0.125 |
|  |  |  |  | 0.25 |
|  |  |  |  | 0.5 |
|  |  |  | 10 | 0.125 |
|  |  |  |  | 0.25 |
|  |  |  |  | 0.5 |

Table 7 presents the studied bioadhesive formulation containing HA and β-TCP for hard tissue adhesion.

TABLE 7

| Filler | Gelatin concentration (mg/ml) | Alginate concentration (mg/ml) | EDC concentration (mg/ml) | Filler concentration (% w/v) | Filler content in dry samples (% w/w) |
|---|---|---|---|---|---|
| Filler-free | 200 | 40 | 20 | 0 | 0 |
| HA | 200 | 40 | 20 | 0.25 | 1 |
| β-TCP | 200 | 40 | 20 | 0.5 | 2 |

Example 9

Filler Effect on Soft Tissue Bonding Strength

The bonding strength of HA-loaded and β-TCP-loaded bioadhesive formulations to soft tissues, was measured at various filler concentrations: 0.125%, 0.25% and 0.5% w/v. These relatively low concentrations were chosen since while HA and β-TCP are essentially insoluble in aqueous solutions, these fillers could nonetheless be loaded inside the bioadhesive hydrogel with only minimal precipitation. The concentrations of gelatin (200 mg/ml), alginate (40 mg/ml) and EDC (20 mg/ml) were used in this study.

The bonding strength results were compared to the bonding strength of bioadhesive formulations prepared without fillers. Fifteen repetitions were carried out for each formulation, and the results are presented in FIG. 21.

Figure 21A:
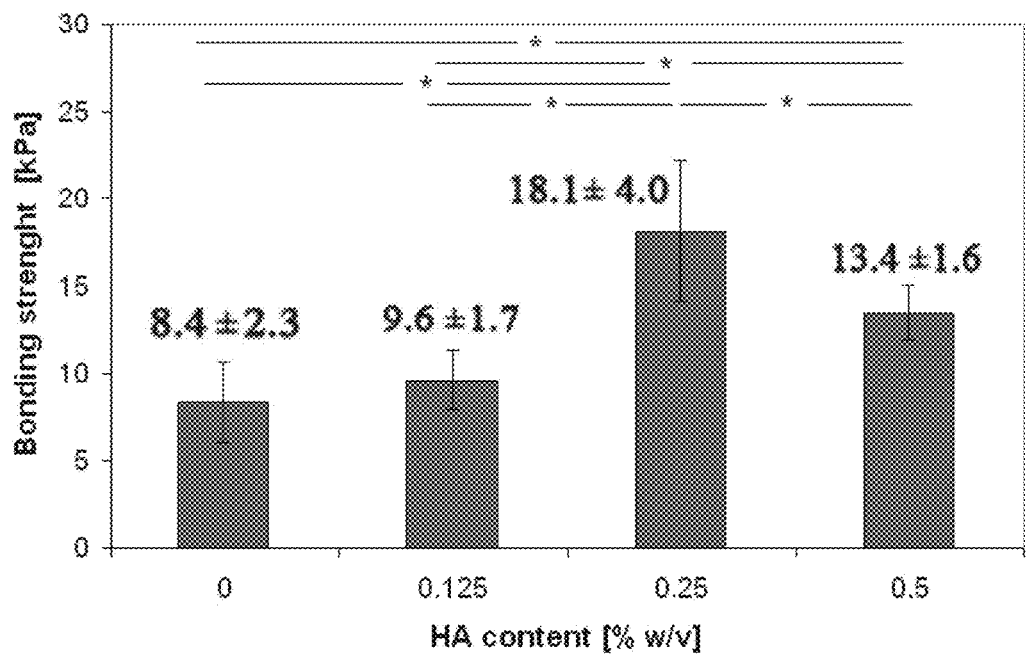
FIGS. 21A-B present comparative bar plots showing the effect of HA (FIG. 21A) and β-TCP (FIG. 21B) on the bonding strength of exemplary bioadhesive matrices according to some embodiments of the present invention, composed of gelatin (200 mg/ml), alginate (40 mg/ml) and EDC (20 mg/ml) to soft tissues, whereas significant differences are marked with "*"
Figure 21B:
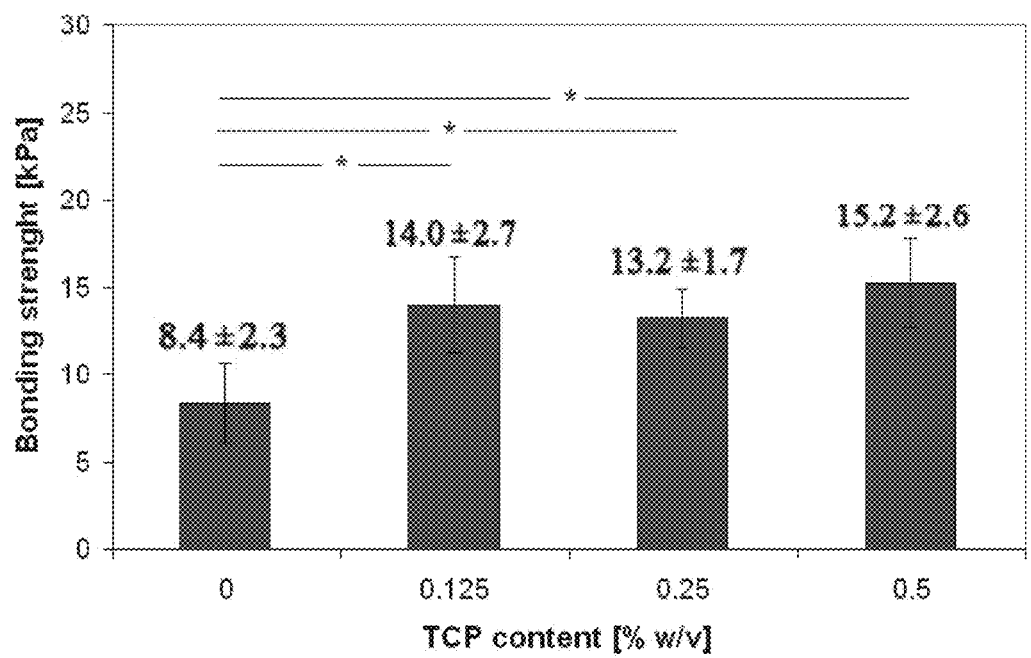

As can be seen in FIG. 21A, incorporation of both HA and β-TCP increased the bonding strength of the bioadhesive matrices. An increase of the bonding strength with HA was afforded at concentrations of 0.25% w/v and higher. The highest bonding strength was observed for a HA concentration of 0.25% w/v, 18.1±4.0 kPa compared to 8.4±2.3 kPa for the corresponding bioadhesive without a filler. Increasing the HA concentration to 0.5% w/v lowered the bonding strength (13.4±1.6 kPa), however, it was still higher than the bonding strength of the reference formulation. As can further be seen in FIG. 21B, all examined β-TCP concentrations were found to increase the bonding strength, with no significant difference observed between the samples prepared with different concentrations thereof. The highest average value was measured for a β-TCP concentration of 0.5% w/v (15.2±2.6 kPa).

A relatively low concentration of a crosslinking agent is beneficial in terms of biocompatibility and reduced cytotoxicity. Hence, the effect of fillers on the bonding strength of bioadhesive formulations with a reduced concentration of EDC (10 mg/ml) was studied as well using the same three concentrations of the fillers, namely 0.125%, 0.25% and 0.5% w/v) and the same for the polymeric components gelatin (200 mg/ml) and alginate (40 mg/ml) concentrations. Fifteen repetitions were carried out for each formulation, and the results are presented in FIGS. 22A-B.

Figure 22A:
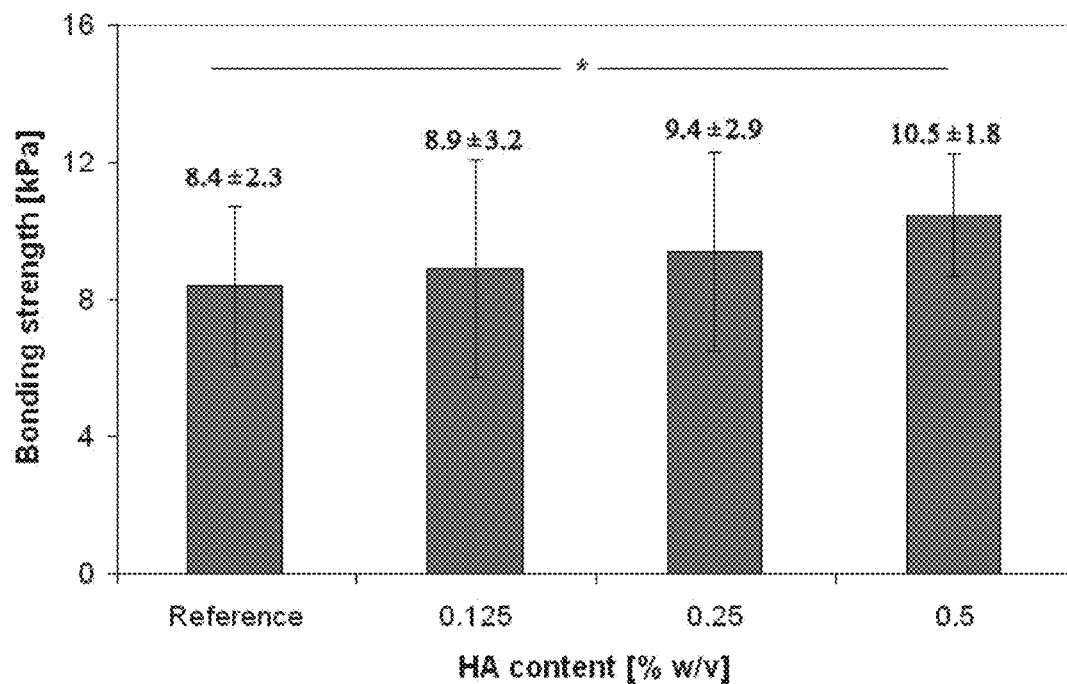
FIGS. 22A-B present comparative bar plots showing the effect of HA (FIG. 22A) and β-TCP (FIG. 22B) on the bonding strength of exemplary bioadhesive matrices according to some embodiments of the present invention, composed of gelatin (200 mg/ml), alginate (40 mg/ml) and reduced EDC (10 mg/ml) to soft tissues, whereas significant differences are marked with "*"
Figure 22B:
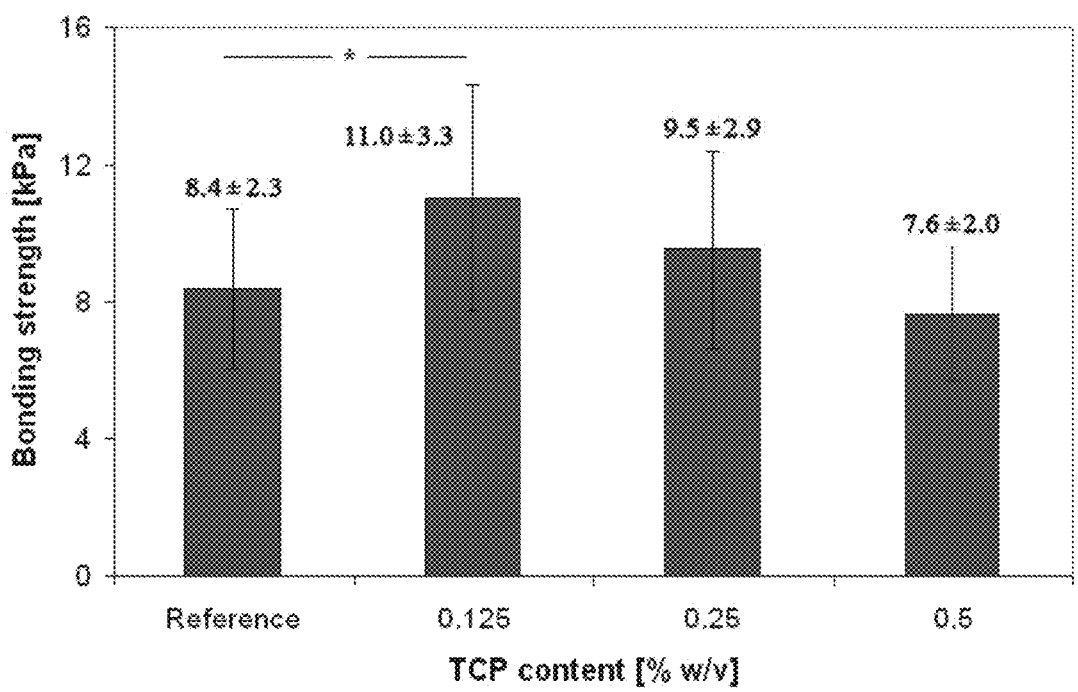

As can be seen in FIG. 22A, incorporation of HA-loaded and β-TCP-loaded bioadhesive formulations prepared with reduced amount of EDC (10 mg/ml) had bonding strengths similar to the bonding strength of the filler-free bioadhesive with EDC concentration of 20 mg/ml. Bioadhesive matrices containing reduced EDC (10 mg/ml) and concentrations of 0.5% and 0.125% w/v HA or β-TCP respectively, were found to have even higher bonding strength.

The bonding strength of Evicel™, a commercial fibrin glue, was also measured using the same bonding strength system, and a comparison between the bonding strength of Evicel™ (2.5±2.3 kPa) and a bioadhesive matrix containing HA and β-TCP, according to some embodiments of the present invention, showed that even when the EDC concentration was reduced by half, incorporation of the fillers enable the achievement of up to 7 times higher bonding strength to soft tissues compared with Evicel™.

Example 10

Filler Effect on Hard Tissue Bonding Strength

HA-loaded and β-TCP-loaded bioadhesive matrices, according to some embodiments of the present invention, were also examined for their potential use in hard tissue adhesion.

0.25% w/v HA and 0.5% w/v β-TCP were added to exemplary bioadhesive formulations, according to some embodiments of the present invention, and the bonding strength results were compared to a filler-free reference bioadhesive formulation, with the concentrations of the polymeric components maintained the same for all tests (EDC concentration set to 20 mg/ml). Three repetitions were carried out for each formulation, and the results are presented in FIG. 23.

Figure 23:
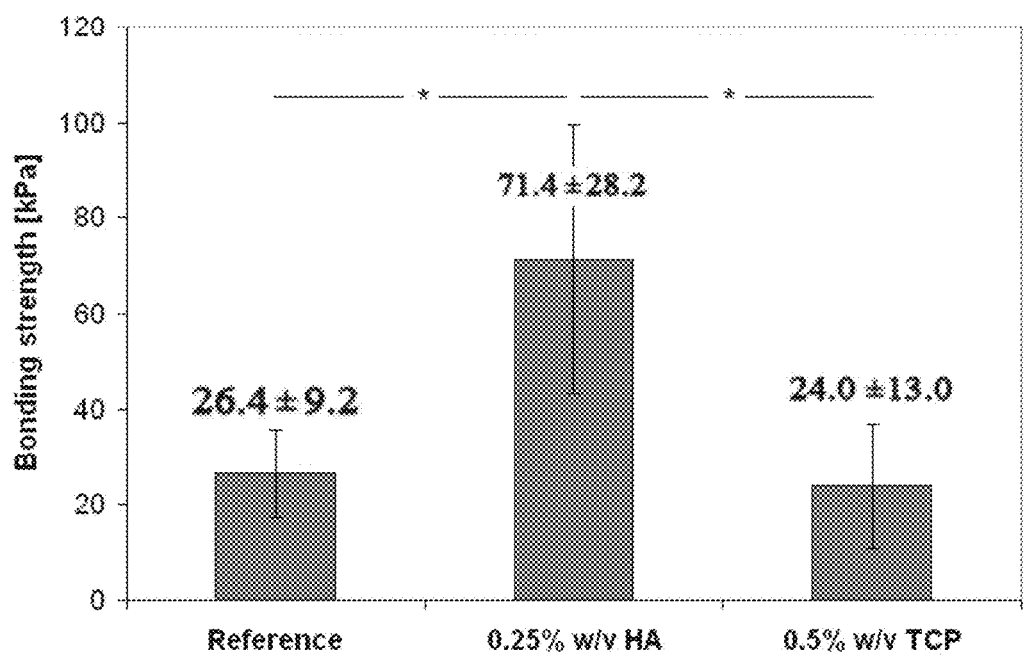
FIG. 23 presents a bar plot showing the effect of the addition of HA and β-TCP on the bonding strength of selected bioadhesive formulations composed of gelatin (200 mg/ml), alginate (40 mg/ml) and EDC (20 mg/ml) to hard tissue (bone), whereas significant differences are marked with "-*-"

As can be seen in FIG. 23, adding 0.25% w/v HA almost tripled the bonding strength of the bioadhesive matrix from 26.6±9.2 kPa to 71.4±28.2 kPa, while the sample containing β-TCP did not exhibit the same effect.

The adherence ability of other bioadhesives to hard tissues was evaluated and it was found that under similar test conditions, fibrin and gelatin-resorcinol-formaldehyde formulations exhibit ex vivo bonding strengths of 11 and 200 kPa, respectively. The bioadhesive formulations/matrices according to embodiments of the present invention, which incorporated HA particles exhibit bonding strength values to hard tissues that is 6.5-times higher than that of fibrin (71.4±28.2 kPa), and lower than that of the gelatin-resorcin-formaldehyde adhesive, which is considered to be less biocompatible than the bioadhesive formulation presented herein (formaldehyde being significantly more cytotoxic than EDC).

Example 11

Filler Effect on Microstructure of the Matrix

The bulk cross-sections of air-dried bioadhesive matrix specimens containing 0.125% and 0.5% w/v HA and β-TCP respectively were examined using ESEM. The concentrations of gelatin (200 mg/ml), alginate (40 mg/ml) and EDC (20 mg/ml) were kept constant for all samples. The microstructure analysis of a filler-free bioadhesive presented hereinabove has shown that no phase separation occurred in the presence of the three basic components of the bioadhesive formulation, gelatin, alginate and EDC.

The fractographs of the HA-loaded and β-TCP-loaded bioadhesive formulations are presented in FIGS. 24A-F.

As can be seen in FIGS. 24A-F, the fractographs provide a clear perspective on the crystallization of the fillers in the bioadhesive matrix. The fractographs also demonstrate that at the lower concentration, the HA and β-TCP particles are not uniformly dispersed in the adhesive. Higher concentrations of the fillers seem to provide a more uniform dispersion.

The soft tissue bonding strength experiments demonstrated that both HA and β-TCP can be regarded as effective reinforcement fillers, since adding these fillers to the bioadhesive formulation increases its bonding strength.

The crosslinking agent concentration had a significant effect on the bonding strength since it controls the crosslinking density in the bioadhesive matrix. As presented hereinabove, decreasing the crosslinking agent concentration by half, from 20 mg/ml to 10 mg/ml, caused about two-fold reduction in the bonding strength of a bioadhesive matrix stemming from the same formulation. Comparing the bonding strength results of HA-loaded and β-TCP-loaded bioadhesive matrices with a reduced concentration of EDC (10 mg/ml) to that of the filler-free reference bioadhesive (20 mg/ml EDC) indicated that both HA and β-TCP have a compensatory effect on the bonding strength when decreasing the crosslinking agent concentration. Since EDC was shown to have some cytotoxic effects, this compensatory effect also has clinical and medical importance because it enables improving the biocompatibility of the adhesive without compromising its bonding strength and even improving it.

Example 12

Adhesion Mechanism

The two main adhesion mechanisms were tested using the bioadhesive formulations/matrices presented herein:

(1) Mechanical interlocking—adhesion as a result of penetration of the adhesive into pores, grooves and other irregularities on the surface of the adherents.

(2) Chemical adhesion—adhesion as a result of intramolecular bonds (van der Waals, ionic, covalent, hydrogen and/or metallic) between the adhesive agent and molecules on the surface of the adherents.

For most adhesives, the adhesion mechanism is considered to be a combination of mechanical interlocking and chemical adsorption. The proportionate contribution of each of the two mechanisms to the final bonding strength is variable and affected by the adhesive type, the surface roughness and the environment.

In an attempt to elucidate the adhesive mechanism of the bioadhesive formulation/matrix presented herein, the effects of gelatin, alginate and the crosslinking agent's concentrations and their viscosities on the ability of the bioadhesive to bind to soft tissues was further investigated. Accordingly, a qualitative model describing these effects in terms of adherence mechanisms is presented hereinbelow.

All studied formulation series are presented in Tables 8-10.

Table 8 presents the studied bioadhesive formulations, according to some embodiments of the present invention, with different EDC concentrations and various gelatin-alginate combinations, whereas "LV" denotes low viscosity (0.1-0.3 Pa-sec).

TABLE 8

| Gelatin (90-110 Bloom, mg/ml) | LN Alginate (mg/ml) | EDC (mg/ml) |
|---|---|---|
| 200 | 40 | 5 |
|  |  | 10 |
|  |  | 15 |
|  |  | 20 |
| 300 | 30 | 5 |
|  |  | 10 |
|  |  | 15 |
|  |  | 20 |

Table 9 presents the studied bioadhesive formulations with different gelatin Bloom numbers, whereas "LV" denotes low viscosity (0.1-0.3 Pa-sec).

TABLE 9

| Gelatin concentration (mg/ml) | Gelatin Bloom number | LV Aminate concentration (mg/ml) | EDC concentration (mg/ml) |
|---|---|---|---|
| 200 | 90-110 | 40 | 20 |
|  | 175 |  |  |
|  | 300 |  |  |

Table 10 presents the studied bioadhesive formulations with different alginate concentrations and viscosities under various gelatin concentrations, whereas "LV" denotes low viscosity (0.1-0.3 Pa-sec) and "HV" denotes high viscosity (more than 2 Pa-sec).

TABLE 10

| Gelatin (90-110 Bloom number) concentration (mg/ml) | Alginate concentration (mg/ml) | Alginate viscosity* | EDC concentration (mg/ml) |
|---|---|---|---|
| 200 | 10 | LV | 20 |
|  |  | HV |  |
|  | 20 | LV |  |
|  |  | HV |  |
|  | 30 | LV |  |
|  |  | HV |  |
|  | 40 | LV |  |
| 300 | 10 | LV |  |
|  | 20 |  |  |
|  | 30 |  |  |
| 400 | 10 |  |  |
|  | 20 |  |  |
|  | 30 |  |  |

The ex vivo bonding strength measurements were conducted as described hereinabove for the soft tissue studies.

Figure 25A:
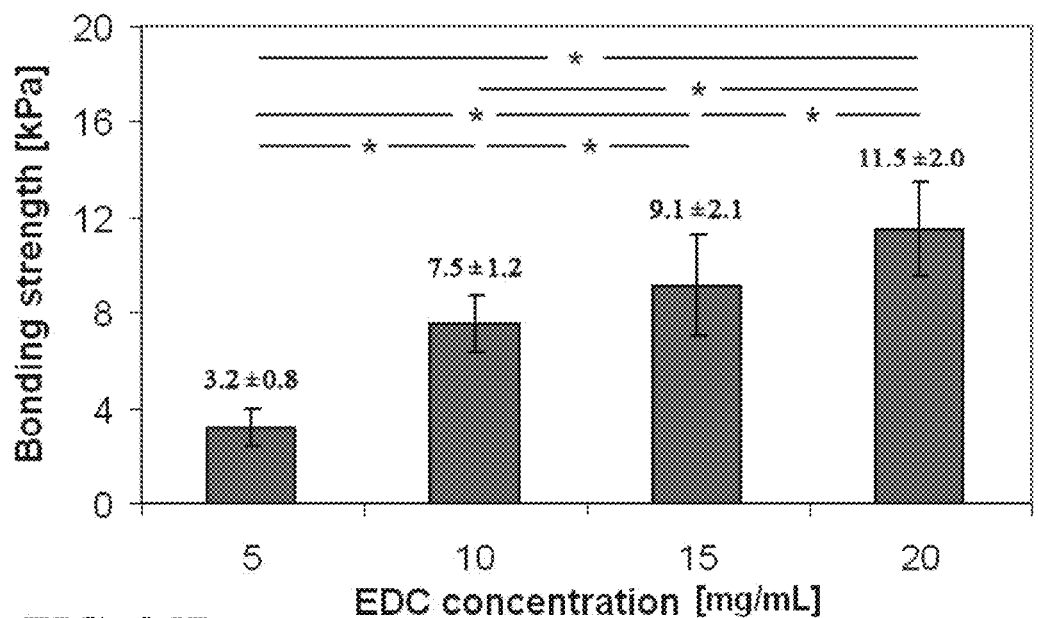
FIGS. 25A-B present bar plots showing the effect of varying the EDC concentration on the bonding strength of a bioadhesive matrix based on a bioadhesive formulation containing 200 mg/ml gelatin and 40 mg/ml LV alginate (Ge-200:Al-40, FIG. 25A), and 300 mg/ml gelatin and 30 mg/ml LV alginate (Ge-300:Al-30, FIG. 25B), whereas significant differences are indicated by "*"
Figure 25B:
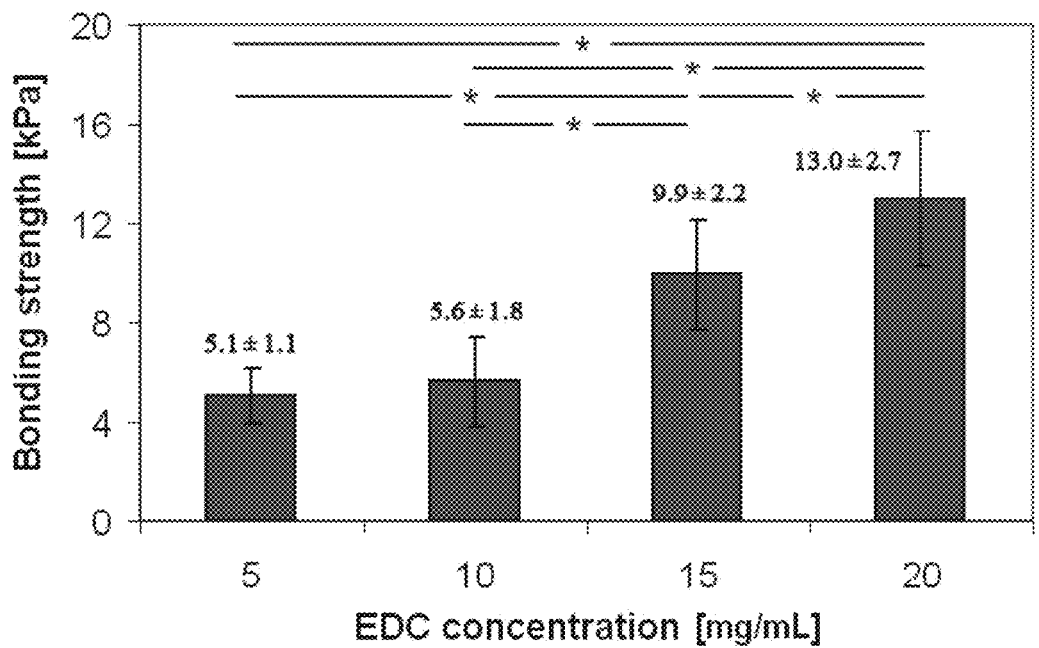

Effect of the EDC Concentration:

The effect of EDC on the bonding strength was evaluated by measuring the bonding strengths of two main combinations, 200 mg/ml gelatin with 40 mg/ml alginate (Ge-200:Al-40), and 300 mg/ml gelatin with 30 mg/ml alginate (Ge-300:Al-30), with a gelatin Bloom number of 90-110 and LV alginate, and with 5, 10, 15 and 20 mg/ml EDC concentrations (see, Table 8) and the results are presented in FIGS. 25A-B.

As can be seen in FIGS. 25A-B, increasing the EDC concentration results in a significant increase in the bonding strength of both gelatin-alginate formulations. For the Ge-200:Al-40 formulation, increasing the EDC concentration from 5 to 20 mg/ml increased the bonding strength of the bioadhesive from 3.2±0.8 to 11.5±2.0 kPa (FIG. 25A), and for the Ge-300:Al-30 formulation, increasing the EDC concentration from 5 to 20 mg/ml increased the bonding strength of the bioadhesive from 5.1±1.1 to 13.0±2.7 kPa (FIG. 25B).

Increasing the EDC concentration leads to a denser bioadhesive crosslinked network. A denser network results in better mechanical properties and greater cohesion strength of the adhesive, which contribute to the mechanical interlocking mechanism of adhesion. A higher crosslinking density can also result in a higher density of covalent bonds between exposed functional groups in the lacerated tissue and the adhesive, which contribute to adhesion through the chemical absorption mechanism.

Effect of the Gelatin Bloom Number:

The Bloom number can give an indication for the strength of the gel formed from a solution with a known concentration. Stronger gels are characterized by higher Bloom numbers. The Bloom number also reflects the average molecular weight of its constituents. The effect of the gelatin Bloom number on the bonding strength was examined by measuring the bonding strength of Ge-200:Al(LV)-40:EDC-20 bioadhesives with three different gelatin Bloom numbers, 90-110, 175 and 300. The viscosity of the non-crosslinked Ge—Al solution of each of these bioadhesive formulations was also evaluated (see, Table 9). The results are presented in FIGS. 26A-B.

Figure 26A:
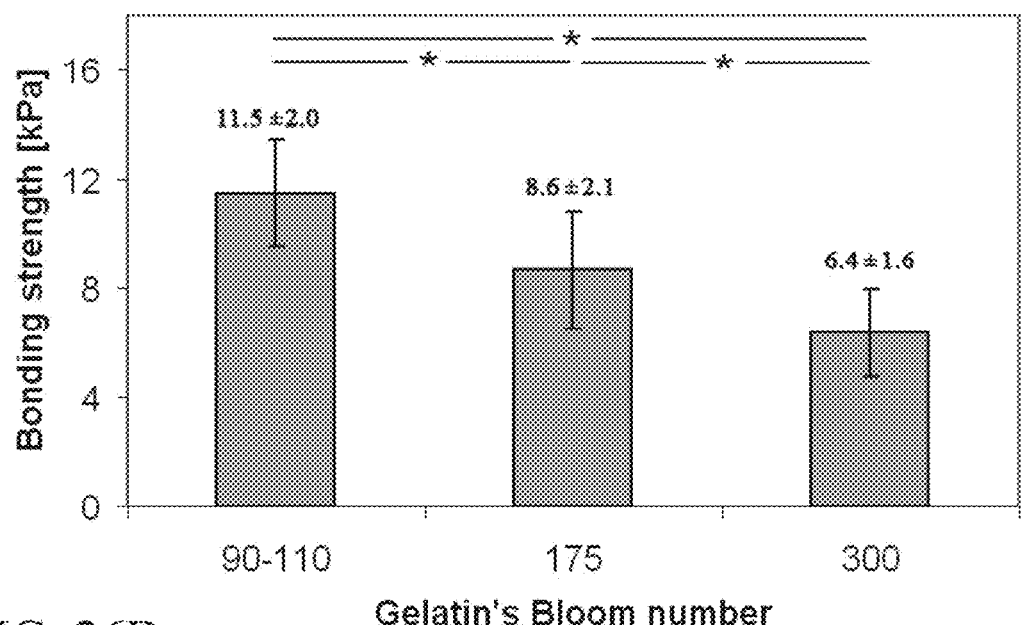
FIGS. 26A-B present bar plots showing the effect of the gelatin's Bloom number on the bonding strength of a bioadhesive matrix resulting from a bioadhesive formulation composed of 200 mg/ml gelatin, 40 mg/ml LV alginate and 20 mg/ml EDC (FIG. 26A), and on the viscosity of their corresponding Ge:Al solutions without EDC (FIG. 26B), whereas significant differences are indicated by "*"

As can be seen in FIG. 26A, increasing the gelatin Bloom number resulted in a consistent and significant decrease in the bonding strength of the bioadhesive, from 11.5±2.0 kPa for gelatin with a Bloom number of 90-110 to 6.4±1.6 kPa for gelatin with a Bloom number of 300. The increase in the molecular weight of gelatin, i.e. increase in the Bloom number, decreases the bioadhesive's mobility and probably also decreases the gelatin strings' ability to penetrate into pores or irregularities on the surface of the soft tissue. The contribution of mechanical interlocking to the general adherence effect of the adhesive to the tissue is therefore reduced, and the bonding strength decreases.

Figure 26B:
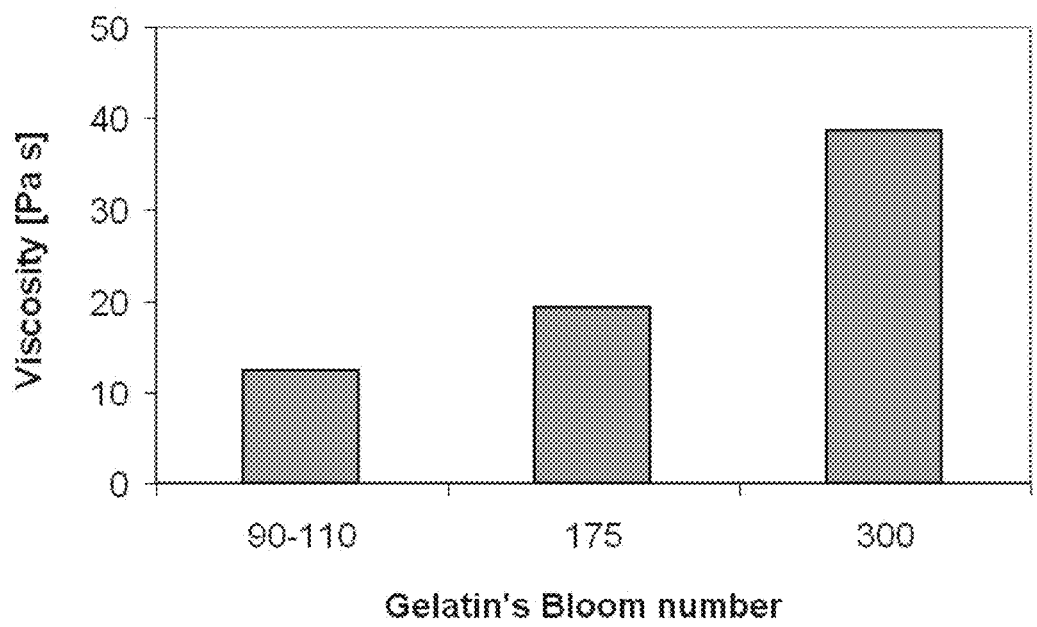

Support for the decrease in the bioadhesive's mobility when increasing the gelatin Bloom number can be found in the initial viscosity results. As can be seen in FIG. 26B, increasing the gelatin Bloom number from 90-110 to 300 resulted in a significant increase in the viscosity, from 12.5 to 38.8 Pa-sec.

Effect of the Polymeric Component Concentrations:

The effect of both polymeric component concentrations on the bonding strength of the bioadhesive was examined using gelatin with a Bloom number of 90-110 based on the results presented hereinabove. Bioadhesive formulations with gelatin concentrations of 200, 300 and 400 mg/ml and LV alginate concentrations of 10, 20, 30 and 40 mg/ml were examined with a constant EDC concentration of 20 mg/ml (see, Table 10). It is noted herein that for bioadhesive formulations based on a gelatin concentration higher than 200 mg/ml, 30 mg/ml was the highest alginate concentration that was tested, since higher alginate concentrations resulted in solutions that were too viscous to be mixed homogenously. The results are presented in FIGS. 27A-C.

Figure 27A:
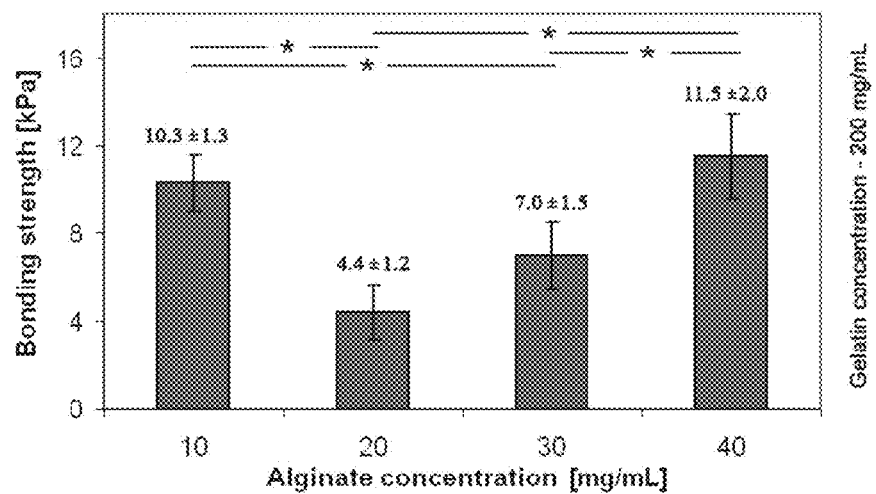
FIGS. 27A-C present bar plots showing the effect of the gelatin and alginate concentrations on the bonding strength of the bioadhesive matrix made from formulations comprising 20 mg/ml EDC, various LV alginate concentrations and 200 mg/ml gelatin (FIG. 27A), 300 mg/ml gelatin (FIG. 27B) and 400 mg/ml gelatin (FIG. 27C), whereas significant differences are indicated by "*"
Figure 27B:
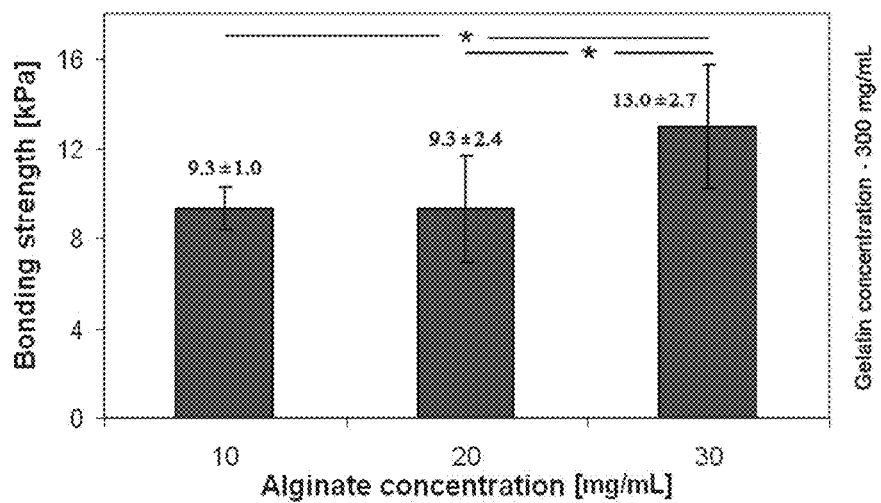
Figure 27C:
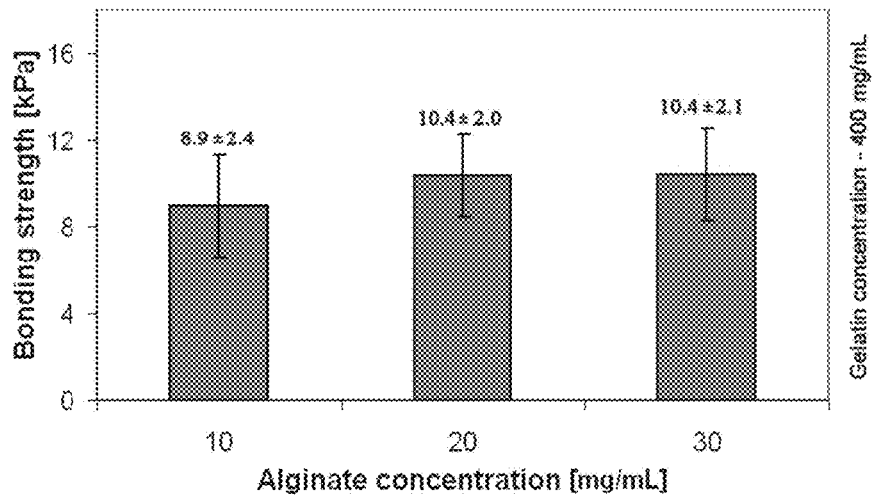

As can be seen in FIGS. 27A-C, when a gelatin concentration of 200 mg/ml was used, maximal bonding strength was achieved for both the highest and the lowest alginate concentrations (10.3±1.3 and 11.5±2.0 kPa for 10 and 40 mg/ml alginate, respectively).

As can further be seen in FIGS. 27B-C, a different effect of the alginate concentration on the bonding strength was obtained for bioadhesive formulations with relatively high gelatin concentrations of 300 and 400 mg/ml. A maximal bonding strength of 13.0±2.7 kPa was measured for the highest alginate concentration that was tested, 30 mg/ml, in bioadhesive formulations with a gelatin concentration of 300 mg/ml (FIG. 27B). The alginate concentration was found to have a small effect on the bonding strength in bioadhesive formulations with a gelatin concentration of 400 mg/ml (FIG. 27C). This different behavior probably indicates that when the gelatin concentration is relatively high, the alginate concentration (which is significantly less than the gelatin concentration) has a minor effect on the crosslinking density and the entanglement level of the 3-dimensional structure of the adhesive, and therefore exhibits only a small effect on the bonding strength.

Effect of Alginate's Viscosity:

The alginate's viscosity correlates to the average molecular weight of its chains. Formulations based on gelatin concentrations of 200, 300 and 400 mg/ml and alginate concentrations of 10, 20 and 30 mg/ml were used. Each formulation was tested with both low viscosity (LV alginate) and high viscosity (HV) alginate, and the EDC concentration was kept at 20 mg/ml. It is noted herein that solutions of 30 mg/ml HV alginate were too viscous to be mixed homogenously with gelatin concentrations higher than 200 mg/ml, and a bioadhesive solution containing 40 mg/ml HV alginate could not be mixed homogenously even with only 200 mg/ml gelatin. The examined formulations are presented in Table 10 and the results are presented in FIGS. 28A-C.

Figure 28A:
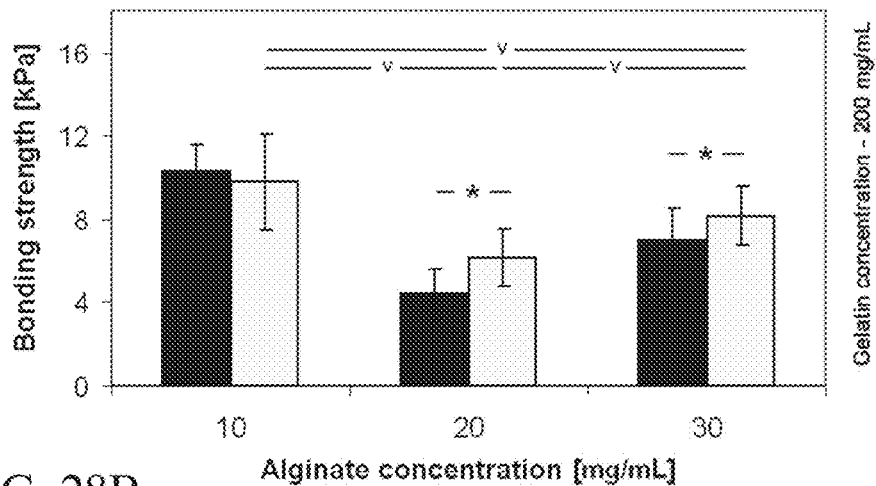
FIGS. 28A-C present comparative bar plot showing the effect of alginate's viscosity on the bonding strength of bioadhesive matrices made from bioadhesive formulations according to embodiments of the present invention, having different gelatin concentrations (Bloom number=90-110) of 200 mg/ml (FIG. 28A), 300 mg/ml (FIG. 28B) and 400 mg/ml gelatin (FIG. 28C), whereas black bars represent LV alginate, white bars represent HV alginate, the alginate concentrations are indicated in the x axis and EDC concentration is 20 mg/ml for all test (significant differences between the bonding strengths of adhesives with similar concentrations but different type of alginate are indicated by "*" and significant differences between the bonding strengths of various HV alginate adhesives are indicated by "v")
Figure 28B:
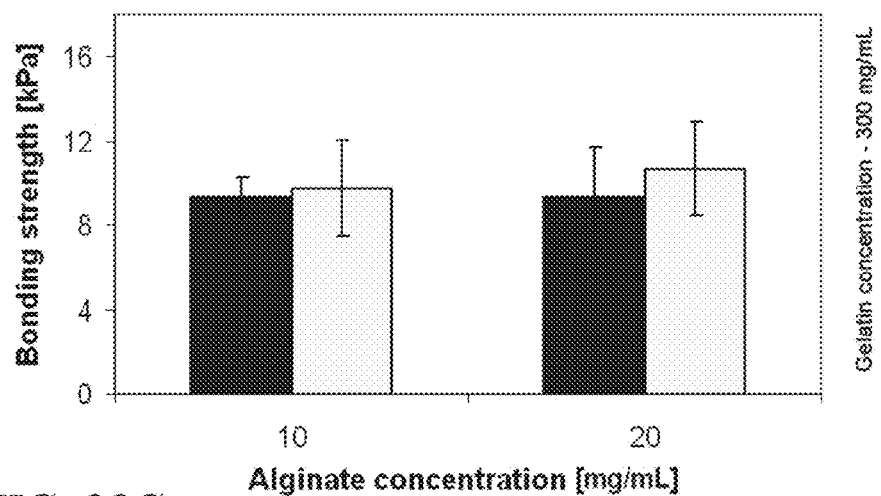
Figure 28C:
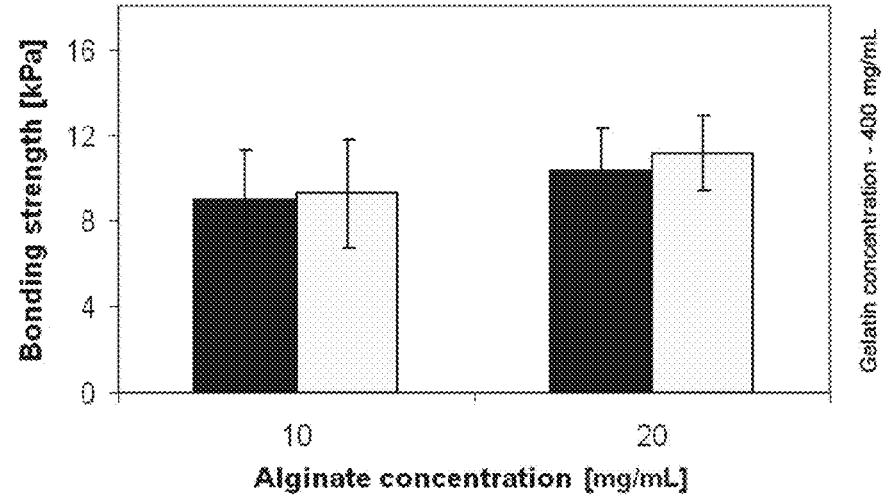

As can be seen in FIGS. 28A-C, HV alginate bioadhesive formulations based on 200 mg/ml gelatin were found to exhibit a similar effect of concentration on the bonding strength as LV alginate, i.e., the highest bonding strengths were obtained for the highest and lowest HV alginate concentrations used in this study (9.8±2.3 and 8.1±1.4 kPa for 10 and 30 mg/ml HV alginate, respectively; FIG. 28A). The effect of alginate's viscosity on the bonding strength was found to be opposite to that of gelatin's viscosity (Bloom number). Use of HV alginate instead of LV alginate slightly improved the bonding strength of the adhesive, except for the lowest alginate concentration that was examined (10 mg/ml), where no significant difference was observed.

Figure 29:
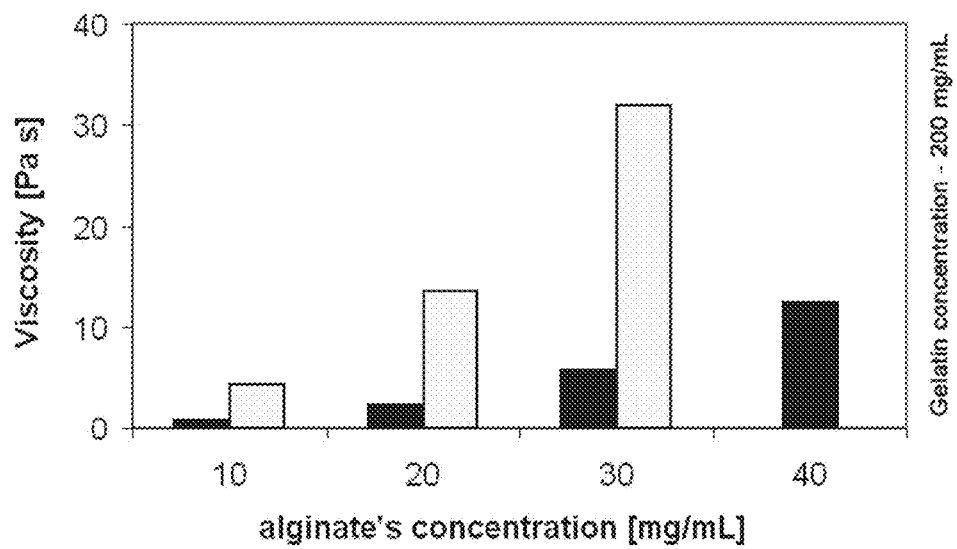
FIG. 29 presents a comparative bar plot showing the effect of the alginate concentration and its viscosity on the viscosity of gelatin-alginate solutions containing gelatin with a Bloom number of 90-110 and a concentration of 200 mg/ml, whereas black bars represent LV alginate, white bars represent HV alginate.

The effect of alginate's viscosity on the total viscosity of the gelatin-alginate solution for formulations based on 200 mg/ml gelatin (90-110 Bloom number) with various alginate concentrations is presented in FIG. 29.

As can be seen in FIG. 29, the viscosity of the bioadhesive formulation precursor (gelatin-alginate solution) is increased 5-6 times when HV alginate is used instead of LV alginate. However, this change enables only a minor improvement in the bonding strength of the bioadhesive matrix resulting from a formulation of similar gelatin-alginate content (see, FIG. 28A). This phenomenon indicates that although alginate's viscosity strongly affects the viscosity of the gelatin-alginate solution, it has only a minor effect on the bioadhesive's strength (FIG. 28A). This may mean that it is possible to create bioadhesive formulations with similar adherence qualities but different viscosities that may be tailored for different applications.

Figure 30:
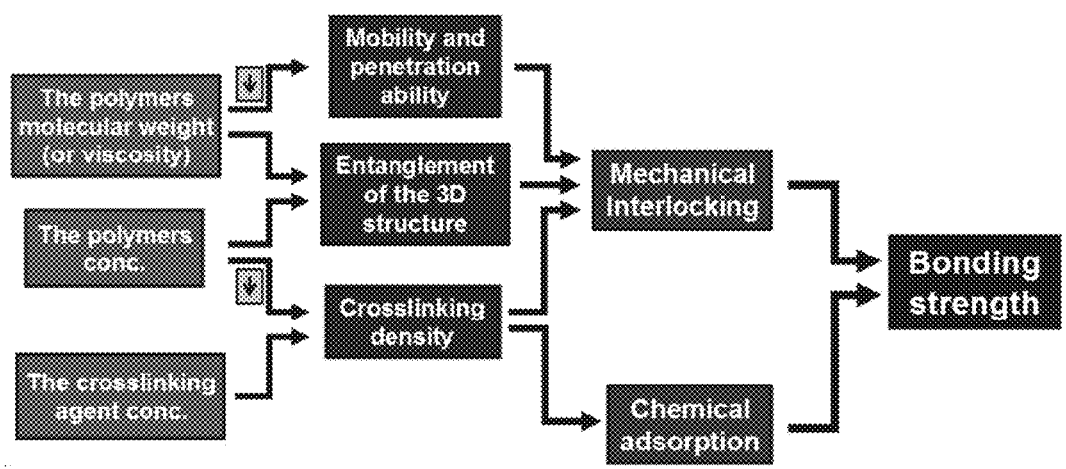
FIG. 30 presents a schematic flow-chart representation of a qualitative model describing the effects of the bioadhesive formulation components' parameters on the bonding strength, whereas the boxed arrow represents an embodiment where a decrease in a certain parameter results in an increase in the following one while all other embodiments, an increase in a certain parameter leads to an increase in the following one.

A Formulation—Strength Model:

A qualitative model which describes the effect of the bioadhesive formulation's parameters on the bonding strength of the resulting bioadhesive matrix is suggested based on the findings presented hereinabove. A schematic representation of this model is presented in FIG. 30.

Example 13

Combined Effect of EDC and NHS

N-hydroxysuccinimide (NHS) was added to the crosslinking reaction of gelatin with EDC in order to improve the crosslinking reaction efficiency, lower the side reactions and lower the amounts of EDC that are needed effect effective crosslinking in the bioadhesive formulations according to some embodiments of the present invention.

This study was designed to identify the optimal amounts of EDC and NHS that affords an effective bioadhesive formulation based on gelatin and alginate. NHS was tested at contents of 0, 10, 20, 40 and 50% (in percent of the amount of EDC) and the results are presented in FIG. 31.

Figure 31A:
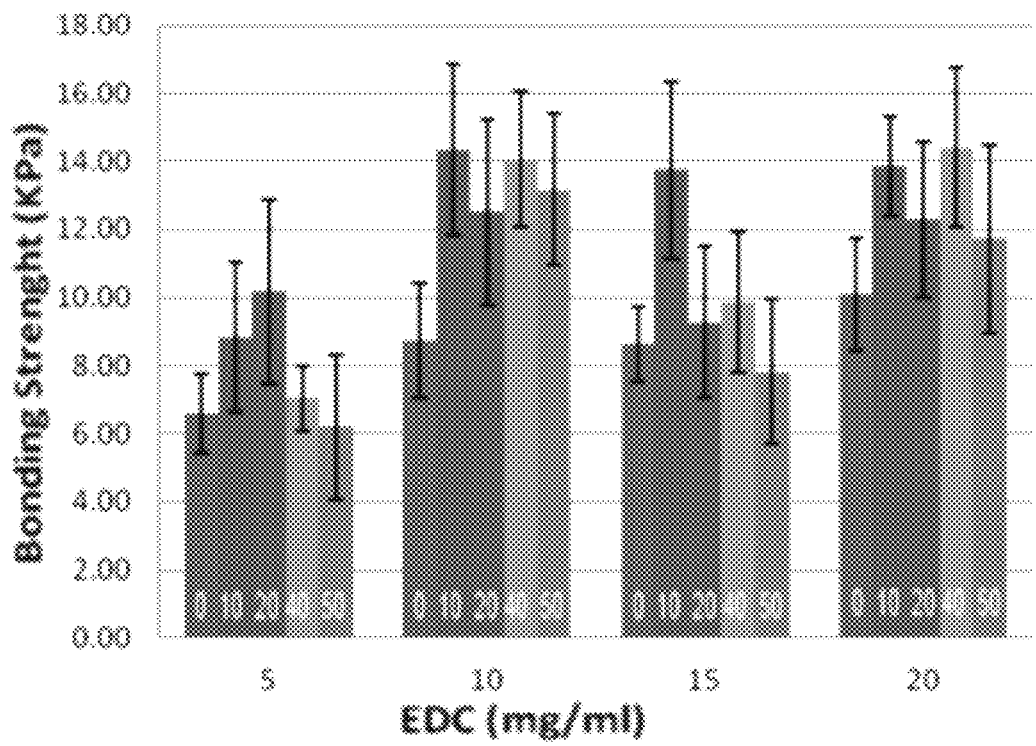
FIGS. 31A-B present a comparative bar plot showing the combined effect of EDC and NHS on the bonding strength of a gelatin-alginate based bioadhesive formulation, according to some embodiments of the present invention, whereas the gelatin concentration is 200 mg/ml, alginate concentration is 40 mg/ml, and the numbers on the bars denote the percent of NHS in the formulation (FIG. 31A), and a bar plot comparing the bioadhesive matrices exhibiting the highest bonding strength (FIG. 31B)
Figure 31B:
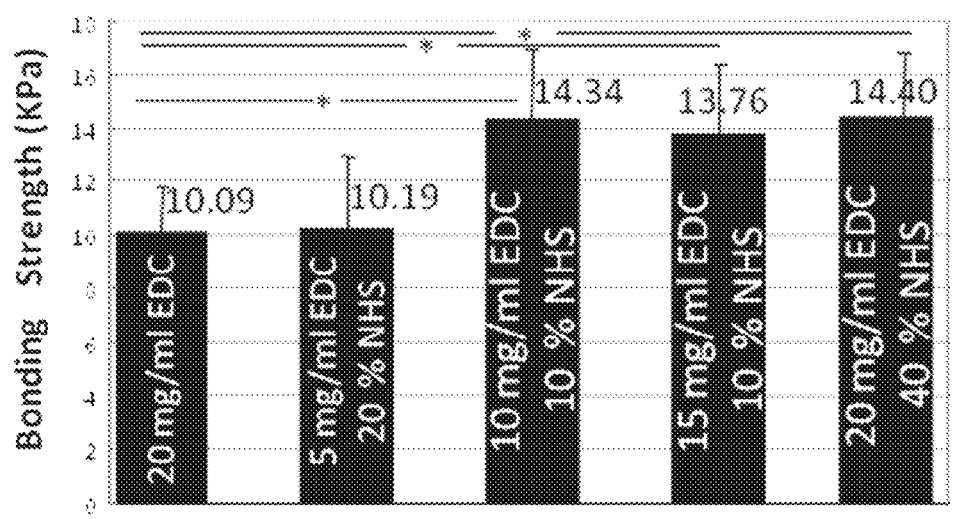

As can be seen in FIGS. 31A-B, incorporation of NHS in the bioadhesive formulation presented herein affords bioadhesive matrices which exhibit higher bonding strengths while using less of crosslinking agent EDC.

These experiments demonstrate that EDC concentrations can be lowered significantly with the addition of relatively small amounts of other crosslinking agents such as NHS.

Example 14

Bioadhesive Formulations Loaded with Antibiotic Drugs

Clindamycin is well known for its activity against Gram-positive cocci, Gram-positive and Gram-negative anaerobes and certain protozoa. Despite the favorable antimicrobial spectrum of clindamycin, its systemic administration is associated with a serious antibiotic-related complication named pseudomembranous enterocolitis. Therefore, delivering this drug locally could potentially decrease the risk of systemic complications. Hence, the study presented herein is aimed at investigating the possibility of loading the bioadhesive formulations/matrices with antibiotic drugs such as clindamycin.

Bioadhesive formulations containing an antibiotic drug were prepared as described hereinabove, and the mechanical properties of the resulting bioadhesive matrices were measured as described hereinabove. The results of the bonding strength measurements of exemplary clindamycin-loaded bioadhesive formulations according to some embodiments of the present invention, are presented in FIGS. 32A-B.

Figure 32A:
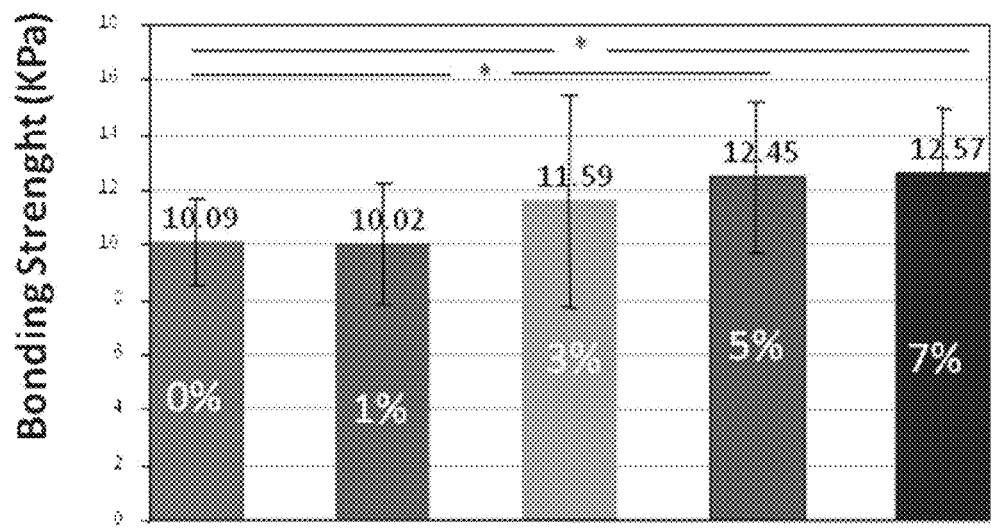
FIGS. 32A-B present bar plots showing the effect of the exemplary antibiotic drug clindamycin on the bonding strength of an exemplary bioadhesive matrix afforded from an exemplary bioadhesive formulation, according to embodiments of the present invention, comprising 200 mg/ml gelatin, 40 mg/ml alginate, and 20 mg/ml EDC, whereas the numbers on the bars denote the percent of clindamycin in the formulation (FIG. 32A), and the effect of the addition of NHS and clindamycin on the bonding strength of a matrix resulting from a bioadhesive formulation comprising 200 mg/ml gelatin, 40 mg/ml alginate, and 10 mg/ml EDC (FIG. 32B).
Figure 32B:
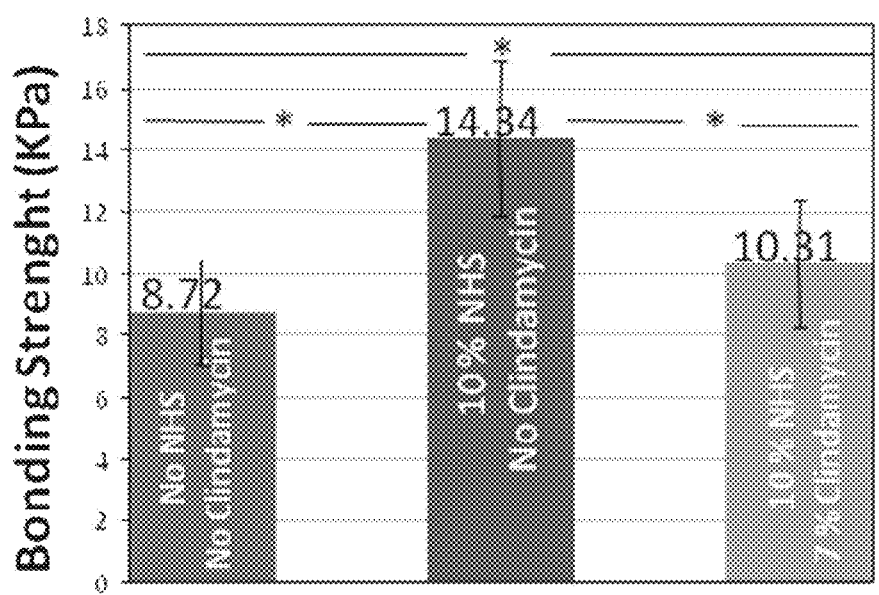

As can be seen in FIGS. 32A-B, since clindamycin does not exhibit carboxylic or primary amines groups, and therefore it is inert to the crosslinking reaction, its presence did not decrease the bonding strength but rather increased it to some extent.

The release profile of clindamicin was also measured according to the protocols presented hereinabove. These studies showed that most of the antibiotic drug was released from the bioadhesive matrix within 6 hours in all studied formulations containing various concentrations of the drug.

Example 15

Bioadhesive Formulations Loaded with Haemostatic Agents

Incorporation of haemostatic agents in the bioadhesive formulations presented herein may be beneficial for various medicinal applications. Hence, the bonding strength of exemplary bioadhesive matrices, formed from bioadhesive formulations prepared with the exemplary haemostatic agents kaolin and tranexamic acid, was investigated, and the results are presented in Table 11.

The exemplary bioadhesive formulations which were chosen for this study and the average bonding strength of the resulting bioadhesive matrix are presented in Table 11.

TABLE 11

| Formulation | Gelatin (mg/ml) | Alginate (mg/ml) | EDC (mg/ml) | NHS (% of EDC) | Bonding strength (kPa) |
|---|---|---|---|---|---|
| 0 | 200 | 40 | 20 | 0 | 13.3 |
| 1 | 200 | 40 | 10 | 10 | 13.3 |
| 2 | 300 | 30 | 10 | 10 | 17.4 |
| 3 | 300 | 30 | 20 | 0 | 18.4 |

The effect of incorporation of the exemplary haemostatic agents kaolin and tranexamic acid in the bioadhesive formulations are presented in Table 12.

TABLE 12

| Formulation | 0 | 1 | 3 | 5 | 7 |
|---|---|---|---|---|---|
| | Kaolin content in % w/v | | | | |
| 1 | 13.3 | 17.5 | 25.5 | 19.5 | 15.5 |
| 2 | 17.4 | 19.6 | 19 | 16.6 | 17.7 |
| 3 | 18.4 | 16.7 | 20.9 | 22.4 | 20.6 |
| | Tranexamic acid content in % w/v | | | | |
| 1 | 13.3 | 9.8 | — | | |
| 2 | 17.4 | 13.9 | 8.4 | | |
| 3 | 18.4 | 13.4 | 10.5 | | |

As can be seen, incorporation of kaolin increases the bonding strength of two of the studied formulations, while incorporation of tranexamic acid resulted in a decreased bonding strength.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A bioadhesive matrix formed by preparing a bioadhesive formulation and allowing a curing time to lapse, wherein said bioadhesive formulation comprises:
   a) gelatin;
   b) alginate;
   c) a coupling agent; and
   d) water,
   wherein:
   the concentration of said gelatin in the formulation ranges from 50 mg/ml to 400 mg/ml, the concentration of said alginate in the formulation ranges from 10 mg/ml to 60 mg/ml, and the concentration of said coupling agent ranges from 10 mg/ml to 30 mg/ml, and wherein the concentrations of the components are selected such that, prior to curing, the formulation is characterized by a room temperature viscosity that ranges from 1 Pa-sec to 50 Pa-sec, and such that the curing time for forming said matrix ranges from 5 seconds to 30 minutes.

2. The matrix of claim 1, wherein the concentrations of the components of said bioadhesive formulation are selected such that said matrix is characterized by at least one of:

a bonding strength of viable biological objects that ranges from 2,000 pascal to 60,000 pascal;

a flexural strength at physiological conditions that ranges from 0.5 MPa to 200 MPa; and a biodegradability rate that ranges from 7 days to 6 months.

3. The matrix of claim 1, wherein the concentration of said gelatin in the formulation ranges from 100 mg/ml to 300 mg/ml.

4. The matrix of claim 1, wherein, in said formulation, the concentration of said gelatin ranges from 200 mg/ml to 300 mg/ml and the concentration of said alginate ranges from 20 mg/ml to 40 mg/ml.

5. The matrix of claim 1, wherein said formulation further comprises a crosslinking promoting agent.

6. The matrix of claim 5, wherein said crosslinking promoting agent is N-hydroxysuccinimide.

7. The matrix of claim 5, wherein, in said formulation, the concentration of said gelatin ranges from 200 mg/ml to 300 mg/ml, the concentration of said alginate ranges from 20 mg/ml to 40 mg/ml, the concentration of said coupling agent ranges from 10 mg/ml to 20 mg/ml, and the concentration of said crosslinking promoting agent ranges from 5% to 20% relative to the amount of said coupling agent in the formulation.

8. The matrix of claim 1, further comprising a bioactive agent.

9. The bioadhesive matrix of claim 1, further comprising a bioactive agent sequestered therein, the bioadhesive matrix being a drug-eluting bioadhesive matrix.

10. A method of forming a bioadhesive matrix, the method comprising preparing a bioadhesive formulation and allowing a curing time to elapse, wherein said bioadhesive formulation comprises:

a) gelatin;
b) alginate;
c) a coupling agent; and
d) water, wherein:

the concentration of said gelatin in the formulation ranges from 50 mg/ml to 400 mg/ml, the concentration of said alginate in the formulation ranges from 10 mg/ml to 60 mg/ml, and the concentration of said coupling agent ranges from 10 mg/ml to 30 mg/ml, and wherein the concentrations of the components are selected such that, prior to curing, the formulation is characterized by a room temperature viscosity that ranges from 1 Pa-sec to 50 Pa-sec, and such that the curing time for forming said matrix ranges from 5 seconds to 30 minutes.

11. The bioadhesive matrix of claim 1, comprising gelatin and alginate covalently coupled to one another and at least one bioactive agent sequestered therein, being characterized by at least one of:

a bonding strength of viable biological objects that ranges from 2,000 pascal to 60,000 pascal;

a flexural strength at physiological conditions that ranges from 0.5 MPa to 200 MPa; and a biodegradability rate that ranges from 7 days to 6 months.

12. The matrix of claim 11, being positioned between at least two objects, at least one of said objects being a biological object.

* * * * *